US008913803B2

(12) United States Patent
Arnon

(10) Patent No.: US 8,913,803 B2
(45) Date of Patent: Dec. 16, 2014

(54) METHOD, DEVICE AND SYSTEM FOR ANALYZING IMAGES

(75) Inventor: Israel Boaz Arnon, Neve Tsuf (IL)

(73) Assignee: Real Imaging Ltd., Lod (IL)

( * ) Notice: Subject to any disclaimer, the term of this patent is extended or adjusted under 35 U.S.C. 154(b) by 967 days.

(21) Appl. No.: 12/452,330

(22) PCT Filed: Jun. 25, 2008

(86) PCT No.: PCT/IL2008/000871
§ 371 (c)(1),
(2), (4) Date: Dec. 24, 2009

(87) PCT Pub. No.: WO2009/001357
PCT Pub. Date: Dec. 31, 2008

(65) Prior Publication Data
US 2010/0135550 A1    Jun. 3, 2010

Related U.S. Application Data

(60) Provisional application No. 60/929,386, filed on Jun. 25, 2007.

(51) Int. Cl.
| G06K 9/00 | (2006.01) |
| G06K 9/32 | (2006.01) |
| A61B 5/01 | (2006.01) |
| G01J 5/00 | (2006.01) |

(52) U.S. Cl.
CPC ........... G01J 5/0022 (2013.01); G06K 2209/05 (2013.01); G01J 2005/0081 (2013.01); G01J 2005/0077 (2013.01); G01J 5/0025 (2013.01); G06K 9/3233 (2013.01); A61B 5/015 (2013.01)
USPC ......................................................... 382/128

(58) Field of Classification Search
None
See application file for complete search history.

(56) References Cited

U.S. PATENT DOCUMENTS

| 4,967,276 A | * | 10/1990 | Murakami et al. | ............ 348/164 |
| 6,023,637 A | * | 2/2000 | Liu et al. | ....................... 600/474 |

(Continued)

FOREIGN PATENT DOCUMENTS

| JP | 2007-516018 | 6/2007 |
| WO | WO 2004/110248 | 12/2004 |

(Continued)

OTHER PUBLICATIONS

Response Dated Jan. 27, 2011 to Communication Pursuant to Article 94(3) EPC of Jul. 27, 2010 From the European Patent Office Re. Application No. 08763628.8.

(Continued)

*Primary Examiner* — Robert Morgan
*Assistant Examiner* — Michael Tomaszewski

(57) ABSTRACT

A method of determining an internal three-dimensional thermally distinguishable region in the living body is disclosed. The method comprises obtaining a synthesized thermospatial image defined over a three-dimensional spatial representation of the living body and having thermal data arranged gridwise over a surface of the three-dimensional spatial representation in a plurality of picture-elements each represented by a intensity value over the grid. The method further comprises searching over the grid for at least one set of picture-elements represented by generally similar intensity values. For at least a few sets of picture-elements, the method defines a plurality of loci, each locus being associated with at least a pair of picture-elements of the set and defined such that each point of the locus is at equal thermal distances from individual picture-elements of the pair. The plurality of loci is used for determining the internal three-dimensional thermally distinguishable region.

4 Claims, 39 Drawing Sheets
(4 of 39 Drawing Sheet(s) Filed in Color)

(56) References Cited

U.S. PATENT DOCUMENTS

| | | | | |
|---|---|---|---|---|
| 7,292,719 | B2* | 11/2007 | Arnon | 382/128 |
| 7,519,210 | B2* | 4/2009 | Hirsch et al. | 382/128 |
| 2001/0046316 | A1* | 11/2001 | Miyano et al. | 382/154 |
| 2002/0173723 | A1* | 11/2002 | Lewis et al. | 600/473 |
| 2007/0213617 | A1* | 9/2007 | Berman et al. | 600/473 |
| 2008/0077019 | A1* | 3/2008 | Xiao et al. | 600/474 |

FOREIGN PATENT DOCUMENTS

| | | |
|---|---|---|
| WO | WO 2006/003658 | 1/2006 |
| WO | WO 2006003658 A2 * | 1/2006 |
| WO | WO 2009/001357 | 12/2008 |

OTHER PUBLICATIONS

Communication Pursuant to Article 94(3) EPC Dated Jul. 27, 2010 From the European Patent Office Re. Application No. 08763628.8.
Communication Relating to the Results of the Partial International Search Dated Nov. 21, 2008 From the International Searching Authority Re.: Application No. PCT/IL2008/000871.
International Preliminary Report on Patentability Dated Jan. 14, 2010 From theInternational Bureau of WIPO Re.: Application No. PCT/IL2008/000871.
International Search Report Dated Feb. 25, 2009 From the International Searching Authority Re.: Application No. PCT/IL2008/000871.
Written Opinion Dated Feb. 25, 2009 From the International Searching Authority Re.: Application No. PCT/IL2008/000871.
Cooke et al. "Identifying Scolisis in the Adolescent with Thermography", Clinical Orthopaedics and Related Research, 148: 172-176, 1980.
Moderhak et al. "Problems of 3D Breast Imaging", Gdansk University of Technology, Department of Biomedical Engineering, 2 P.
Response Dated Jul. 12, 2011 to Communication Pursuant to Article 94(3) EPC of Mar. 3, 2011 From the European Patent Office Re. Application No. 08763628.8.
Translation of Notice of Reason for Rejection Dated Aug. 13, 2013 From the Japanese Patent Office Re. Application No. 2010-514247.
Communication Pursuant to Article 94(3) EPC Dated Dec. 1, 2011 From the European Patent Office Re. Application No. 08763628.8.
Communication Under Rule 71(3) EPC Dated Jul. 16, 2012 From the European Patent Office Re. Application No. 08763628.8.
Office Action Dated Sep. 3, 2012 From the Israel Patent Office Re. Application No. 202923 and Its Translation Into English.
Translation of Office Action Dated Aug. 2, 2012 From the State Intellectual Property Office of the People's Republic of China Re. Application No. 200880104306.4.
Translation of Office Action Dated May 6, 2013 From the State Intellectual Property Office of the People's Republic of China Re. Application No. 200880104306.4.
Office Action Dated Jan. 30, 2014 From the State Intellectual Property Office of the People's Republic of China Re. Application No. 200880104306.4 and Its Translation Into English.
Communication Pursuant to Article 94(3) EPC Dated Mar. 3, 2011 From the European Patent Office Re. Application No. 08763628.8.
Office Action Dated Jul. 21, 2011 From the State Intellectual Property Office of the People's Republic of China Re. Application No. 200880104306.4.
Notice of Reason for Rejection Dated Aug. 1, 2014 From the Japanese Patent Office Re. Application No. 2010-514247 and Its Translation Into English.

* cited by examiner

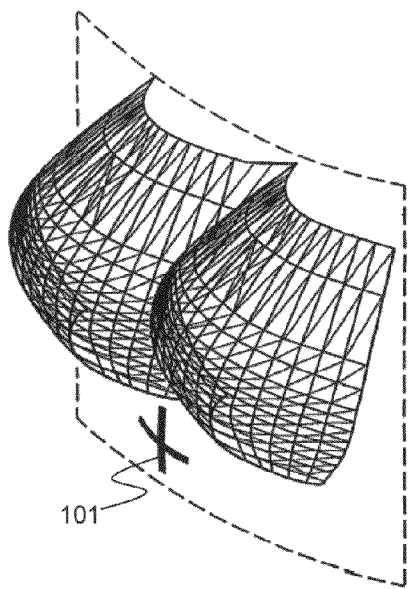
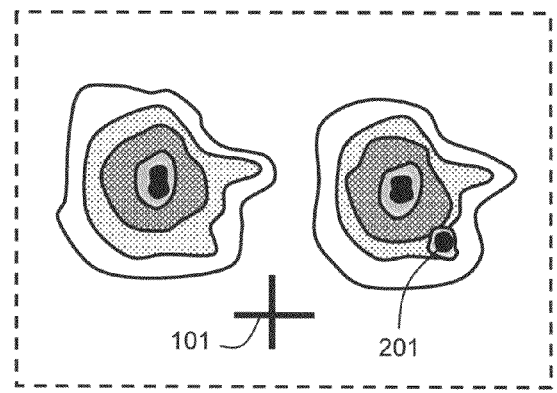
Fig. 1a
Fig. 1b
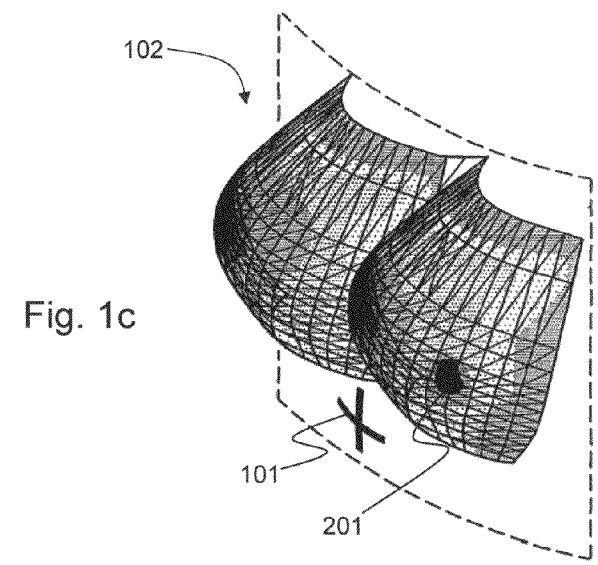
Fig. 1c

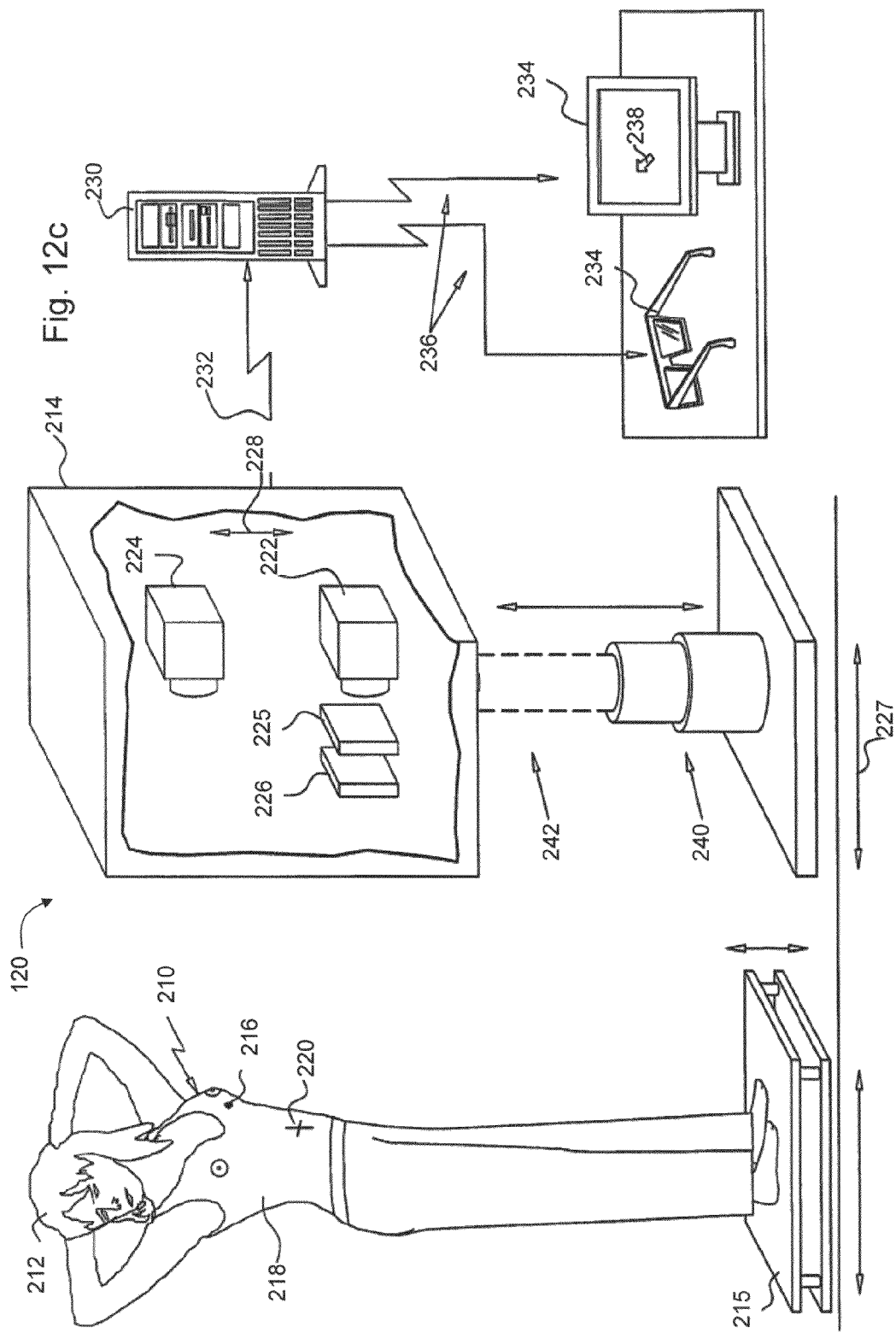

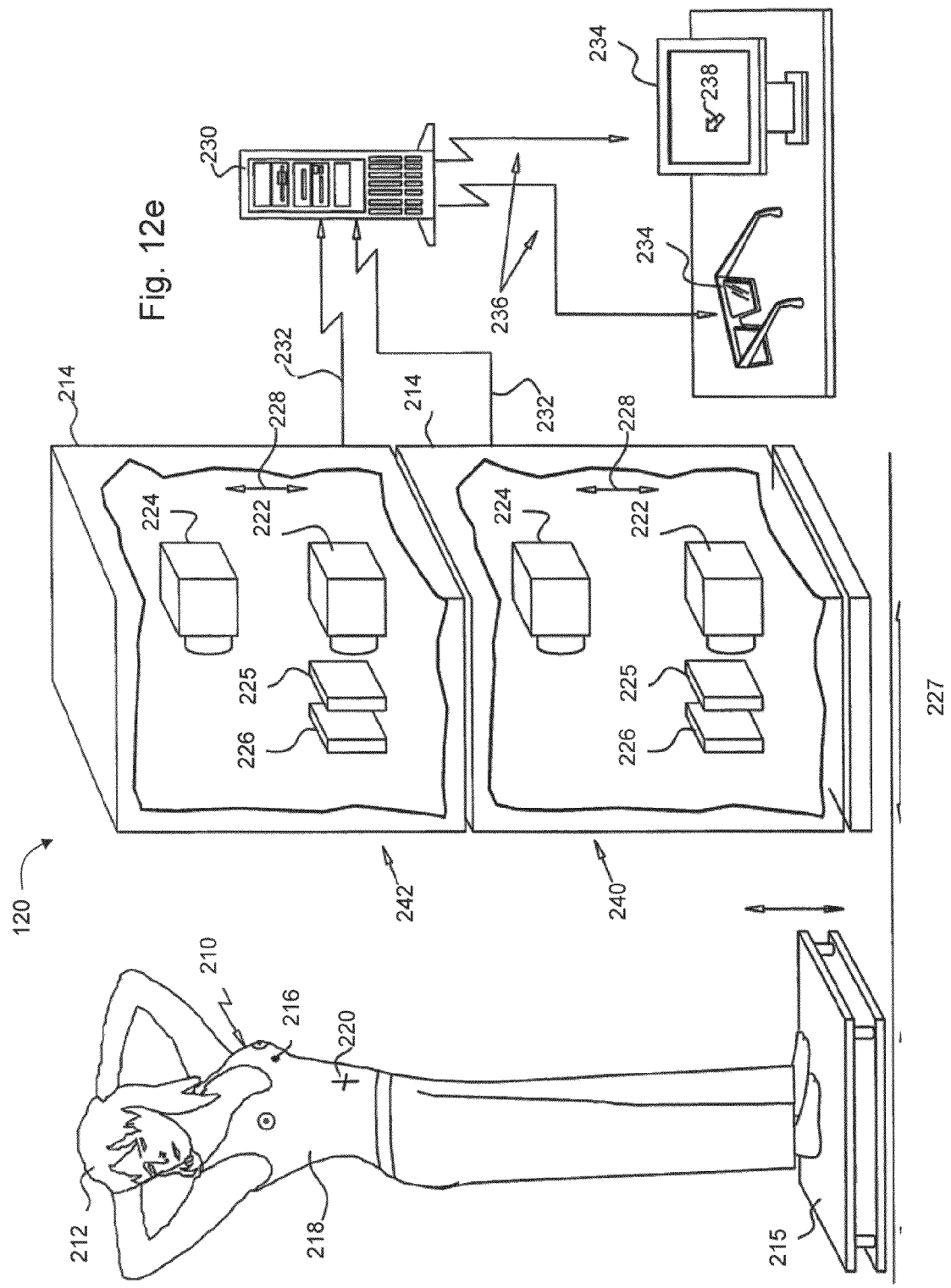

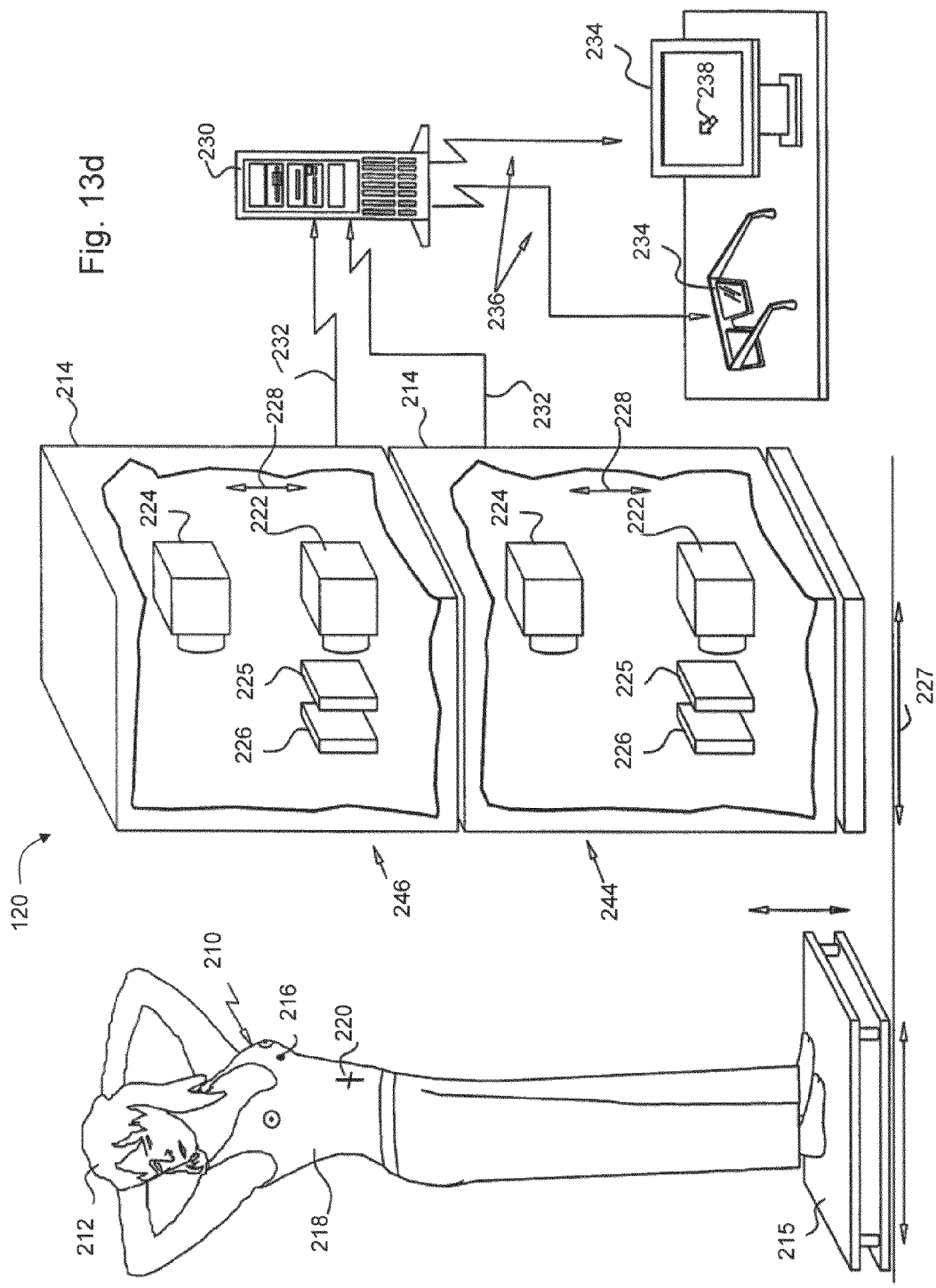

METHOD, DEVICE AND SYSTEM FOR ANALYZING IMAGES

RELATED APPLICATIONS

This application is a National Phase of PCT Patent Application No. PCT/IL2008/000871 having International filing date of Jun. 25, 2008, which claims the benefit of U.S. Provisional Patent Application No. 60/929,386 filed on Jun. 25, 2007. The contents of the above Applications are all incorporated herein by reference.

FIELD AND BACKGROUND OF THE INVENTION

The present invention relates to imaging and, more particularly, to method, device and system for obtaining and analyzing thermographic images.

The use of imaging in diagnostic medicine dates back to the early 1900s. Presently there are numerous different imaging modalities at the disposal of a physician allowing imaging of hard and soft tissues and characterization of both normal and pathological tissues.

Infra red imaging is utilized for characterizing a thermally distinguishable site in a human body for the purposes of identifying inflammation. Infrared cameras produce two-dimensional images known as thermographic images. A thermographic image is typically obtained by receiving from the body of the subject radiation at any one of several infrared wavelength ranges and analyzing the radiation to provide a two-dimensional temperature map of the surface. The thermographic image can be in the form of either or both of a visual image and corresponding temperature data. The output from infrared cameras used for infrared thermography typically provides an image comprising a plurality of pixel data points, each pixel providing temperature information which is visually displayed, using a color code or grayscale code. The temperature information can be further processed by computer software to generate for example, mean temperature for the image, or a discrete area of the image, by averaging temperature data associated with all the pixels or a sub-collection thereof.

Based on the thermographic image, a physician diagnoses the site, and determines, for example, whether or not the site includes an inflammation while relying heavily on experience and intuition.

U.S. Pat. No. 7,072,504 discloses an approach which utilizes two infrared cameras (left and right) in combination with two visible light cameras (left and right). The infrared cameras are used to provide a three-dimensional thermographic image and the visible light cameras are used to provide a three-dimensional visible light image. The three-dimensional thermographic and three-dimensional visible light images are displayed to the user in an overlapping manner.

Also of interest is U.S. Pat. No. 6,442,419 disclosing a scanning system including an infrared detecting mechanism which performs a 360° data extraction from an object, and a signal decoding mechanism, which receives electrical signal from the infrared detecting mechanism and integrates the signal into data of a three-dimensional profile curved surface and a corresponding temperature distribution of the object.

International Patent Publication No. 2006/003658, the contents of which are hereby incorporated by reference, discloses a system which includes non-thermographic image data acquisition functionality and thermographic image data acquisition functionality. The non-thermographic image data acquisition functionality acquires non-thermographic image data, and the thermographic image data acquisition functionality acquires thermographic image data.

There is a widely recognized need for, and it would be highly advantageous to have a method, device and system for obtaining and analyzing thermographic images.

SUMMARY OF THE INVENTION

According to one aspect of the present invention there is provided a method of calculating a thermal path in a body. The method comprises (a) associating thermal data with a surface of at least a portion of the body to thereby generate a thermal data map on the surface; (b) identifying in the thermal data map at least one thermally distinguishable region; and (c) calculating the thermal path in the at least a portion of the body based on a surface distribution of the at least one thermally distinguishable region.

According to further features in preferred embodiments of the invention described below, (a) is effected by collecting thermal radiation from the surface.

According to still further features in the described preferred embodiments the method further comprises correcting the collected thermal radiation for emissivity of tissue in the at least the portion of the body.

According to still further features in the described preferred embodiments the at least one thermally distinguishable region comprises at least two thermally distinguishable region.

According to another aspect of the present invention there is provided a method of calculating a thermal path in a living body, comprises: obtaining a synthesized thermospatial image defined over a three-dimensional spatial representation of the living body and having thermal data associated with a surface of the three-dimensional spatial representation. The thermal data are preferably arranged gridwise over the surface in a plurality of picture-elements each represented by a intensity value over the grid. The method further comprises identifying at least one thermally distinguishable spot in the thermospatial image, and using the thermospatial image and the thermally distinguishable spot for calculating the thermal path.

According to further features in preferred embodiments of the invention described below, the method further comprises using at least two thermal trajectories so as to determine an internal three-dimensional thermally distinguishable region in the living body.

According to still further features in the described preferred embodiments the method further comprises: obtaining an additional synthesized thermospatial image representing a different posture of the living body; repeating the thermally distinguishable spot identification and the gradient calculation so as to determine an internal three-dimensional thermally distinguishable region corresponding to the different posture; and comparing internal three-dimensional thermally distinguishable regions corresponding to different postures.

According to yet another aspect of the present invention there is provided an apparatus for calculating a thermal path in a living body, comprises: an input unit for receiving a synthesized thermospatial image; a spot identification unit, for identifying at least one thermally distinguishable spot in the synthesized thermospatial image; and a calculator for calculating the thermal path in the living body based on the thermospatial image and the thermally distinguishable spot.

According to still further features in the described preferred embodiments the apparatus further comprises a region determination unit, designed and configured for determining an internal three-dimensional thermally distinguishable region in the living body based on at least two thermal trajectories.

According to still further features in the described preferred embodiments the thermal path is calculated by calculating a spatial gradient of the surface at the spot.

According to yet another aspect of the present invention there is provided a method of determining an internal three-dimensional thermally distinguishable region in the living body, the method comprises: obtaining a synthesized thermospatial image; searching over the grid for at least one set of picture-elements represented by generally similar intensity values; and for at least one of the at least one set of picture-elements, defining a plurality of loci, each locus being associated with at least a pair of picture-elements of the set and defined such that each point of the locus is at equal thermal distances from individual picture-elements of the pair, and using the plurality of loci for determining the internal three-dimensional thermally distinguishable region.

According to still another aspect of the present invention there is provided an apparatus for determining an internal three-dimensional thermally distinguishable region in the living body, the apparatus comprises: an input unit for receiving a synthesized thermospatial image; a searching unit for searching over the grid for at least one set of picture-element represented by generally similar intensity values; a locus definition unit for defining a plurality of loci, each locus being associated with at least a pair of picture-elements of the set and defined such that each point of the locus is at equal thermal distances from individual picture-elements of the pair; and a region determination unit for determining the internal three-dimensional thermally distinguishable region based on the plurality of loci.

According to further features in preferred embodiments of the invention described below, at least one locus of the plurality of loci is a plane.

According to still further features in the described preferred embodiments the internal three-dimensional thermally distinguishable region is at least partially bounded by the plurality of loci.

According to still further features in the described preferred embodiments the internal three-dimensional thermally distinguishable region is determined based on intersecting lines of at least a few of the plurality of loci.

According to still further features in the described preferred embodiments the method further comprises locating a source region within the internal three-dimensional thermally distinguishable region.

According to still further features in the described preferred embodiments the apparatus further comprises a source region locator, for locating a source region within the internal three-dimensional thermally distinguishable region.

According to still further features in the described preferred embodiments the source region is selected from the group consisting of a centroid, a weighted centroid and a center-of-mass of the internal three-dimensional thermally distinguishable region.

According to an additional aspect of the present invention there is provided a method of determining a number of thermally distinguishable objects in the living body, the method comprises: obtaining a synthesized thermospatial image in which the thermal data is characterized by closed isothermal contours surrounding at least one thermally distinguished spots on the surface; determining an internal three-dimensional thermally distinguishable region in the living body based on the synthesized thermospatial image; analyzing the three-dimensional spatial representation so as to define a boundary within the three-dimensional spatial representation, wherein points residing on one side of the boundary correspond to a single thermally distinguished spot on the surface while points residing on another side of the boundary correspond to a plurality of thermally distinguished spots on the surface; and comparing the internal three-dimensional thermally distinguishable region with the boundary so as to determine the number of thermally distinguishable objects in the living body.

According to yet an additional aspect of the present invention there is provided apparatus for determining a number of thermally distinguishable objects in the living body, the apparatus comprises: an input unit for receiving a synthesized thermospatial image; a region determination unit for determining an internal three-dimensional thermally distinguishable region in the living body based on the synthesized thermospatial image; an analyzer for analyzing the three-dimensional spatial representation so as to define a boundary within the three-dimensional spatial representation, wherein points residing on one side of the boundary correspond to a single thermally distinguished spot on the surface while points residing on another side of the boundary correspond to a plurality of thermally distinguished spots on the surface; and a comparison unit for comparing the internal three-dimensional thermally distinguishable region with the boundary so as to determine the number of thermally distinguishable objects in the living body.

According to further features in preferred embodiments of the invention described below, the method further comprises acquiring at least one thermographic image and mapping the at least one thermographic image on the three-dimensional spatial representation so as to form the synthesized thermospatial image.

According to still further features in the described preferred embodiments the mapping comprises weighting the at least one thermographic image according to emissivity data of the living body.

According to still further features in the described preferred embodiments the at least one thermographic image comprises a plurality of thermographic images.

According to still further features in the described preferred embodiments at least two of the thermographic images are acquired when the living body is at a different posture.

According to still further features in the described preferred embodiments, the at least one additional synthesized thermospatial image corresponds to a different posture of the living body.

According to still further features in the described preferred embodiments the method further comprises: obtaining a plurality of three-dimensional spatial representations of the living body; for at least two three-dimensional spatial representations, analyzing each three-dimensional spatial representation so as to determine expected topology of isothermal contours on a surface of the three-dimensional spatial representation; and selecting a viewpoint for the at least one thermographic image and/or a posture of the living body based on the expected topologies.

According to still further features in the described preferred embodiments the method further comprises: obtaining at least one additional three-dimensional spatial representation of the living body, corresponding to a different viewpoint with respect to, and/or a different posture of, the living body; based on the internal three-dimensional thermally distinguishable region in the living body, constructing expected topology of isothermal contours on a surface of the at least one additional three-dimensional spatial representation; obtaining at least one additional synthesized thermospatial image corresponding to the different viewpoint and/or the different posture; comparing the at least one synthesized thermospatial image to the expected topology of the isothermal contours; and issuing a report relating to the comparison.

According to still further features in the described preferred embodiments method further comprises constructing the three-dimensional spatial representation.

According to still further features in the described preferred embodiments the obtaining the three-dimensional spatial representation comprises illuminating the body with a pattern in the infrared range, using at least one thermographic imaging device for acquiring at least one thermographic image of the body and the pattern, calculating range data corresponding to the pattern, and using the at least one thermographic image and the range data for constructing the three-dimensional spatial representation of the body.

According to still an additional aspect of the present invention there is provided a system for thermospatial imaging of an anterior of a living body, the system comprises an intracorporeal probe system having therein at least one thermographic imaging device for acquiring at least one thermographic image of the anterior of the living body, and a data processor for analyzing image data received from the intracorporeal probe system so as to provide and display a synthesized thermospatial image of the anterior of the living body.

According to still further features in the described preferred embodiments the system further comprises at least one visible light imaging device for acquiring at least one visible light image of the anterior of the living body.

According to still further features in the described preferred embodiments the system further comprises an illuminating device for illuminating the anterior of the body with a pattern.

According to still further features in the described preferred embodiments the intracorporeal probe system is adapted to be inserted through the anus.

According to still further features in the described preferred embodiments the intracorporeal probe system is adapted to be inserted through the vagina.

According to still further features in the described preferred embodiments the intracorporeal probe system is adapted to be inserted through the urethra.

According to still further features in the described preferred embodiments the intracorporeal probe system is adapted to be inserted through the esophagus.

According to still further features in the described preferred embodiments the intracorporeal probe system is mounted on a transport mechanism.

According to still further features in the described preferred embodiments the transport mechanism is selected from the group consisting of an endoscopic probe and a catheter.

According to a further aspect of the present invention there is provided a method which comprises acquiring a series of thermographic images of the living body from a predetermined viewpoint; comparing the thermographic images to extract thermal changes in the thermographic images; and when the thermal changes are below a predetermined threshold, issuing a report indicating that the living body is at a generally stable thermal condition.

According to still further features in the described preferred embodiments the acquisition and the comparison is performed substantially contemporaneously.

According to still further features in the described preferred embodiments at least a few thermographic images are compared to a single previously acquired thermographic image.

According to still further features in the described preferred embodiments at least a few thermographic images are compared to a plurality of previously acquired thermographic images.

According to still further features in the described preferred embodiments the method further comprises displaying the thermal changes on a display device.

According to yet a further aspect of the present invention there is provided a method of monitoring a position of a medical device in a living body, comprises setting a temperature of the medical device to a temperature which is sufficiently different from an average temperature of the living body, forming at least one synthesized thermospatial image of the living body, and using the at least one synthesized thermospatial image for monitoring the position of the insertable device in the living body.

According to still a further aspect of the present invention there is provided a medical device insertable into a living body, comprises a hollow structure having a proximal end, a distal end and an optical fiber extending from the proximal end to the a distal end, the optical fiber being designed and constructed to transmit thermal radiation from the from the distal end to the proximal end.

According to still further features in the described preferred embodiments the hollow structure and the optical fiber are made of different materials.

According to still further features in the described preferred embodiments the optical fiber is defined by a passageway in the hollow structure.

According to still a further aspect of the present invention there is provided an illuminating device for a range imaging system, comprises, a light source for generating a light beam, a dynamic beam deflector and an image forming element having a plurality of distinguished regions each being designed for forming a different image, wherein the dynamic beam deflector is designed and configured to scan the image forming element to form different images at different times.

According to still further features in the described preferred embodiments the light source comprises a laser device, and the light beam is a laser beam.

According to still further features in the described preferred embodiments the dynamic beam deflector comprises a movable mirror.

According to still further features in the described preferred embodiments the dynamic beam deflector comprises an electrooptical material.

According to still a further aspect of the present invention there is provided a method of constructing a three-dimensional spatial representation of a body, the method comprises: illuminating the body with a pattern in the infrared range; using at least one thermographic imaging device for acquiring at least one thermographic image of the body and the pattern; calculating range data corresponding to the pattern; and using the at least one thermographic image and the range data for constructing the three-dimensional spatial representation of the body.

According to still further features in the described preferred embodiments the acquiring comprises acquiring at least two thermographic images of the body and the pattern from at least two different viewpoints.

According to still a further aspect of the present invention there is provided a system for constructing a three-dimensional spatial representation of a body, comprises: an illuminating device, designed and constructed for illuminating the body with a pattern in the infrared range; at least one thermographic imaging device designed and constructed for acquiring at least one thermographic image of the body and the pattern; and a data processor designed and configured for calculating range data corresponding to the pattern, and using the at least one thermographic image and the range data for constructing the three-dimensional spatial representation of the body.

According to still further features in the described preferred embodiments the at least one thermographic imaging device is designed and constructed for acquiring at least two thermographic images of the body and the pattern from at least two different viewpoints.

According to still further features in the described preferred embodiments the pattern is selected to allow construction of a three-dimensional spatial representation by temporal coding.

According to still further features in the described preferred embodiments the pattern is selected to allow construction of a three-dimensional spatial representation by spatial coding.

According to still further features in the described preferred embodiments the range data are calculated by time-of-flight technique.

According to still further features in the described preferred embodiments the range data are calculated by triangulation.

According to still further features in the described preferred embodiments a pulse length characterizing the illumination is shorter than 20 milliseconds.

According to still further features in the described preferred embodiments the acquisition of the at least one thermographic image is characterized by an exposure time which is less than 20 milliseconds.

According to still further features in the described preferred embodiments the acquisition of the at least one thermographic image comprises multiple readouts during a single exposure time.

According to still further features in the described preferred embodiments at least two readouts of the multiple readouts are executed accumulatively.

According to still further features in the described preferred embodiments the illumination is effected by laser light.

According to still further features in the described preferred embodiments the method further comprises, for at least a few thermographic images, filtering out image data originating from heat generated by the body.

According to still further features in the described preferred embodiments the method further comprises acquiring at least one thermographic image of the body without the pattern, wherein the filtering out the image data comprises subtracting thermographic images acquired without the pattern from thermographic images acquired with the pattern.

According to still further features in the described preferred embodiments the image data processor is designed and configured for filtering out image data originating from heat generated by the body.

According to still further features in the described preferred embodiments the image data processor is designed and configured subtracting thermographic images acquired without the pattern from thermographic images acquired with the pattern thereby to filter out the image data.

According to still a further aspect of the present invention there is provided a method of constructing a three-dimensional spatial representation of a body, the method comprises: illuminating the body with a series of spots, wherein at least one spot of the series is distinguishable from all other spots in the series; using at least one imaging device for acquiring at least two images of the body and the series of spots from at least two different viewpoints; locating the series of spots in each image; in each image, identifying the at least one distinguishable spot and using the at least one distinguishable spot for identifying all other spots in the series; and calculating range data for the series of spots and using the range data for constructing the three-dimensional spatial representation of the body.

According to still a further aspect of the present invention there is provided a method of calibrating a range imaging system, comprises: accessing a database of figures which comprises a plurality of entries, each having a figure entry and an angle entry corresponding to a viewpoint of the figure entry; illuminating the body with a figure; using at least one imaging device for acquiring at least two images of the body and the figure from at least two different viewpoints; for at least two images, identifying the figure, searching over the database for a figure entry being generally similar to the figure and extracting a respective angle entry from the database, thereby providing at least two angles; based on the at least two angles, calculating range data for the figure and using the range data for calibrating the range imaging system.

According to still a further aspect of the present invention there is provided a method of calibrating a thermospatial imaging system, the system having at least one at least one thermographic imaging device and at least one visible light imaging device, the method comprises: illuminating a body with a pattern in a plurality of wavelengths, wherein at least one wavelength of the plurality of wavelengths is detectable by the one at least one thermographic imaging device and at least one wavelength of the plurality of wavelengths is detectable by the one at least one visible light imaging device; using the at least one at least one thermographic imaging device for acquiring at least one thermographic image of the pattern, and at least one visible light imaging device for acquiring at least one visible light image of the pattern; and calibrating the three-dimensional thermographic imaging device using the thermographic and the visible light images.

According to still further features in the described preferred embodiments the at least one thermographic image and at least one visible light image are acquired substantially simultaneously.

According to still a further aspect of the present invention there is provided a method of constructing a three-dimensional spatial representation of a body, the method comprises: illuminating the body with coded patterns using a pattern projector operable to generate at least two different colors of light, in a manner such that coded patterns of different colors are mutually shifted; acquiring at least one image of the coded pattern to provide image data; and calculating three-dimensional positions of the coded patterns based on the image data, thereby constructing a three-dimensional spatial representation of the body.

According to still a further aspect of the present invention there is provided a system for constructing a three-dimensional spatial representation of a body, the system comprises: a pattern projector operable to illuminate the body with coded patterns of at least two different colors of light in a manner such that coded patterns of different colors are mutually shifted; an imaging device for acquiring at least one image of the coded pattern, thereby to provide image data; and an image data processor designed and configured for calculating three-dimensional positions of the coded patterns, based on the image data.

According to still further features in the described preferred embodiments the at least two coded patterns are mutually shifted by one pixel size.

According to still further features in the described preferred embodiments the pattern projector is operable to project coded patterns of different colors sequentially.

According to still further features in the described preferred embodiments coded patterns of different colors are mutually shifted by an amount which is lower than the characteristic distance between centers of adjacent projected pixels.

According to still further features in the described preferred embodiments the acquisition of the at least one image is characterized by an exposure time which is less than 20 milliseconds.

According to still further features in the described preferred embodiments the acquisition of the at least one image comprises multiple readouts during a single exposure time.

According to still further features in the described preferred embodiments the at least two different colors comprise a first color a second color and a third color and the acquisition of the at least one image comprises three readouts during a single exposure time.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The patent or application file contains at least one drawing executed in color. copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 2:
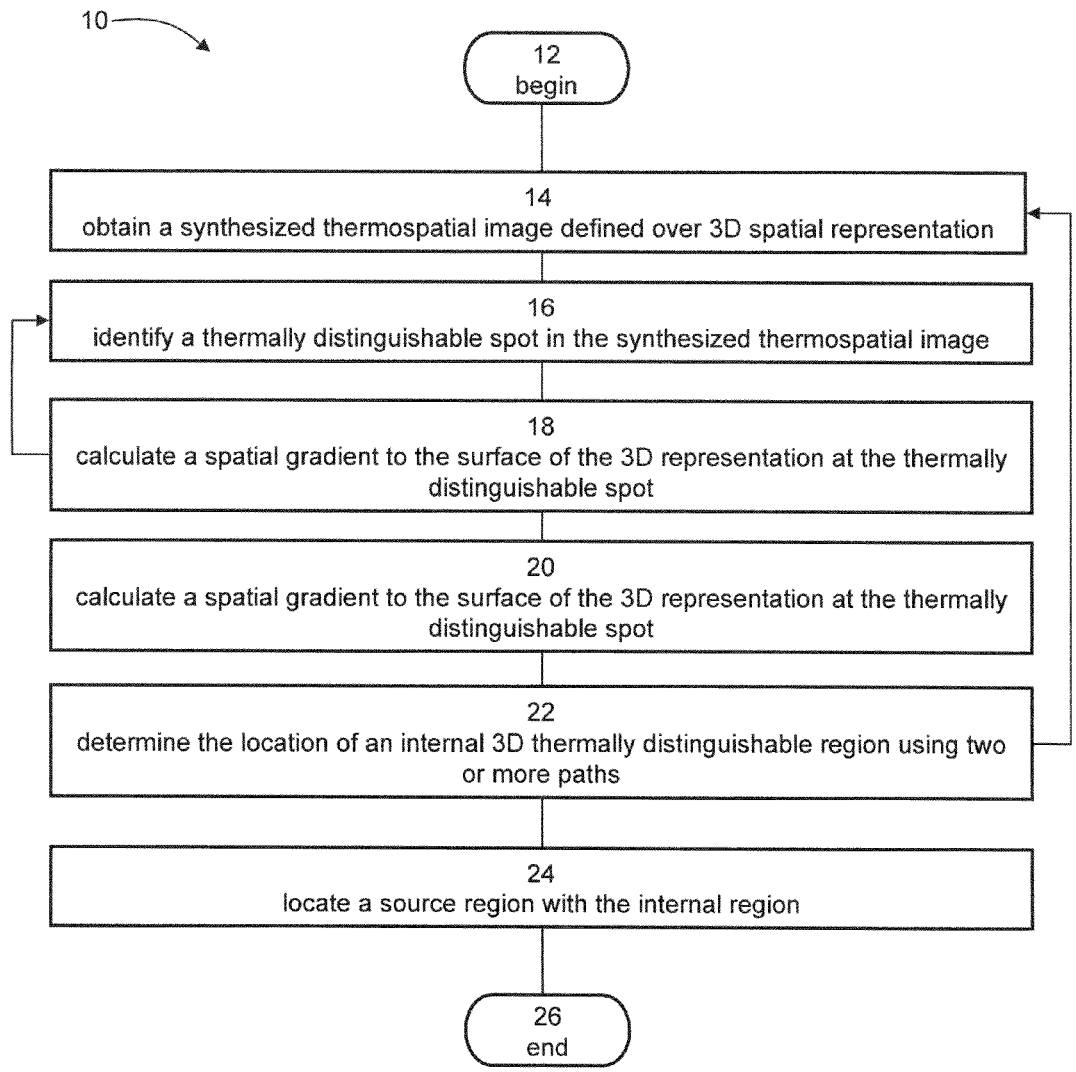
Figure 3A:
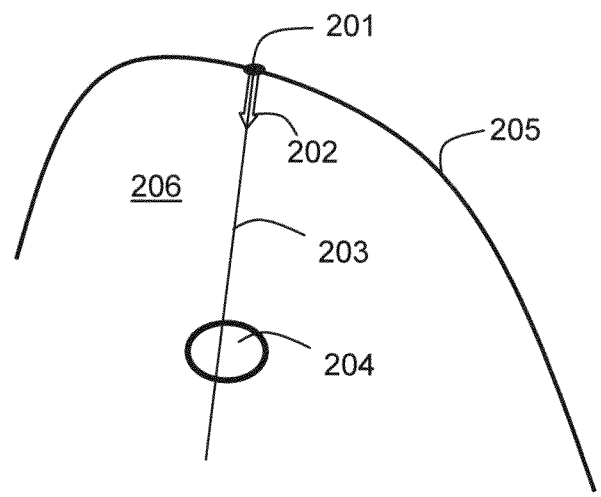
Figure 3B:
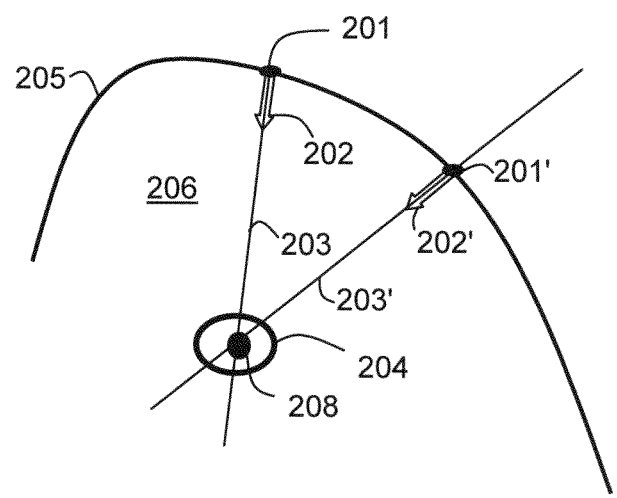
Figure 4:
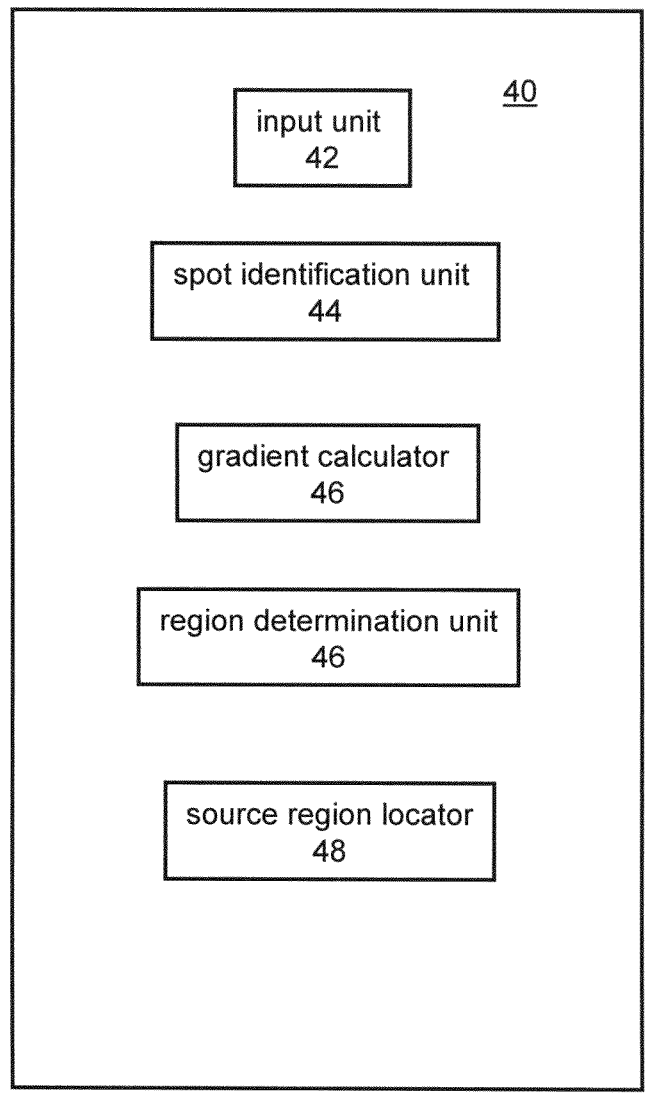
Figure 5:
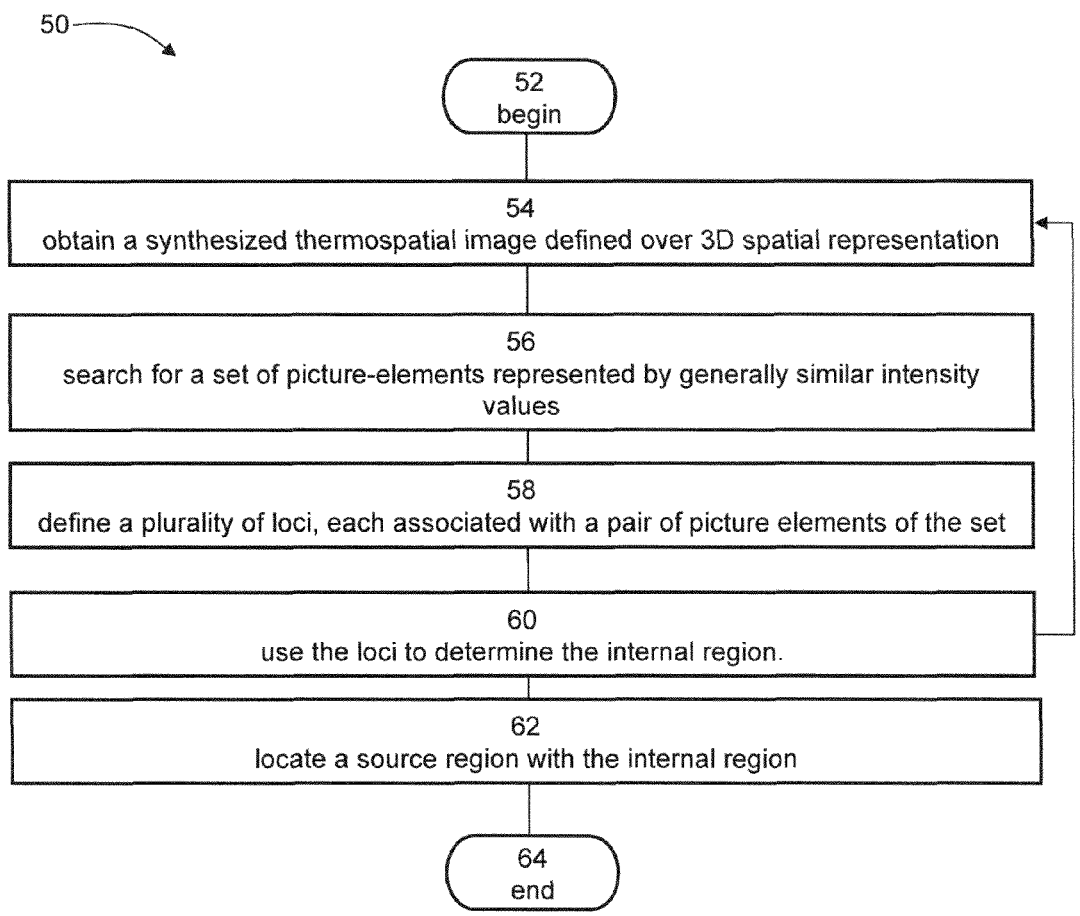
Figure 6A:
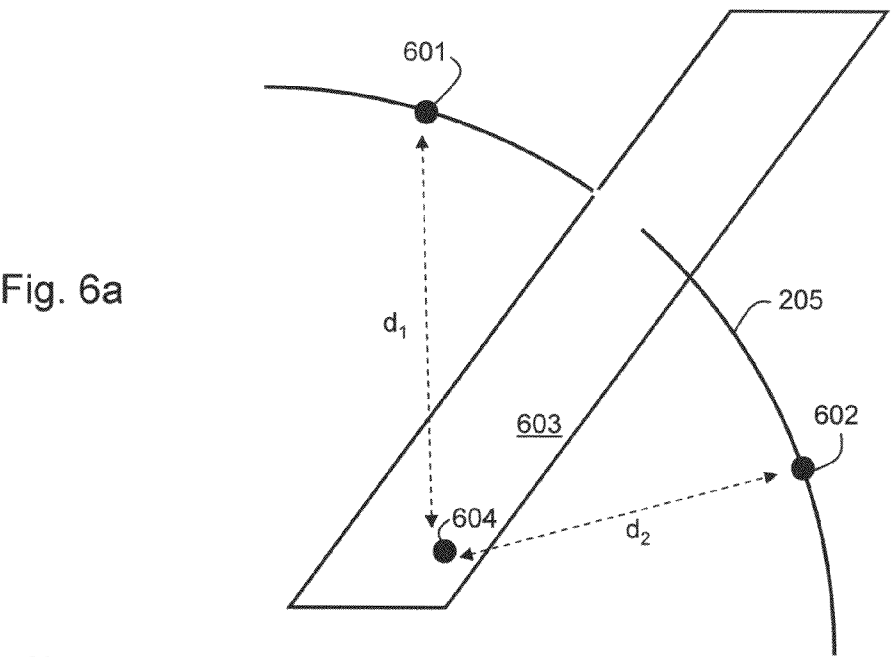
Figure 6B:
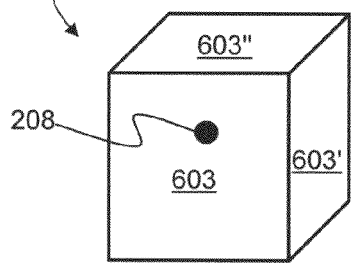
Figure 6C:
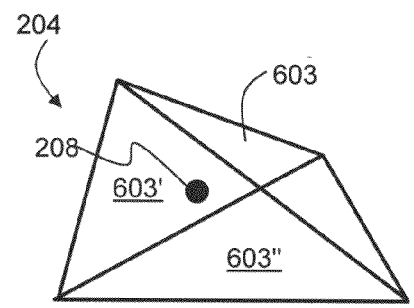
Figure 6D:
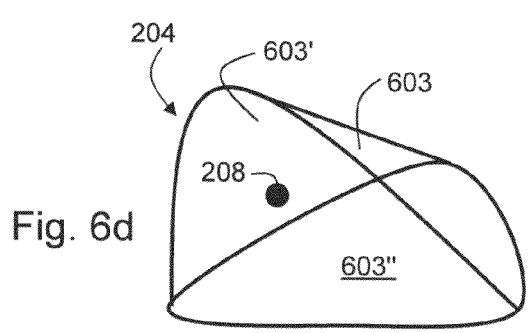
Figure 6E:
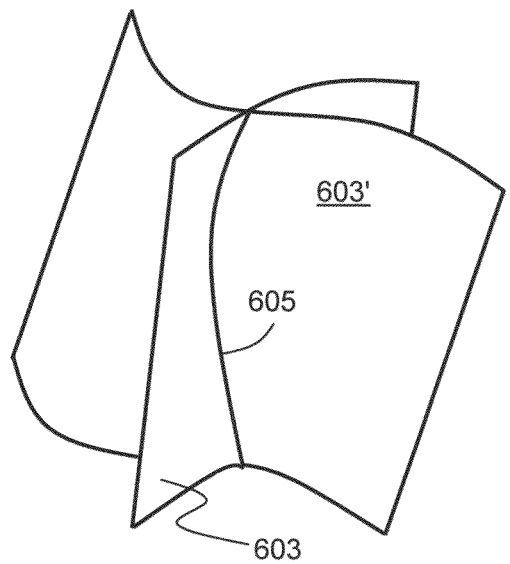
Figure 6F:
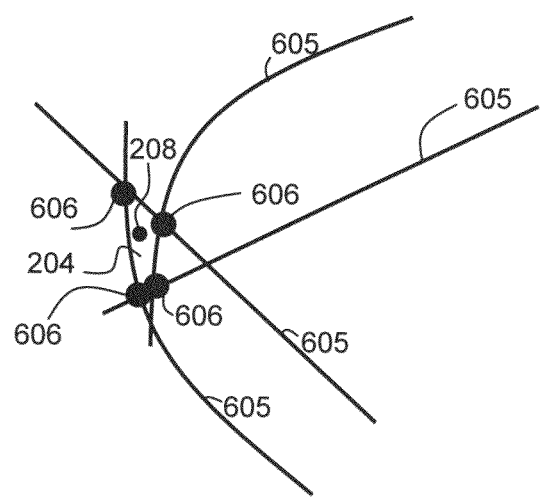
Figure 7:
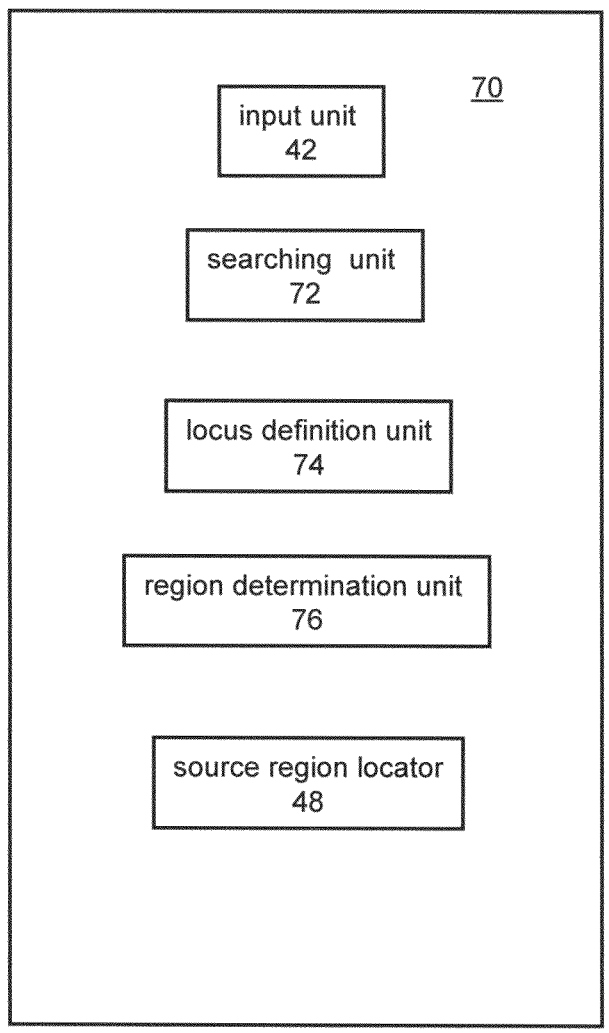
Figure 8:
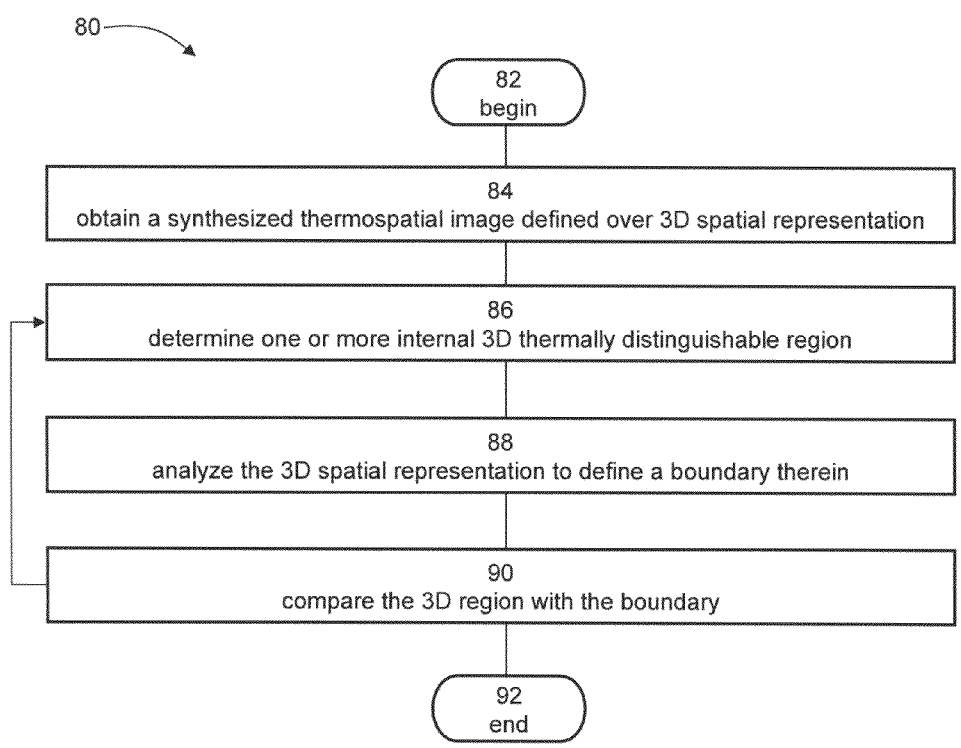
Figure 9A:
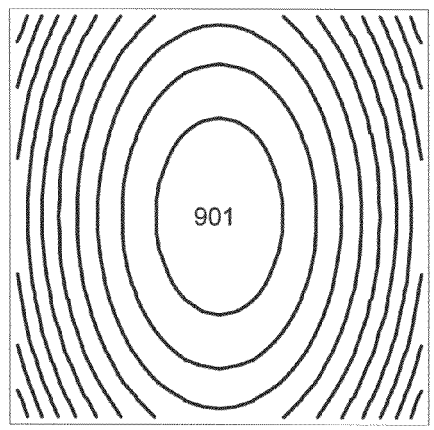
Figure 9B:
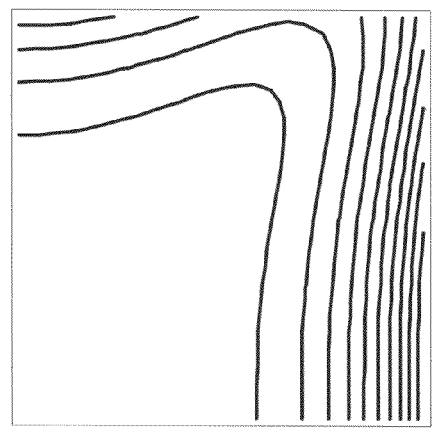
Figure 11:
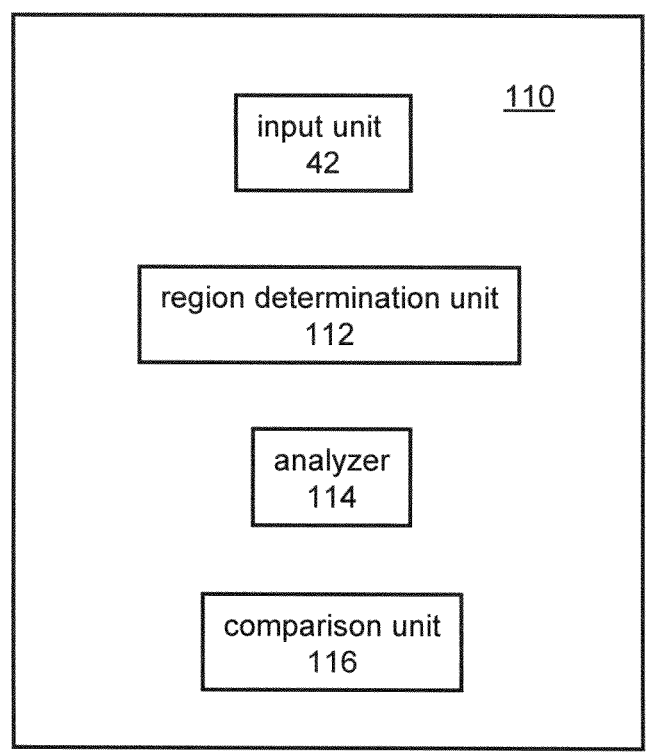
Figure 14:
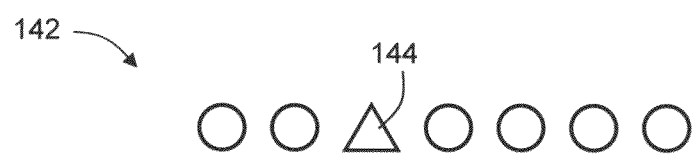
Figure 15:
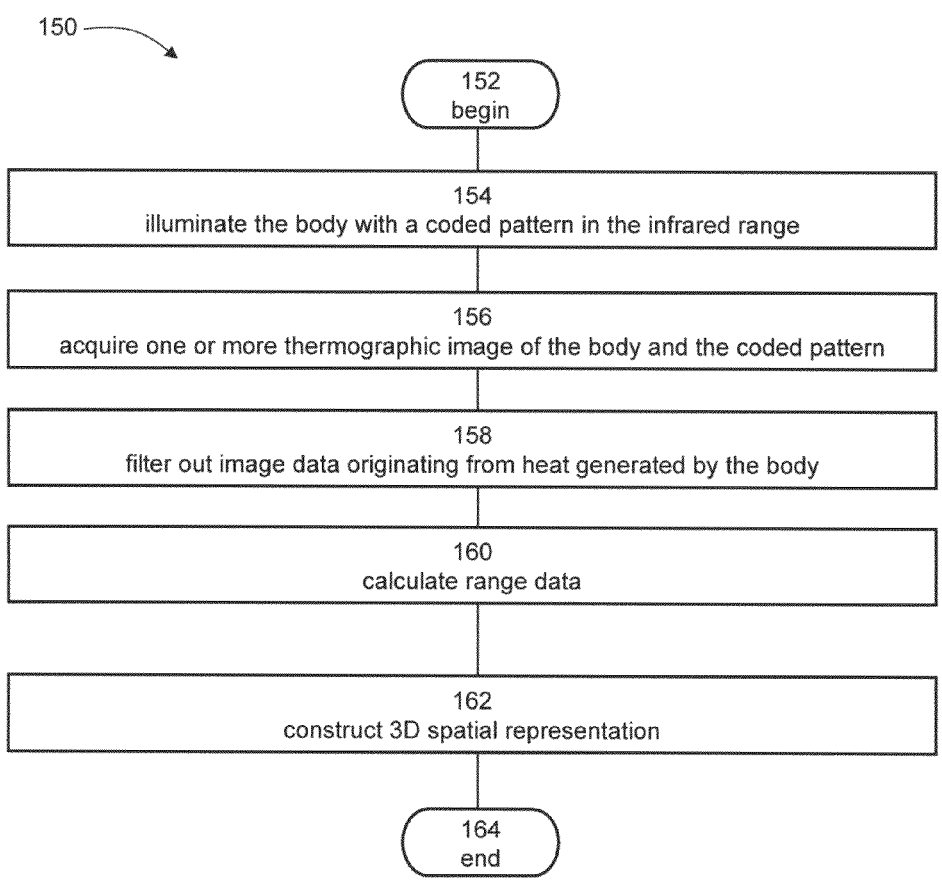
Figure 16A:
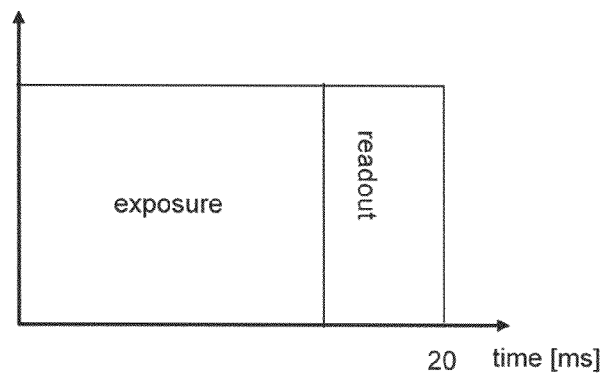
Figure 16B:
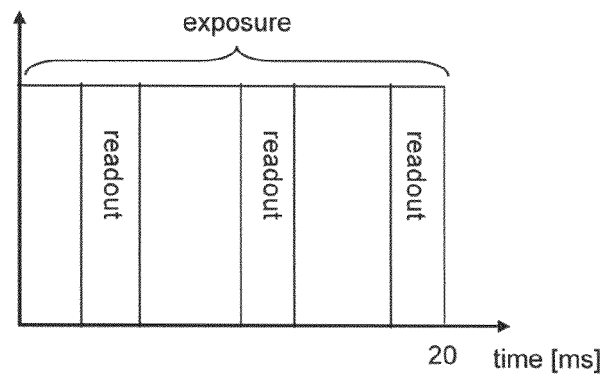
Figure 16C:
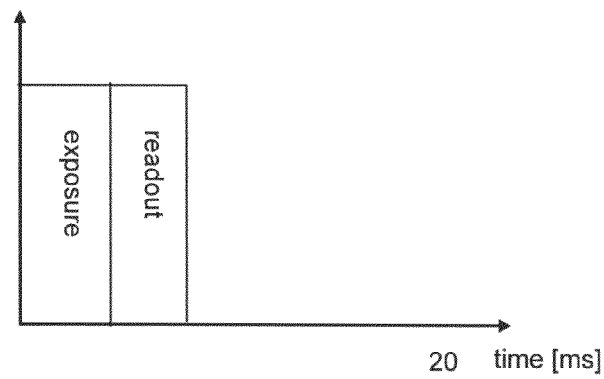
Figure 17:
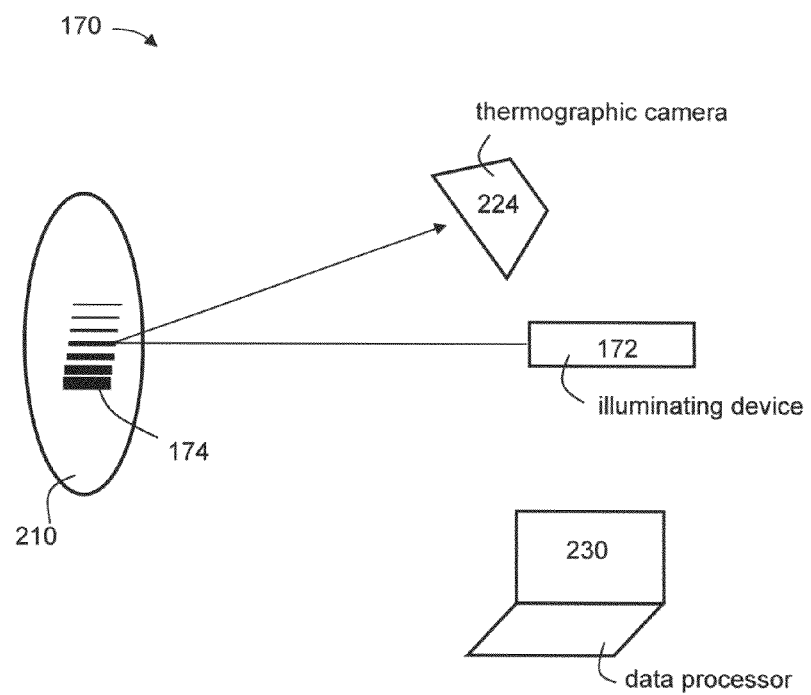
Figure 18A:
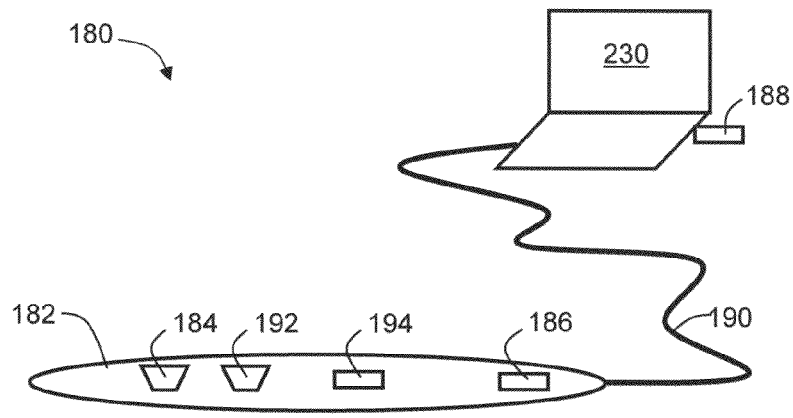
Figure 18B:
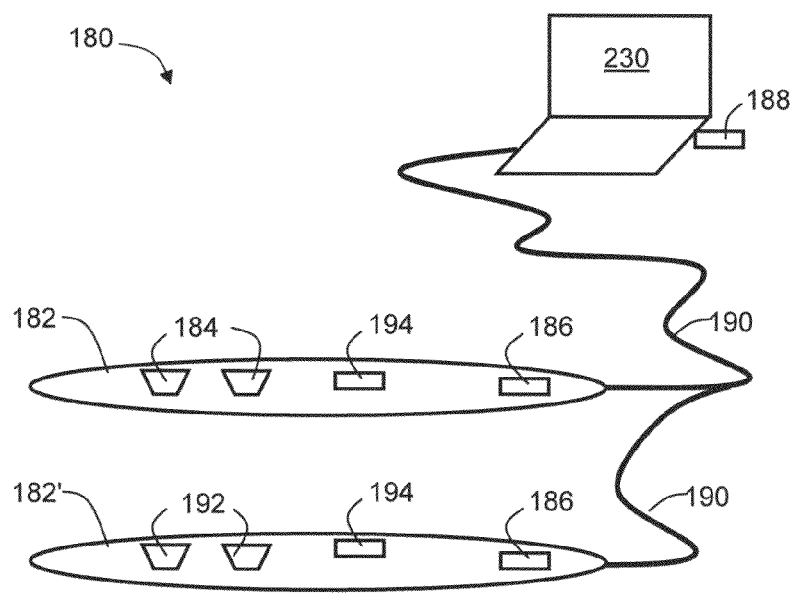
Figure 18C:
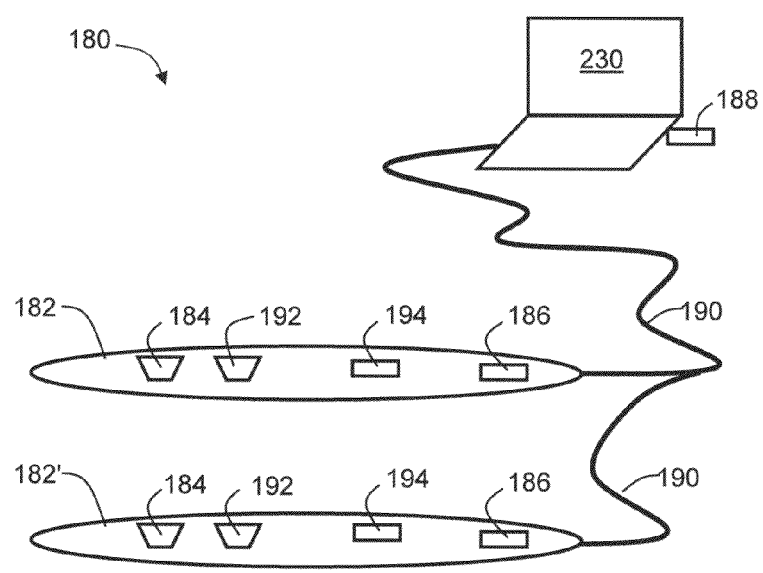
Figure 19A:
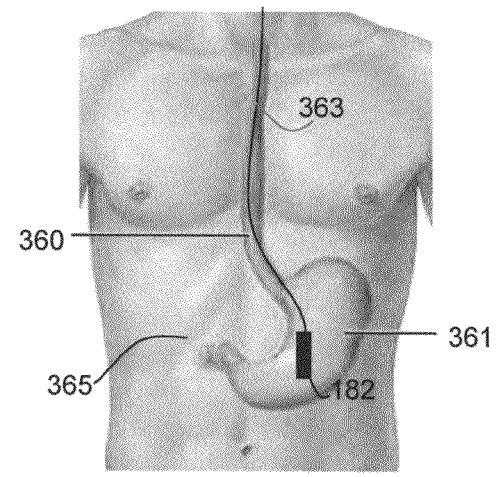
Figure 19B:
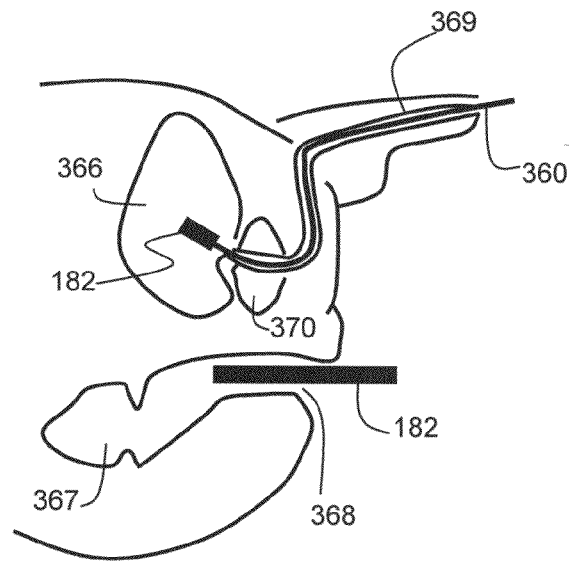
Figure 19C:
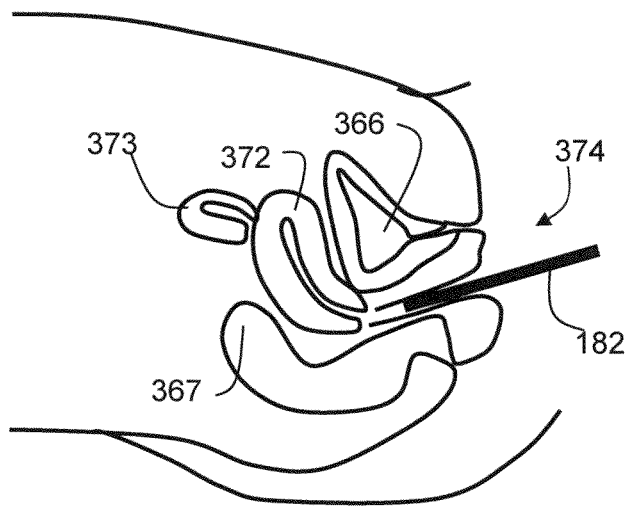
Figure 20:
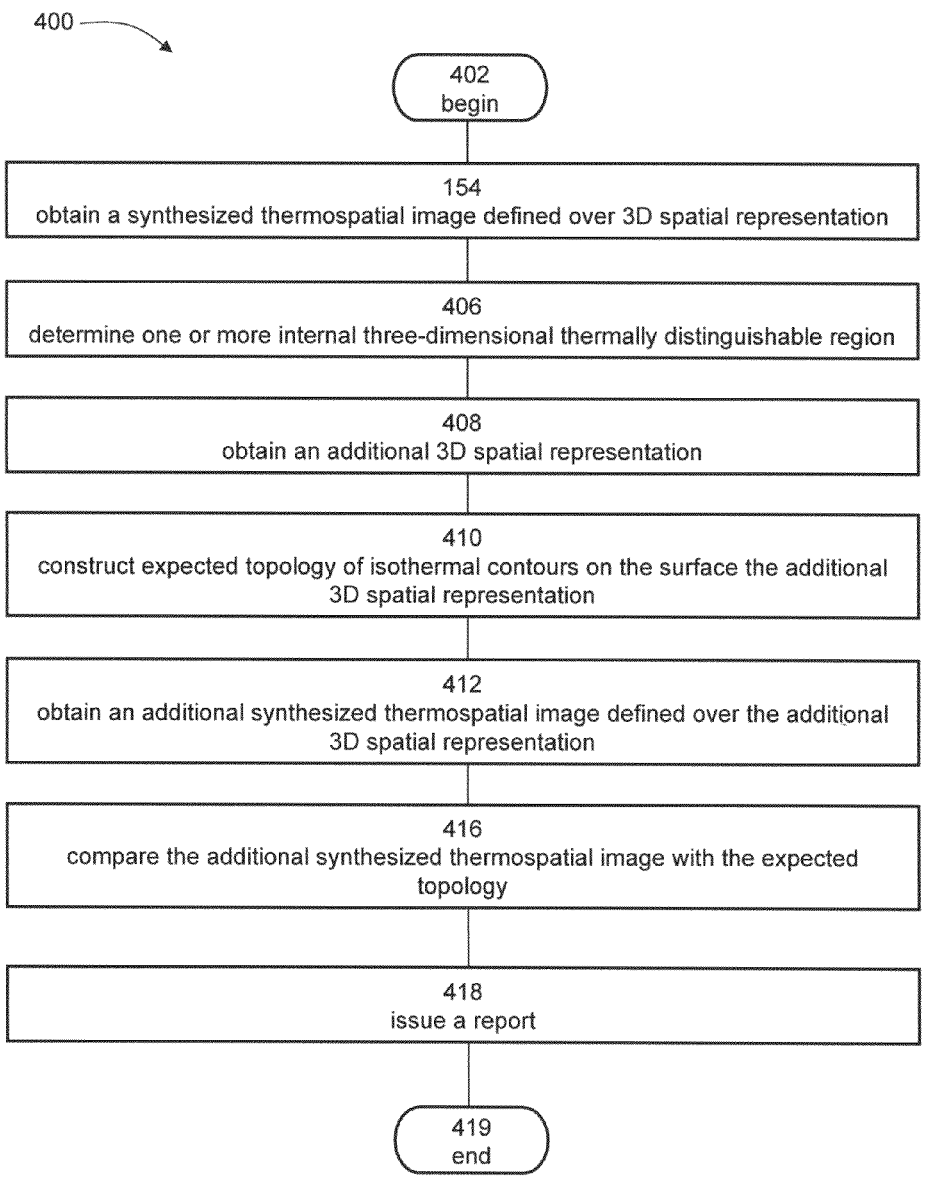
Figure 21:
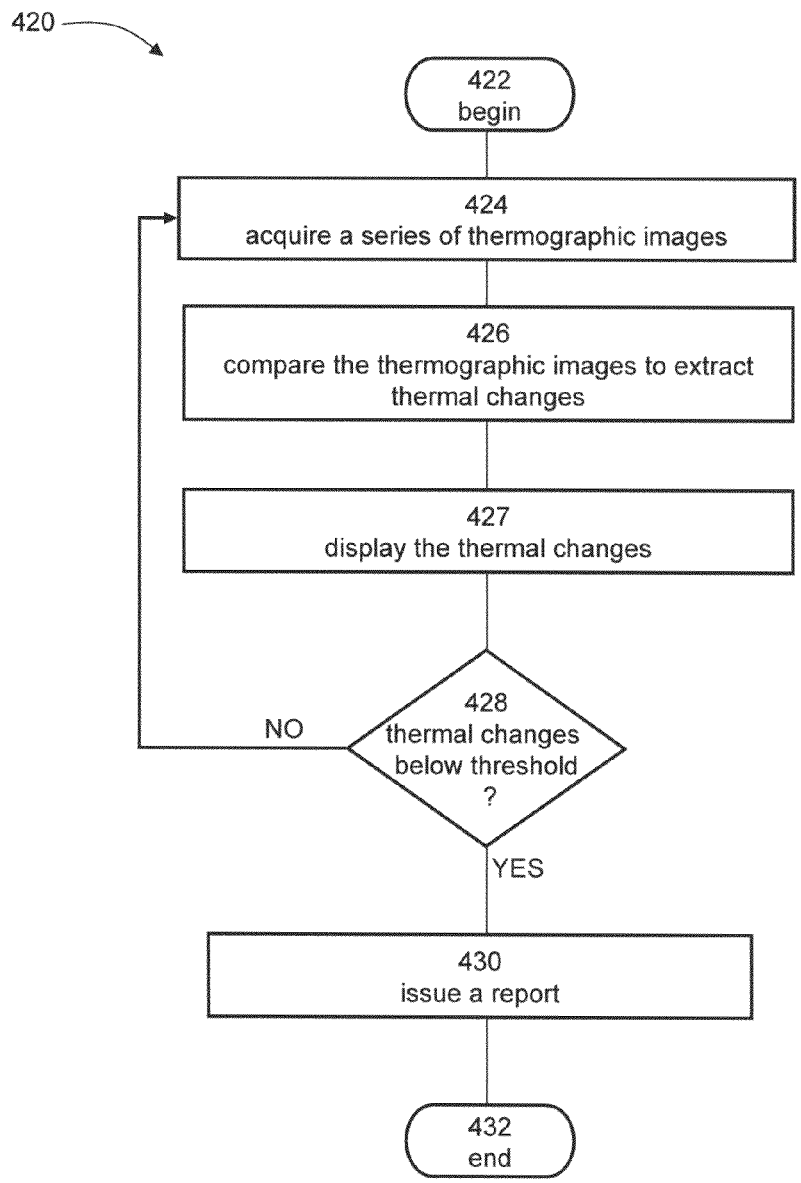
Figure 22:
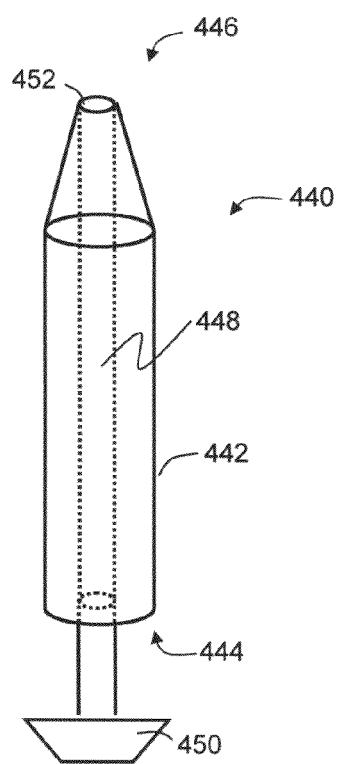
Figure 23A:
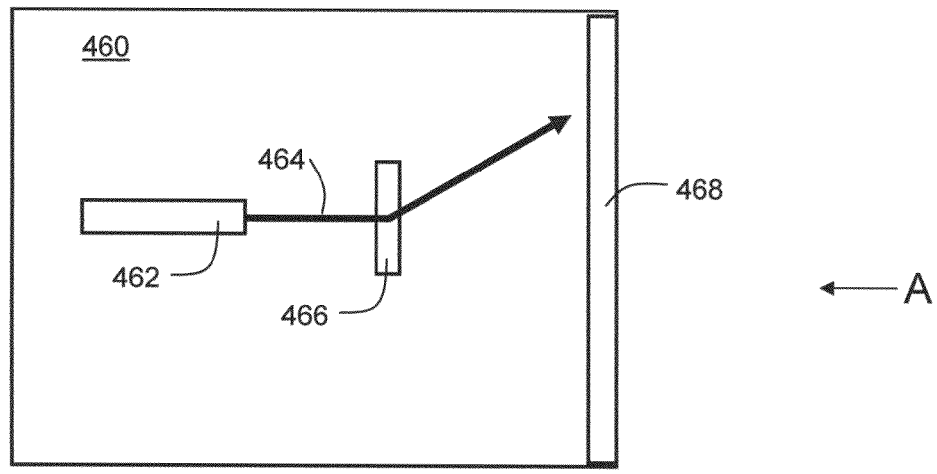
Figure 23B:
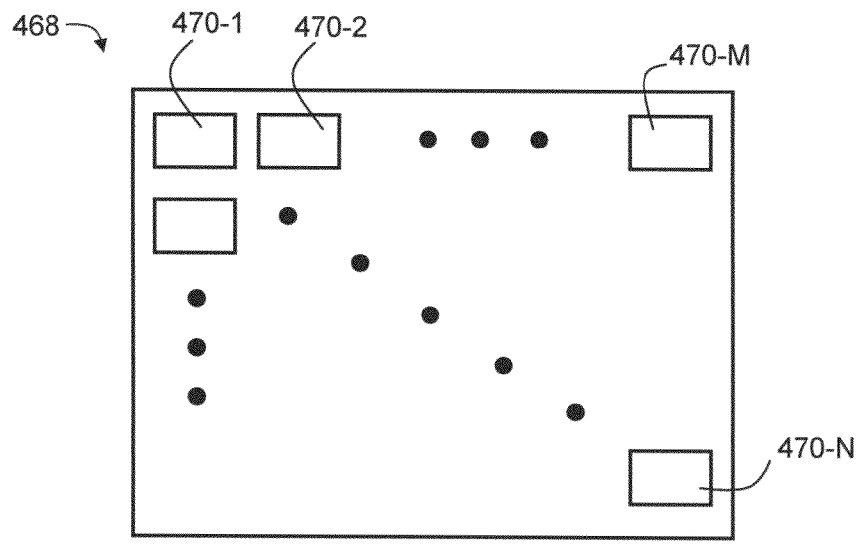
Figure 24:
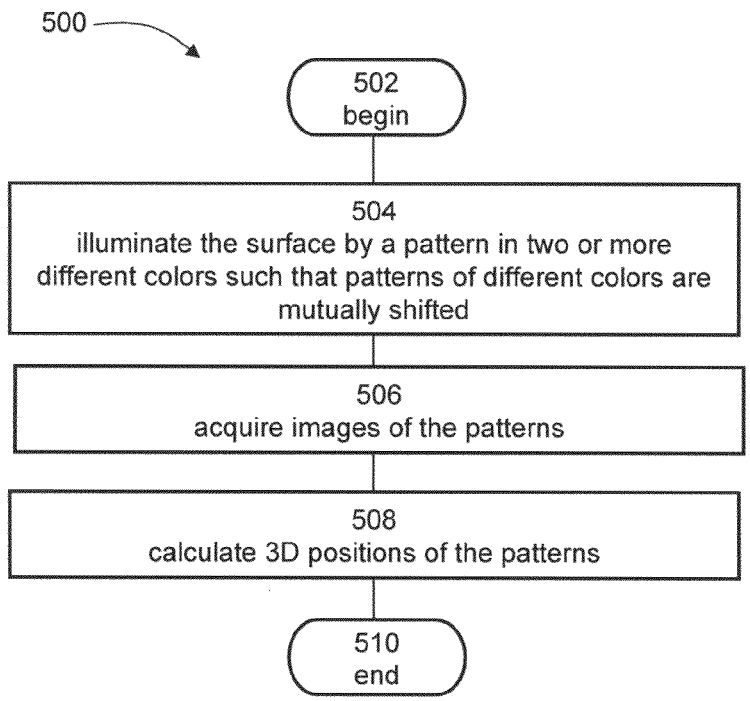
Figure 25:
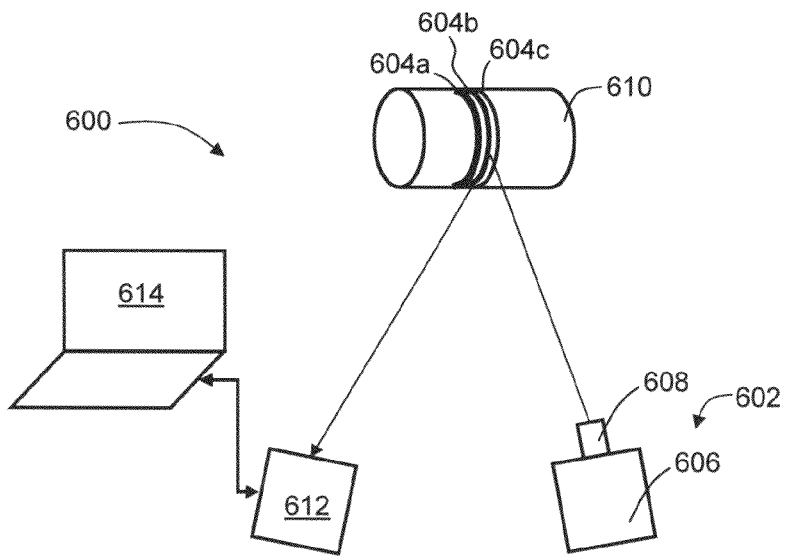
Figure 26A:
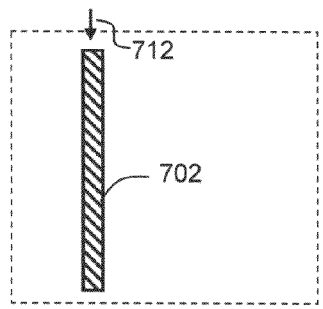
Figure 26B:
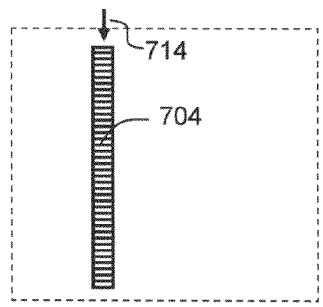
Figure 26C:
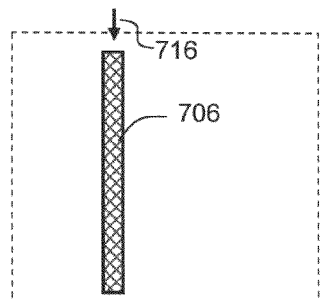
Figure 26D:
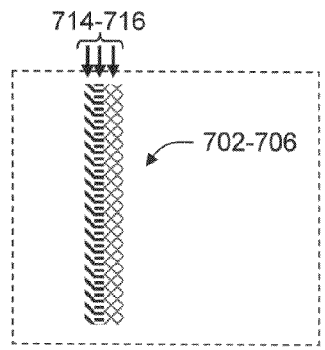

FIGS. 1a-c are schematic illustrations of a 3D spatial representation (FIG. 1a), a thermographic image (FIG. 1b), and a synthesized thermospatial image formed by mapping the thermographic image on a surface of the 3D spatial representation (FIG. 1c), according to various exemplary embodiments of the present invention;

FIG. 2 is a is a flowchart diagram describing a method suitable for calculating a thermal path in a living body, according to various exemplary embodiments of the present invention;

FIG. 3a is a schematic illustration of a procedure in which a gradient is used to define a thermal path in the body;

FIG. 3b is a schematic illustration of a procedure for determining the location of an internal three-dimensional thermally distinguishable region using two or more thermal trajectories;

FIG. 4 is a schematic illustration of an apparatus for calculating a thermal path in a living body, according to various exemplary embodiments of the present invention;

FIG. 5 is a flowchart diagram describing a method suitable for determining the position and optionally the size of an internal three-dimensional thermally distinguishable region in the living body, according to various exemplary embodiments of the present invention;

FIG. 6a is a schematic illustration of a procedure for defining a locus, according to various exemplary embodiments of the present invention;

FIGS. 6b-d are schematic illustrations three-dimensional regions which are bounded by several planar loci, according to various exemplary embodiments of the present invention;

FIG. 6e illustrates a line along which two loci intersect, according to various exemplary embodiments of the present invention;

FIG. 6f illustrates a plurality of points which are the intersection points of two or more lines, according to various exemplary embodiments of the present invention;

FIG. 7 is a schematic illustration of an apparatus for determining an internal three-dimensional thermally distinguishable region in the living body, according to various exemplary embodiments of the present invention;

FIG. 8 is a flowchart diagram of a method 80 suitable for determining a number of thermally distinguishable objects in the living body, according to various exemplary embodiments of the present invention;

FIGS. 9a-b are schematic illustrations of thermal data characterized by closed isothermal contours (FIG. 9a) and open isothermal contours (FIG. 9b), according to various exemplary embodiments of the present invention;

FIGS. 10a-e are schematic illustrations describing a procedure for defining a boundary within a 3D spatial representation, such that that points residing on one side of the boundary correspond to a single thermally distinguished spot on the surface of the 3D spatial representation, while points residing on another side of the boundary correspond to a plurality of thermally distinguished spots on the surface of the 3D spatial representation, according to various exemplary embodiments of the present invention;

FIG. 11 is a schematic illustration of apparatus for determining a number of thermally distinguishable objects in the living body, according to various exemplary embodiments of the present invention;

FIGS. 12a-f and 13a-e are schematic illustration of a thermospatial imaging system, according to various exemplary embodiments of the present invention;

FIG. 14 is a schematic illustration of illumination in the form of a series of spots, where at least one spot of the series is distinguishable from all other spots, according to various exemplary embodiments of the present invention;

FIG. 15 is a flowchart diagram of a method suitable for constructing a 3D spatial representation of a body, according to various exemplary embodiments of the present invention;

FIGS. 16a-c are schematic illustrations of exposure times and readout times, according to various exemplary embodiments of the present invention;

FIG. 17 is a schematic illustration of a system for constructing a three-dimensional spatial representation of a body, according to various exemplary embodiments of the present invention;

FIGS. 18a-c are schematic illustrations of a thermospatial imaging system, according to various exemplary embodiments of the present invention;

FIGS. 19a-c are schematic illustrations showing uses of an intracorporeal probe system according to various exemplary embodiments of the present invention;

FIG. 20 is a flowchart diagram of a method suitable for assessing the accuracy of the determination of the internal thermally distinguished regions in the body, according to various exemplary embodiments of the present invention;

FIG. 21 is a flowchart diagram of a method suitable for ensuring that a living body is at a generally stable thermal condition, according to various exemplary embodiments of the present invention;

FIG. 22 is a schematic illustration of medical device insertable into a living body, according to various exemplary embodiments of the present invention;

FIGS. 23a-b are schematic illustrations of an illuminating device suitable for thermospatial imaging, according to various exemplary embodiments of the present invention;

FIG. 24 is a flowchart diagram of another method suitable for constructing a 3D spatial representation of a body, in accordance with preferred embodiments of the present invention;

FIG. 25 is a schematic illustration of another system for constructing a 3D spatial representation of a body, in accordance with preferred embodiments of the present invention; and FIGS. 26a-d is a schematic illustration of mutually shifted patterns, according to various exemplary embodiments of the present invention.

DESCRIPTION OF THE PREFERRED EMBODIMENTS

The present embodiments comprise a method, apparatus and system which can be used in imaging. Specifically, but not exclusively the present embodiments can be used to determine the position of internal thermally distinguishable region in a living body.

The principles and operation of a method, apparatus and system according to the present embodiments may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present inventors have devised an approach which enables detection and localization of a tissue region of interest (e.g., a pathology such as a tumor) from the thermal path or trajectory leading from such a tissue region to a surface overlying the tissue region.

Several approaches for such trajectory or path calculations are contemplated herein. One such approach exploits a thermal data map which includes thermal data associated with a surface of at least a portion of the body. One or more thermally distinguishable region are identified in the thermal data map. In various exemplary embodiments of the invention the thermally distinguishable region(s) are then characterized in as far as surface distribution (e.g., pattern of thermal region), position on the surface, thermal intensity, size, position with respect to other thermally distinguishable regions. Such characterizing features are preferably utilized to calculate the thermal path in the body.

Thus, preferred embodiments of the invention relate generally to the analysis of surface information such as to extract properties of the underlying tissue. In various exemplary embodiments of the invention the surface information comprise spatial information as well as thermal information.

The spatial information comprises geometric properties of a non-planar surface which at least partially encloses a three-dimensional volume. Generally, the non-planar surface is a two-dimensional object embedded in a three-dimensional space. Formally, a non-planar surface is a metric space induced by a smooth connected and compact Riemannian 2-manifold. Ideally, the geometric properties of the non-planar surface would be provided explicitly for example, the slope and curvature (or even other spatial derivatives or combinations thereof) for every point of the non-planar surface. Yet, such information is rarely attainable and the spatial information is provided for a sampled version of the non-planar surface, which is a set of points on the Riemannian 2-manifold and which is sufficient for describing the topology of the 2-manifold. Typically, the spatial information of the non-planar surface is a reduced version of a 3D spatial representation, which may be either a point-cloud or a 3D reconstruction (e.g., a polygonal mesh or a curvilinear mesh) based on the point cloud. The 3D spatial representation is expressed via a 3D coordinate system, such as, but not limited to, Cartesian, Spherical, Ellipsoidal, 3D Parabolic or Paraboloidal coordinate 3D system. The term "surface" is used herein as an abbreviation of the term "non-planar surface".

The thermal information comprises data pertaining to heat evacuated from or absorbed by the surface. Since different parts of the surface generally evacuate or absorb different amount of heat, the thermal information comprises a set of tuples, each comprising the coordinates of a region or a point on the surface and a thermal value (e.g., temperature, thermal energy) associated with the point or region. The thermal information can be transformed to visible signals, in which case the thermal information is in the form of a thermographic image. The terms "thermographic image" and thermal information are used interchangeably throughout the specification without limiting the scope of the present invention in any way. Specifically, unless otherwise defined, the use of the term "thermographic image" is not to be considered as limited to the transformation of the thermal information into visible signals. For example, a thermographic image can be stored in the memory of a computer readable medium as a set of tuples as described above.

The surface information (thermal and spatial) of a body is typically in the form of a synthesized 3D image which includes both thermal data and spatial data on the same 3D image. Such image is referred to as a thermospatial image.

It is appreciated that a three-dimensional image of a body is typically a two-dimensional image which, in addition to indicating the lateral extent of body members, further indicates the relative or absolute distance of the body members, or portions thereof, from some reference point, such as the location of the imaging device. Thus, a three-dimensional image typically includes information residing on a non-planar surface of a three-dimensional body and not necessarily in the bulk. Yet, it is commonly acceptable to refer to such image as "three-dimensional" because the non-planar surface is conveniently defined over a three-dimensional system of coordinate. Thus, throughout this specification and in the claims section that follows, the terms "three-dimensional image" and "three-dimensional representation" primarily relate to surface entities.

The thermospatial image is defined over a 3D spatial representation of the body and has thermal data associated with a surface of the 3D spatial representation, and arranged gridwise over the surface in a plurality of picture-elements (e.g., pixels, arrangements of pixels) each represented by an intensity value or a grey-level over the grid. It is appreciated that the number of different intensity value can be different from the number of grey-levels. For example, an 8-bit display can generate 256 different grey-levels. However, in principle, the number of different intensity values corresponding to thermal information can be much larger. As a representative example, suppose that the thermal information spans over a range of 37° C. and is digitized with a resolution of 0.1° C. In this case, there are 370 different intensity values and the use of grey-levels is less accurate by a factor of approximately 1.4. Thus, in various exemplary embodiments of the invention the processing of thermal data is performed using intensity values rather than grey-levels. Yet the use of grey-level is not excluded from the scope of the present invention.

The term "pixel" is sometimes abbreviated herein to indicate a picture-element. However, this is not intended to limit the meaning of the term "picture-element" which refers to a unit of the composition of an image.

Typically, one or more thermographic images are mapped onto the surface of the 3D spatial representation to form the thermospatial image. The thermographic image to be mapped onto the surface of the 3D spatial representation preferably comprises thermal data which are expressed over the same coordinate system as the 3D spatial representation. Any type of thermal data can be used. In one embodiment the thermal data comprises absolute temperature values, in another embodiment the thermal data comprises relative temperature values each corresponding, e.g., to a temperature difference between a respective point of the surface and some reference point, in an additional embodiment, the thermal data comprises local temperature differences. Also contemplated, are combinations of the above types of temperature data, for example, the thermal data can comprise both absolute and relative temperature values, and the like.

Typically, the information in the thermographic image also includes the thermal conditions (e.g., temperature) at the reference markers.

The mapping of the thermographic image onto the surface of the 3D spatial representation is by accurately positioning the reference markers, for example (e.g., by comparing their coordinates in the thermographic image with their coordinates in the 3D spatial representation), to thereby match also other points hence to form the synthesized thermospatial image.

Optionally and preferably, the mapping of thermographic images is accompanied by a correction procedure in which thermal emissivity considerations are employed.

The thermal emissivity of a body member is a dimensionless quantity defined as the ratio between the amount of thermal radiation emitted from the surface of the body member and the amount of thermal radiation emitted from a black body having the same temperature as the body member. Thus, the thermal emissivity of an idealized black body is 1 and the thermal emissivity of all other bodies is between 0 and 1. It is commonly assumed that the thermal emissivity of a body is generally equal to its thermal absorption factor.

The correction procedure can be performed using estimated thermal characteristics of the body of interest. Specifically, the thermographic image is mapped onto a non-planar surface describing the body taking into account differences in the emissivity of regions on the surface of the body. A region with a different emissivity value compared to its surrounding, can be, for example, a scared region, a pigmented region, a nipple region on the breast, a nevus. Additionally, the emissivity values of subjects with different skin colors may differ.

In a preferred embodiment, the thermographic image is weighted according to the different emissivity values of the surface. For example, when information acquired by a thermal imaging device include temperature or energy values, at least a portion of the temperature or energy values can be divided by the emissivity values of the respective regions on the surface of the body. One of ordinary skill in the art will appreciate that such procedure results in effective temperature or energy values which are higher than the values acquired by the thermal imaging device. Since different regions may be characterized by different emissivity values, the weighted thermographic image provides better estimate regarding the heat emitted from the surface of the body.

A representative example of a synthesized thermospatial image for the case that the body comprise the breasts of a woman is illustrated in FIGS. 1a-c, showing a 3D spatial representation illustrated as a non-planar surface (FIG. 1a), a thermographic image illustrated as planar isothermal contours (FIG. 1b), and a synthesized thermospatial image formed by mapping the thermographic image on a surface of the 3D spatial representation (FIG. 1c). As illustrated, the thermal data of the thermospatial image is represented as grey-level values over a grid generally shown at 102. It is to be understood that the representation according to grey-level values is for illustrative purposes and is not to be considered as limiting. As explained above, the processing of thermal data can also be performed using intensity values. Also shown in FIGS. 1a-c, is a reference marker 101 used for the mapping.

The 3D spatial representation, thermographic image and synthesized thermospatial image can be obtained in any technique known in the art, such as the technique disclosed in International Patent Publication No. WO 2006/003658, U.S. Published Application No:20010046316, and U.S. Pat. Nos. 6,442,419, 6,765,607, 6,965,690, 6,701,081, 6,801,257, 6,201,541, 6,167,151, 6,167,151 and 6,094,198. The present embodiments also provide other techniques for obtaining the surface information or a part thereof as further detailed hereinunder.

Preferred embodiments of the invention can be embodied on a tangible medium such as a computer for performing the method steps. Preferred embodiments of the invention can be embodied on a computer readable medium, comprising computer readable instructions for carrying out the method steps. Preferred embodiments of the invention can also be embodied in electronic device having digital computer capabilities arranged to run the computer program on the tangible medium or execute the instruction on a computer readable medium. Computer programs implementing method steps of the present embodiments can commonly be distributed to users on a tangible distribution medium. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The present embodiments are useful in many medical and other applications.

For example, the present embodiments can be used for determining the presence, position and optionally size of internal tumors or inflammations, hence to aid, e.g., the diagnosis of cancer.

The present embodiments are also useful for constructing blood vessels map or for determining the location a specific blood vessel within the body because the temperature of the blood vessel is generally different from the temperature of tissue. In this respect, the present embodiments are also useful in the area of face recognition, because the knowledge of blood vessel positions in the face may aid in the identification of certain individuals. Recognition of other organs is also contemplated. Organ recognition using the present embodiments is particularly advantageous due to the ability of the present embodiments to localize thermally distinguishable regions in the living body. Such localization can be used for constructing blood vessel map which provides information regarding both orientation and depth of blood vessels in the body. The map can then be used for identifying individuals, e.g., by searching for similar map on a accessible and searchable database of blood vessel maps.

The present embodiments are also useful for bone imaging, because the temperature of bones is generally different from the temperature of soft tissue. This is particularly useful in medical conduction such as scoliosis and other spinal deformities in which it is required to regularly monitor the shape of the bones. In such and other conditions the present embodiments provide a safe substitute to the hazardous X-ray imaging.

Bone imaging can also be used for assessing the likelihood of osteoporosis symptoms. Specifically, since there is generally more heat in the anterior of a healthy bone than on the surface thereof, likelihood of bone mineral density reduction can be identified by monitoring temperature evolution of the bone surface. For example, a series of thermospatial image can be obtained and analyzed according to preferred embodiments of the present invention at certain intervals (e.g., once a month or the like) so as to determine whether or not the temperature on the surface of the bone consistently increases with time. The analysis can be used for assessing the likelihood of bone mineral density reduction, whereby more significant rate of temperature increase correspond to higher likelihood.

Referring now to the drawings, FIG. 2 is a flowchart diagram describing a method 10 suitable for calculating a thermal path in a living body. It is to be understood that, unless otherwise defined, the method steps described hereinbelow can be executed either contemporaneously or sequentially in many combinations or orders of execution. Specifically, the ordering of the flowchart diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

Method 10 can be used for determining a path on which a thermally distinguishable object resides within the body. A thermally distinguishable object is an object having a temperature which is higher or lower than the temperature of their immediate surroundings, and can be for example, an inflammation, a benign tumor, a malignant tumor and the like.

The method begins at step 12 and continues to step 14 in which a synthesized thermospatial image of the living body is obtained. The synthesized thermospatial image, as stated, is defined over a 3D spatial representation of the body and has thermal data associated with a surface of the 3D spatial representation. The thermospatial image can be generated by method 10 or it can be generated by another method or system from which the image can be read by method 10.

The method continues to step 16 in which one or more thermally distinguishable spots are identified in the thermospatial image. A "thermally distinguishable spot" refers to an area over the surface of the 3D spatial representation for which the thermal data associated therewith differ from the thermal data associated with the immediate surrounding of the region. For example, a thermally distinguishable spot can be an area at which the temperature reaches a local maximum or a local minimum. In the exemplified illustration of a thermally distinguishable spot is generally shown at 201 (see FIG. 1c). The size of the thermally distinguishable spot is typically much smaller than the size of the thermospatial image.

The method continues to step 18 in which a spatial gradient to the surface is calculated for at least a few thermally distinguishable spots. Calculations f spatial gradients are known in the art, and method form calculating such gradients are found in many textbooks. For example, when the 3D spatial representation is in the form of polygonal mesh, the spatial gradient can be a vector passing through the spot and directed perpendicularly to the respective polygon. For a point cloud or other types of 3D representations, the gradient can be found by means of first spatial derivatives, or by means of tangential planes. Once the gradient is calculated, it is preferably used, together with the location of the spot, to define a straight line which can be the thermal path in the body. For example, when the living body includes a hot object, such as a method 10 is used for determining a path on which a thermally distinguishable object such as an inflammation or a tumor, the straight line can be define as a path along which heat propagates in the body.

The procedure is illustrated in FIG. 3a, showing thermally distinguished spot 201 on a surface 205 of the 3D spatial representation 206. A gradient 202 points inward the 3D spatial representation and a path 203 is defined as a straight line parallel to gradient 202 and passing through spot 201. Also shown is the location of internal three-dimensional thermally distinguishable region in the living body as represented by an internal region 204 in representation 206. As shown, path 203 also passes through region 204. Once found, the path is preferably displayed or recorded on a tangible medium, such as a display device, a hard copy a memory medium.

In various exemplary embodiments of the invention the method continues to step 22 in which two or more thermal trajectories are used to determine the location of an internal three-dimensional thermally distinguishable region in the living body. This procedure is illustrated in FIG. 3b, showing also a second 203', corresponding to a second spot 201' and a second gradient 202'. The location of region 204 can be obtained by calculating the intersection between the two trajectories, or, when the trajectories do not intersect, as the region between the closest points of the trajectories. Once found, the internal three-dimensional thermally distinguishable region is preferably displayed or recorded on a tangible medium. Preferably, the method continues to step 24 in which a source region 208 is located within region 204. The source region corresponds to the location of a thermally distinguished object within the body (e.g., an inflammation, a tumor) and can be located by any mathematical procedure known in the art, including, without limitation, a centroid, a weighted centroid and a center-of-mass of region 204.

According to a preferred embodiment of the present invention the method loops back to step 14 in which an additional thermospatial image is obtained, which additional thermospatial image corresponds to a different posture of the living body. For example, when the living body is the breast of a woman, the first thermospatial image can describe the breast when the woman is standing and the additional thermospatial image can describe the breast when the woman bends forwards or lying in prone position. Preferably, but not obligatorily, the additional thermospatial image is obtained such that the two or more thermospatial images alignable with respect to a predetermined fixed reference point on the body. For example, the reference point can be a mark on the arm-pit. The identification of the thermally distinguishable spot(s) and the calculation of the gradient(s) is preferably repeated for the additional thermospatial image, so as to determine the location of the internal three-dimensional thermally distinguishable region when the body is in the second posture. The locations determined in the different postures can then be compared to assess the accuracy of the procedure. A report regarding the assessed accuracy can then be issued, e.g., on a display device, a hard copy or the like.

Alternatively, the locations can be averaged and the average location of the internal three-dimensional thermally distinguishable region can be displayed or recorded on a tangible medium.

Method 10 ends at step 26.

FIG. 4 is a schematic illustration of an apparatus 40 for calculating a thermal path in a living body, according to various exemplary embodiments of the present invention. Apparatus 40 can be used for executing one or more of the method steps of method 10.

Apparatus 40 comprises an input unit 42 which receiving the synthesized thermospatial image, a spot identification unit 44 which identifies the thermally distinguishable spot(s), and a gradient calculator 46 for calculating the spatial gradient as further detailed hereinabove. Apparatus 40 optionally and preferably comprises a region determination unit 48 which is designed and configured for determining an internal three-dimensional thermally distinguishable region as further detailed hereinabove. Apparatus 40 can also comprise a source region locator 48 which locates the source region as further detailed hereinabove.

Reference is now made to FIG. 5 which is a flowchart diagram of a method 50 suitable for determining the position and optionally the size of an internal three-dimensional thermally distinguishable region in the living body, according to various exemplary embodiments of the present invention.

The method begins at step 52 and continues to step 54 in which a synthesized thermospatial image is obtained. The thermospatial image can be generated by method 50 or it can be generated by another method or system from which the image can be read by method 50.

The method continues to step 56 in which the surface, or more specifically, the grid 102 is searched for one or more sets of picture-elements represented by generally similar intensity values. Formally, the grid is searched for a set of picture-elements having in intensity value of from $I-\Delta I$ to $I+\Delta I$, where, $I$ is a predetermined intensity characterizing the set and $\Delta I$ is a width parameter. The value of $\Delta I$ is preferably selected as small as possible but yet sufficiently large to allow collection of a sufficient number of picture-elements (say, more than 10 picture-elements) in the set. For example, when the intensity value in each picture-element is a number from 0 to 255, $\Delta I$ can be about 10 units of intensity.

As used herein the term "about" refers to ±20%.

When more than one sets of picture-element are defined, each set is characterized by a different intensity I, but two sets may or may not have equal width parameters.

The search for sets of picture-elements represented by generally similar intensity values can also be accompanied by an averaging procedure. For example, the search can begin by locating a thermally distinguished spot or region on the surface. The intensity values of pixels or picture-elements in the located spot or region are then averaged or weighted averaged to provide an average intensity value. The method can then search for other regions or spots having the same or similar average intensity value. If no matches are found, the method optionally and preferably recalculates the average intensity value using the picture-element in the thermally distinguished region and picture-element surrounding the region, hence expanding the region. The method can then search for other regions using the new average. This process can be iterated a few times as desired. Thus, in this embodiment, the set is characterized by the average intensity value.

The method continues to step 58 in which a plurality of loci are defined for one or more of the sets of picture-elements. Each locus of the plurality of loci is associated with at least a pair of picture-elements of the set and defined such that each point of the locus is at equal thermal distances from individual picture-elements of the pair. The procedure is illustrated in FIG. 6a, which is a fragmentary view showing a cross section of surface 205 and pair of picture-elements 601 and 602 having generally similar intensity values (hence belonging to the same set). A locus 603 of points is associated with points 601 and 602. A distance $d_1$ defined between a point 604 of locus 603 and point 601 equals a distance $d_2$ defined between the same point 604 of locus 603 and point 602. Generally, the distances $d_1$ and $d_2$ are determined from the standpoint of a thermal distance based on thermal conductivity rather than from the standpoint of a geometrical distance. Yet, in some embodiments the body can be modeled as a thermally isotropic medium in which case the definition of a thermal distance coincides with the definition of geometric distance.

Locus 603 can have any shape either planar or non planar. It is appreciated that when the distances $d_1$ and $d_2$ are geometrical distances, locus 603 is a plane. Each pair of points may, in principle, be associated with a different locus. Thus, when the set includes more than one pair of points, a plurality of loci is defined. Once the loci are defined the method continues to step 60 in which the loci are used to define the internal three-dimensional thermally distinguishable region. This can be done in more than one way. In one embodiment, the internal region is fully or partially bounded by the loci. In other words, the loci are used for defining the external surface of the region. This embodiment is illustrated in FIGS. 6b-d, showing examples of three-dimensional regions 204 bounded by several planar loci, designated by reference signs 603, 603', 603".

In another embodiment, the internal region is determined based on intersecting lines of two or more of the loci. This embodiment is illustrated in FIG. 6e-f, showing a line 605 along which two loci 603 and 603' intersect (FIG. 6e), and a plurality of points 606 which are the intersection points of two or more lines 605 (FIG. 6f). Points 606 can then be used to define region 204, e.g., by considering points 606 as a point-cloud or by reconstructing region 204 as a polygonal or curvilinear mesh.

When the method finds more then one set of picture-elements in step 56, the loci of at least some of the sets are independently used to define an internal region associated with the respective set. The final internal region can then be defined, for example, by averaging the regions. The average can be weighted using the intensities associated with the sets as relative weights for the respective regions. Alternatively, the final region can be defined as the union of all regions. Still alternatively, the final region can be defined as the intersection of two or more regions.

According to a preferred embodiment of the present invention the method loops back to step 54 in which one or more additional thermospatial image is obtained, which additional thermospatial image corresponds to a different posture of the living body. Preferably, but not obligatorily, the additional thermospatial image is obtained such that the two or more thermospatial images alignable with respect to a predetermined fixed reference point on the body. The search for set(s) of picture-elements and the definition of loci is preferably repeated for the additional thermospatial image, so as to determine the location of the internal three-dimensional thermally distinguishable region when the body is in the second posture. The locations determined in the different postures can then be compared to assess the accuracy of the procedure. A report regarding the assessed accuracy can then be issued, e.g., on a display device, a hard copy or the like.

Alternatively, the locations can be averaged and the average location of the internal three-dimensional thermally distinguishable region can be displayed or recorded on a tangible medium.

Once found, region 204 is preferably displayed or recorded on a tangible medium. Preferably, the method continues to step 62 in which a source region 208 is located within region 204. The source region corresponds to the location of a thermally distinguished object within the body (e.g., an inflammation, a tumor) and can be located by any mathematical procedure known in the art, including, without limitation, a centroid, a weighted centroid and a center-of-mass of region 204.

Method 50 ends at step 64.

Following is a representative example of an algorithm for the definition of loci and the determination of the internal region based on the loci, in the embodiment in which the distances $d_1$ and $d_2$ are geometric distances and each locus is a plane.

A set of all pixels having similar intensity values from $I-\Delta I$ to $I+\Delta I$ is denoted s. In Cartesian coordinate system, two pixels in s are denoted $p_1=[x_1\ y_1\ z_1]^T$ and $p_2=[x_2\ y_2\ z_2]^T$. The Euclidian norms of these pixels are denoted $\|p_1\|^2$ and $\|p_2\|^2$, respectively. The locus of all points which are equidistant from $p_1$ and $p_2$ is a plane perpendicular to the vector $p_1-p_2=[x_1-x_2, y_1-y_2, z_1-z_2]^T$. The equation of such plane is:

$$2[p_1-p_2]^T \cdot \begin{bmatrix} x \\ y \\ z \end{bmatrix} = \|p_1\|^2 - \|p_2\|^2. \tag{EQ. 2}$$

which can also be written as:

$$2(x_1-x_2)x+2(y_1-y_2)y+2(z_1-z_2)z=\|p_1\|^2-\|p_2\|^2 \tag{EQ. 1}$$

The equations of all such planes are concatenated by the algorithm to provide a linear least square problem:

$$A \cdot \begin{bmatrix} x \\ y \\ z \end{bmatrix} \approx b, \tag{EQ. 3}$$

where A and b are arrays which include all vectors $2(p_i-p_j)$ and all norm differences $\|p_i\|^2-\|p_j\|^2$, respectively, for any pair of pixels $p_i, p_j \in s$. The solution of the linear least square problem is:

$$(A^T A)^{-1} A^T b. \tag{EQ. 4}$$

The algorithm is described by the following pseudo code:
1. Find the unique gray-level values on the surface.
2. Initialize A and b as an empty arrays.
3. For each gray-level:
   (a) Find all the pixel pairs which share the same intensity value (from $I-\Delta I$ to $I+\Delta I$). Each pair defines a plane, which consist of all the points with equal distances from the two pixels of the pair. Construct the equation of the plane (Equations 1 or 2).
   (b) Discard all the pairs which are too close to each other.
   (c) Concatenate the vector $2 \cdot (p_1-p_2)$ to array A.
   (d) Concatenate the scalar $\|p_1\|^2-\|p_2\|^2$ to array b.
4. Solve the least square equation $Ax \approx b$, (Equation 4).
5. End The complexity of the problem is $O(n^2)$, where n is the size of s, both for selecting all pairs of s and for solving the corresponding least square problem. For example, for a paraboloid of 41×41 pixels, the position of the source was determined with an accuracy of (0.006, 0.006, 0.009), and calculation time of 0.03 seconds on an IBM ThinkPad R50e, equipped with an Intel® Pentium®M 1.70 GHz processor and 599 MHz 504 Mb of RAM.

FIG. 7 is a schematic illustration of an apparatus 70 for determining an internal three-dimensional thermally distinguishable region in the living body, according to various exemplary embodiments of the present invention. Apparatus 70 can be used for executing one or more of the method steps of method 50.

Apparatus 70 comprises input unit 42 for receiving the synthesized thermospatial image, a searching unit 72 which searches over the grid for one or more sets of picture-element represented by generally similar intensity values, a locus definition unit 74 which define the loci, and a region determination unit 76 for determining internal region 204 three-dimensional thermally distinguishable region based on the loci as further detailed hereinabove. Apparatus 70 can also comprise source region locator 48 as further detailed hereinabove.

Reference is now made to FIG. 8 which is a flowchart diagram of a method 80 suitable for determining a number of thermally distinguishable objects in the living body, according to various exemplary embodiments of the present invention.

The method begins at step 82 and continues to step 84 in which a synthesized thermospatial image is obtained. The thermospatial image can be generated by method 80 or it can be generated by another method or system from which the image can be read by method 80. It is appreciated that when thermal data are transformed to visible image, the image is generally in the form of isothermal contours. Broadly speaking, the isothermal contours can be closed or they can be open. For example, when the thermal data include temperature levels, the existence of closed isothermal contours typically indicates that the temperature has one or more local extrema in the area surrounded by the closed contours, while the existence of open isothermal contours typically indicates that the temperature is monotonic (including the case of a saddle point) in the area of the open contours. For example, when a heat source is not within the field-of-view with the imaging device, the isothermal contours are generally open.

Representative examples of thermal data characterized by closed isothermal contours and open isothermal contours are provided in FIGS. 9a-b, respectively. As shown, in FIG. 9a, the closed isothermal contours surround at least one thermally distinguished spot 901, while no such spot exists in FIG. 9b where the isothermal contours are open.

In various exemplary embodiments of the invention, the thermal data of the thermospatial image obtained in step 84 is characterized by closed isothermal contours which surround at least one thermally distinguished spot on the surface of the 3D spatial representation.

The method continues to step 86 in which the position and optionally the size of one or more internal three-dimensional thermally distinguishable regions in the living body are determined. This can be done using method 10, method 50 or any other method. Also contemplated is a combination between methods (e.g., methods 10 and 50). Optionally and preferably, the method also determines one or more source regions as described hereinabove.

Method 80 continues to step 88 in which the 3D spatial representation is analyzed so as to define a boundary within the spatial representation. The boundary is defined such that points residing on one side of the boundary correspond to a single thermally distinguished spot on the surface, while points residing on another side of the boundary correspond to a plurality of thermally distinguished spots on the surface.

Step 88 may be better understood may with reference to FIGS. 10a-d and the following description.

Figure 10A:
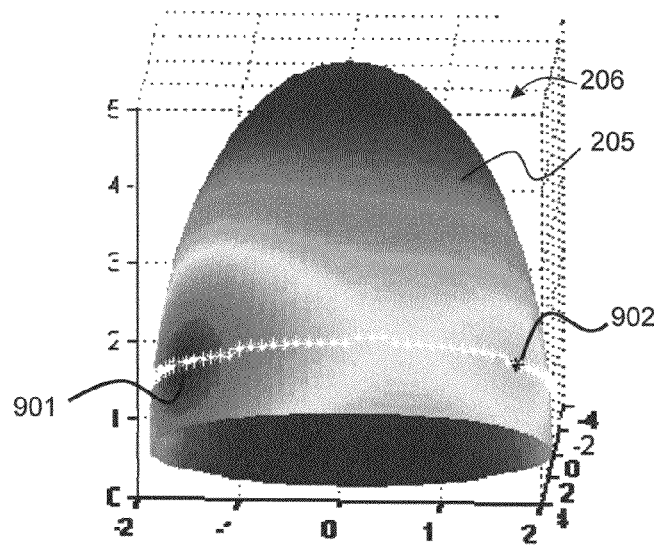
Figure 10B:
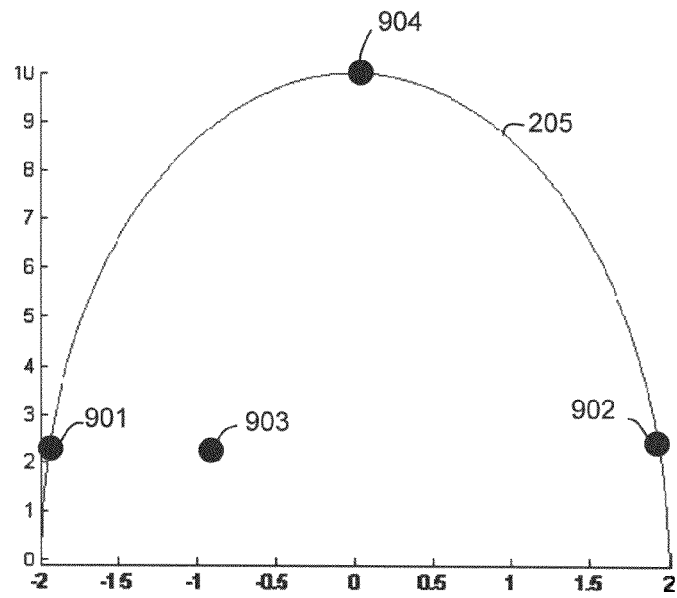

FIG. 10a is a schematic illustration of a thermospatial image with thermal data on surface 205 of 3D spatial representation 206. There are two thermally distinguished spots 901 and 902 on surface 205, each being identifiable as being surrounded by closed thermal contours. FIG. 10b schematically illustrates a cross sectional view of 3D spatial representation 206 corresponding to the thermospatial image of FIG. 10a. Shown in FIG. 10b are spots 901 and 902 on surface 205 and an internal thermally distinguished source point 903 in the bulk.

From the standpoint of a distance function D describing thermal distances between source point 903 and various points on surface 205, spots 901 and 902 comprise local minima of D. That is to say, the thermal distance between source point 903 and spot 901 is smaller than any thermal distance between source point 903 and points on surface 205 in the immediate vicinity of spot 901; and the thermal distance between source point 903 and spot 902 is smaller than any thermal distance between source point 903 and points on surface 205 in the immediate vicinity of spot 902. Also shown in FIG. 10b, is a surface point 904 corresponding to global maximum.

Figure 10C:
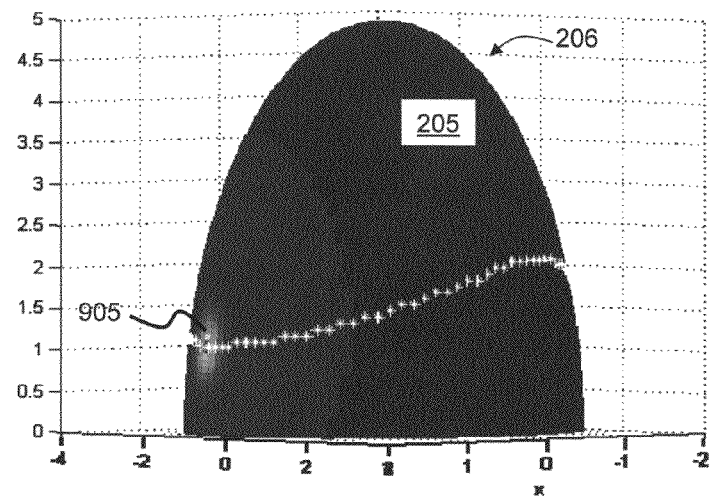
Figure 10D:
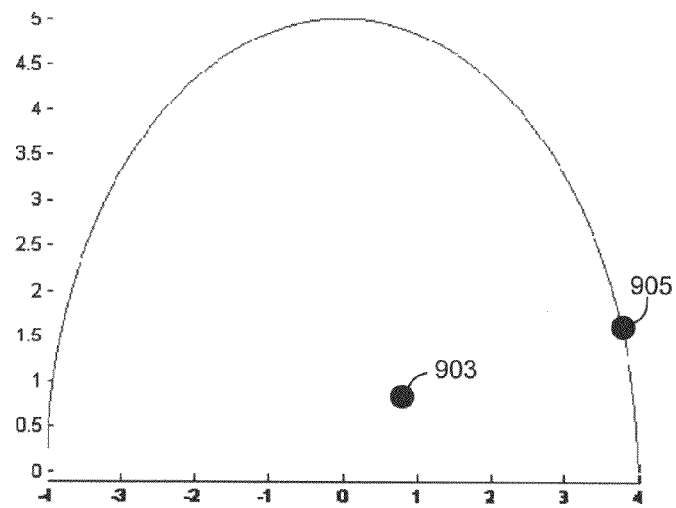

A different situation is illustrated in FIGS. 10c-d. FIG. 10c is a schematic illustration of a thermospatial image (with closed thermal contours) having a single thermally distinguished spot 905 on surface 205. FIG. 10d is a schematic illustration of a cross sectional view of surface 205, which correspond to the thermospatial image of FIG. 10c. Shown in FIG. 10b is spot 905 and source point 903 in the bulk. From the standpoint of the distance function D, spot 905 is a local minimum of D. However, unlike the situation presented in FIGS. 10a-b above, there is only one local minimum in FIGS. 10c-d.

Figure 10E:
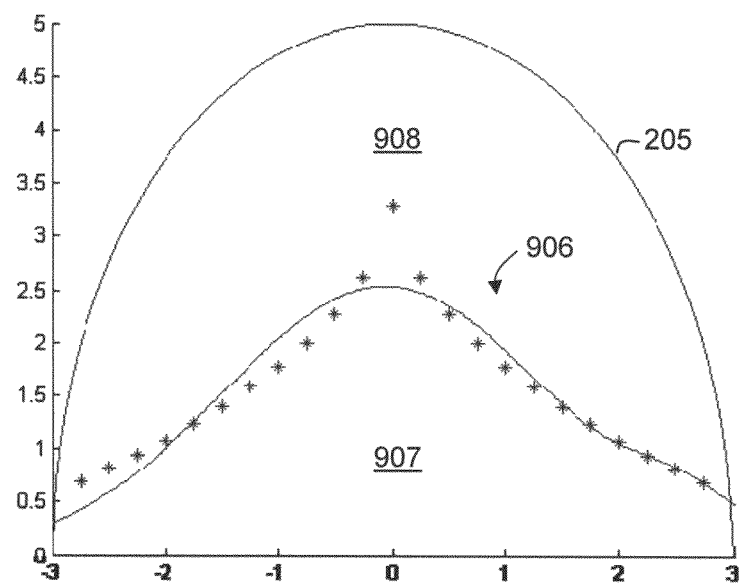

In principle, for a given surface 205 the number of local minima of the distance function D depends on the position of source point 903 in the bulk. In various exemplary embodiments of the invention the method analyzes surface 205 and defines a boundary between all the possible positions of source point 903 for which D has a single minimum and all the possible positions of source point 903 for which D has more than one minimum. A representative illustration of such boundary is illustrated in FIG. 10e, showing a boundary 906 which divides the bulk into two sections 907 and 908 whereby the lower section 907 includes all possible positions of source point 903 for which D has two minima and the upper section 908 includes all possible positions of source point 903 for which D has a single minimum. Boundary 906 can be provided either in the form of a point-cloud or in a form of reconstructed surface approximating the point-cloud. The point-cloud is illustrated in FIG. 10e as asterisks and the reconstructed surface is illustrated as a solid line.

Once boundary 906 is found, method 80 continues to step 90 in which the internal region(s) and/or the source region(s) found in step 86 are compared against boundary 906. Specifically, the method determines, for each internal region, on which side of boundary 906 it resides. Such comparison allows method 80 to determine the number of thermally distinguished objects in the living body, as will be understood from the following simplified examples.

Hence, suppose that the thermospatial image obtained in step 84 includes two thermally distinguished spots (cf. FIG. 10a). Suppose further that in step 86 the method identifies an internal source region located within section 908. Since it is expected that when a source region is located in section 908 there will be only one thermally distinguished spot on surface 205, the method can determine that the two thermally distinguished spots on surface 205 correspond to two different thermally distinguished objects in the bulk. On the other, if the thermospatial image obtained in step 84 includes a single thermally distinguished spot (cf. FIG. 10c), and the method identifies an internal source region located within section 908, the method can determine that the identified internal source region correspond to a single thermally distinguished object in the bulk with no other such objects. The comparison can also serve for estimating the accuracy of step 86. For example, suppose that the thermospatial image obtained in step 84 includes one thermally distinguished spot (cf. FIG. 10c), and that in step 86 the method identifies an internal source region located within section 907. Since it is expected that when a source region is located in section 907 there will be two thermally distinguished spots on surface 205, the method can determine that the accuracy of the procedure performed in step 86 is insufficient and issue a report or signal the operator regarding such inaccuracy. Alternatively or additionally, the method can loop back to step 86 and determine the position and/or size of the source region using another procedure or using the same procedure but with increased accuracy (e.g., using more sampled points for the reconstruction of the 3D spatial representation 206).

Method 80 ends at step 92.

FIG. 11 is a schematic illustration of an apparatus 110 for determining a number of thermally distinguishable objects in the living body, according to various exemplary embodiments of the present invention. Apparatus 110 can be used for executing one or more of the method steps of method 80.

Apparatus 110 comprises input unit 42 for receiving the synthesized thermospatial image and a region determination unit 112 which determines the internal 3D thermally distinguishable region and optimally the internal source region. Unit 112 may comprise selected components of apparatus 40 (e.g., unit 44, calculator 46, unit 46, locator 48) and/or apparatus 70 (e.g., unit 72, unit 74, unit 76) and may perform selected steps of method 10, method 50 or combination thereof. Apparatus 110 may also receive the internal region(s) from apparatus 40 or 70.

Apparatus 110 further comprises an analyzer 114 which analyzes the 3D spatial representation and defines boundary 906 as described above, and a comparison unit 116 which compares the internal 3D thermally distinguishable region with boundary 906 so as to determine the number of thermally distinguishable objects in the living body as further detailed hereinabove.

The following description is of techniques for obtaining the thermospatial images, according to various exemplary embodiments of the present invention. The techniques described below can be employed by any of the method and apparatus described above.

A thermospatial image can be generated obtained by acquiring one or more thermographic images and mapping the thermographic image(s) on a 3D spatial representation.

Figure 12A:
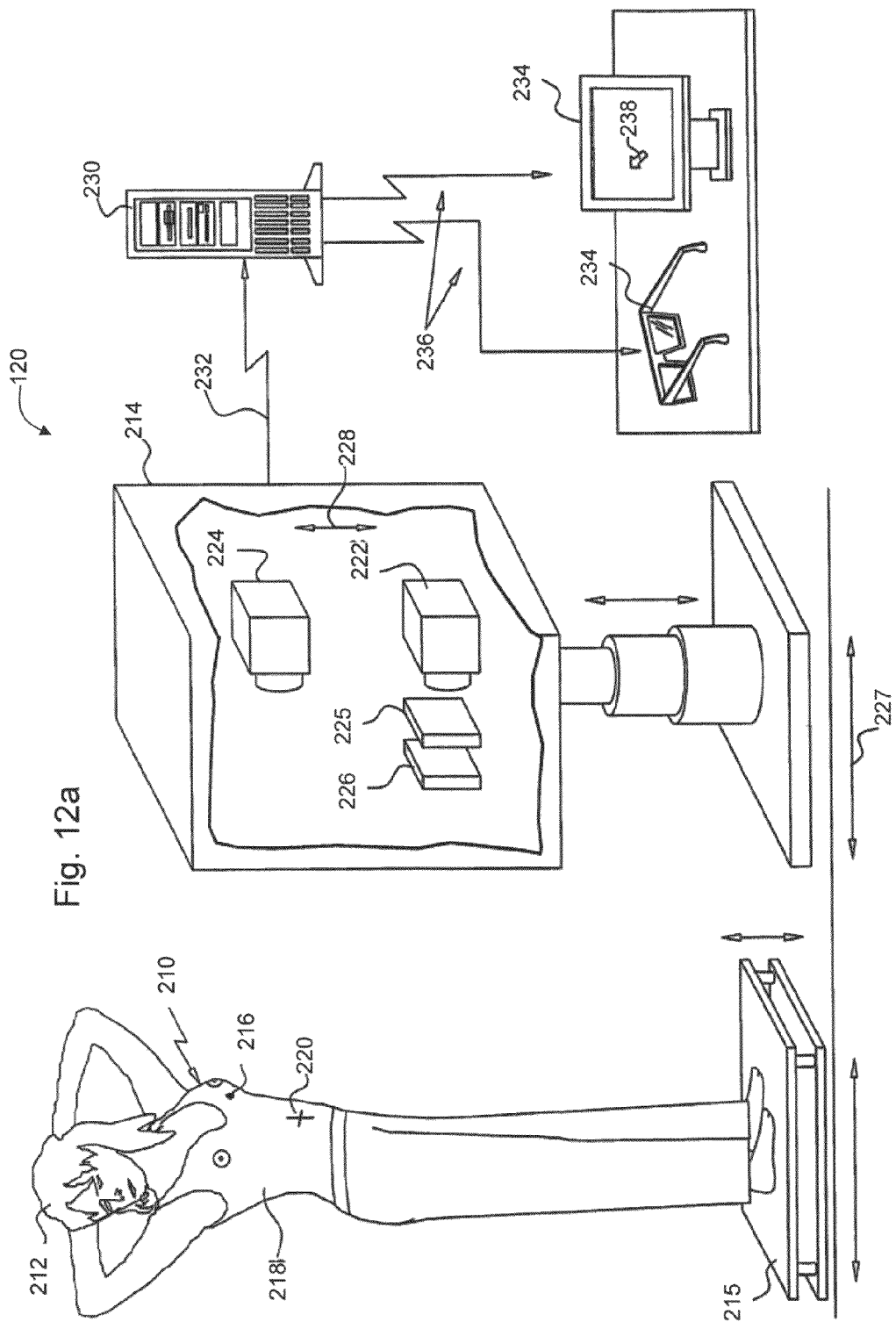

Reference is now made to FIG. 12a which is a schematic illustration of a thermospatial imaging system 120 in accordance with preferred embodiments of the present invention. As shown in FIG. 12a, a living body 210 or a part thereof of a person 212 is located in front of an imaging device 214. The person 212, may be standing, sitting or in any other suitable position relative to imaging device 214. Person 212 may initially be positioned or later be repositioned relative to imaging device 214 by positioning device 215, which typically comprises a platform moving on a rail, by force of an engine, or by any other suitable force. Additionally, a thermally distinguishable object 216, such as a tumor, may exist in body 210 of person 212. For example, when body 210 comprises a breast, object 216 can be a breast tumor such as a cancerous tumor.

In accordance with a preferred embodiment of the present invention, person 212 may be wearing a clothing garment 218, such as a shirt. Preferably, clothing garment 218 may be non-penetrable or partially penetrable to visible wavelengths such as 400-700 nanometers, and may be penetrable to wavelengths that are longer than visible wavelengths, such as infrared wavelengths. Additionally, a reference mark 220 may be located close to person 212, preferably directly on the body of person 212 and in close proximity to body 210. Optionally and preferably, reference mark 220 is directly attached to body 210. Reference mark 220 may typically comprise a piece of material, a mark drawn on person 212 or any other suitable mark, as described herein below.

Imaging device 214 typically comprises at least one visible light imaging device 222 that can sense at least visible wavelengths and at least one thermographic imaging device 224 which is sensitive to infrared wavelengths, typically in the range of as 3-5 micrometer and/or 8-12 micrometer. Typically imaging devices 222 and 224 are capable of sensing reference mark 220 described hereinabove.

Optionally, a polarizer 225 may be placed in front of visible light imaging device 222. As a further alternative, a color filter 226, which may block at least a portion of the visible wavelengths, may be placed in front of visible light imaging device 222.

Typically, at least one visible light imaging device 222 may comprise a black-and-white or color stills imaging device, or a digital imaging device such as CCD or CMOS. Additionally, at least one visible light imaging device 222 may comprise a plurality of imaging elements, each of which may be a three-dimensional imaging element.

Optionally and preferably, imaging device 214 may be repositioned relative to person 212 by positioning device 227. As a further alternative, each of imaging devices 222 and 224 may also be repositioned relative to person 212 by at least one positioning device 228. Positioning device 227 may comprise an engine, a lever or any other suitable force, and may also comprise a rail for moving imaging device 214 thereon. Preferably, repositioning device 228 may be similarly structured.

Data acquired by visible light imaging device 222 and thermographic imaging device 224 is output to a data processor 230 via a communications network 232, and is typically analyzed and processed by an algorithm running on the data processor. The resulting data may be displayed on at least one display device 234, which is preferably connected to data processor 230 via a communications network 236. Data processor 230 typically comprises a PC, a PDA or any other suitable data processor. Communications networks 232 and 236 typically comprise a physical communications network such as an internet or intranet, or may alternatively comprise a wireless network such as a cellular network, infrared communication network, a radio frequency (RF) communications network, a blue-tooth (BT) communications network or any other suitable communications network.

In accordance with a preferred embodiment of the present invention display 234 typically comprises a screen, such as an LCD screen, a CRT screen or a plasma screen. As a further alternative display 234 may comprise at least one visualizing device comprising two LCDs or two CRTs, located in front of a user's eyes and packaged in a structure similar to that of eye-glasses. Preferably, display 234 also displays a pointer 238, which is typically movable along the X, Y and Z axes of the displayed model and may be used to point to different locations or elements in the displayed data.

Reference is now made to FIGS. 12b-f and 13a-e which illustrate the various operation principles of thermospatial imaging system 120, in accordance with various exemplary embodiments of the invention.

The visible light imaging is described first, with reference to FIGS. 12b-f, and the thermographic imaging is described hereinafter, with reference to FIGS. 13a-e. It will be appreciated that the visible light image data acquisition described in FIGS. 12b-f may be performed before, after or concurrently with the thermographic image data acquisition described in FIGS. 13a-e.

Referring to FIGS. 12b-f, person 212 comprising body 210 is located on positioning device 215 in front of imaging device 214, in a first position 240 relative to the imaging device. First image data of body 210 is acquired by visible light imaging device 222, optionally through polarizer 225 or as an alternative option through color filter 226. The advantage of using a color filter is that it can improve the signal-to-noise ratio, for example, when the person is illuminated with a pattern or mark of specific color, the color filter can be used to transmit only the specific color thereby reducing background readings. Additionally, at least second image data of body 210 is acquired by visible light imaging device 222, such that body 210 is positioned in at least a second position 242 relative to imaging device 214. Thus, the first, second and optionally more image data are acquired from at least two different viewpoint of the imaging device relative to body 210.

Figure 12B:
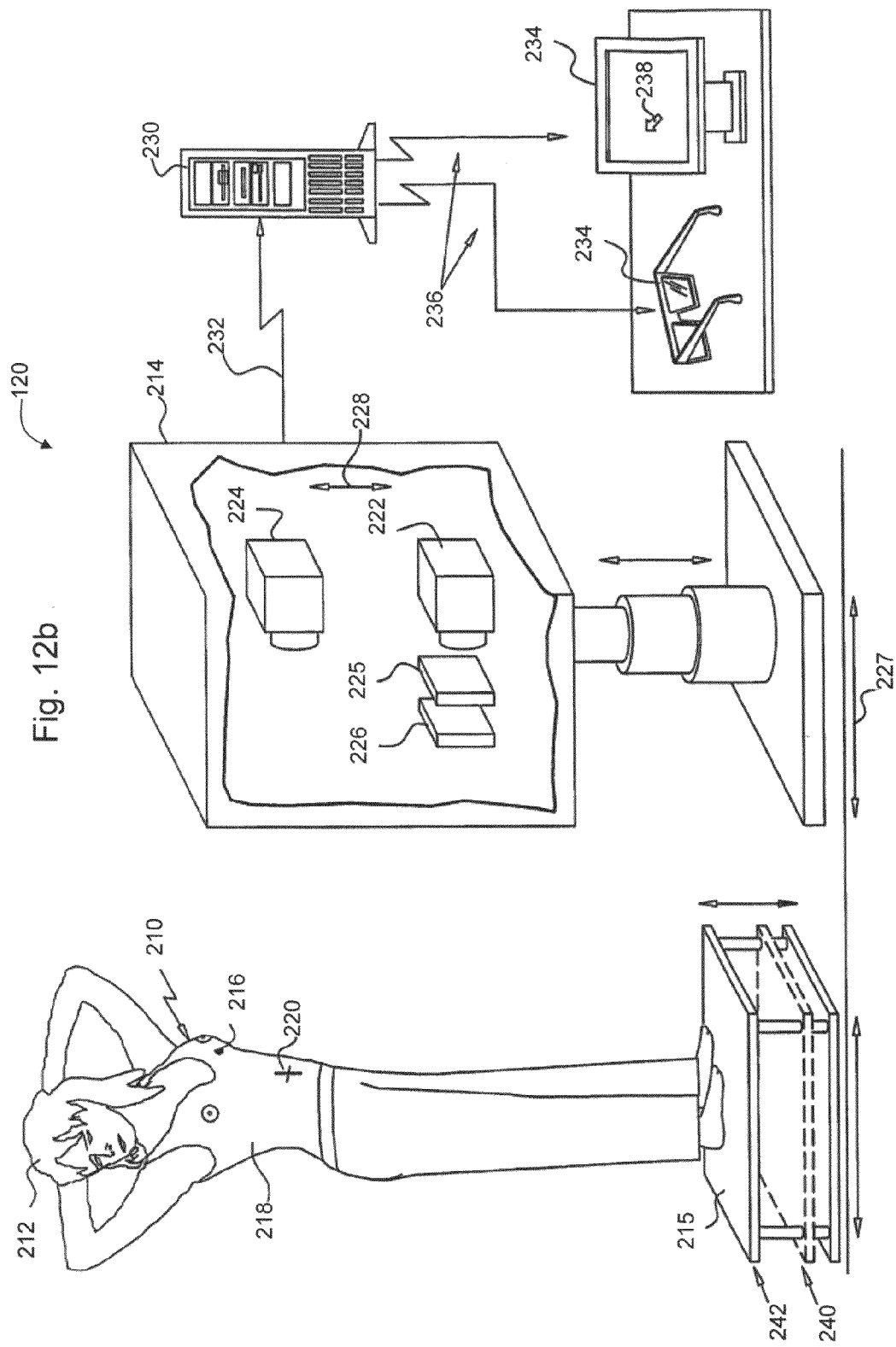
Figure 12D:
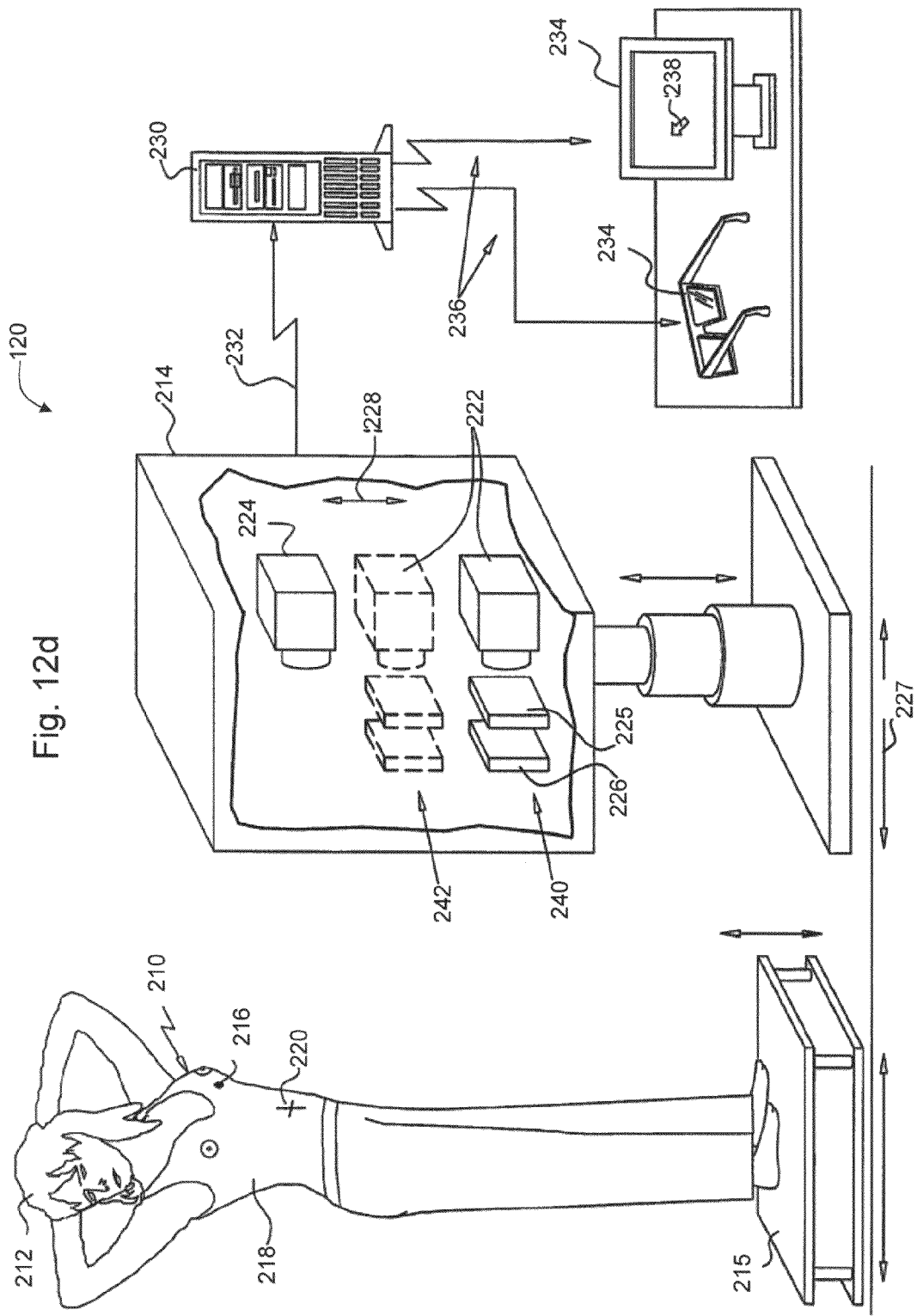
Figure 12F:
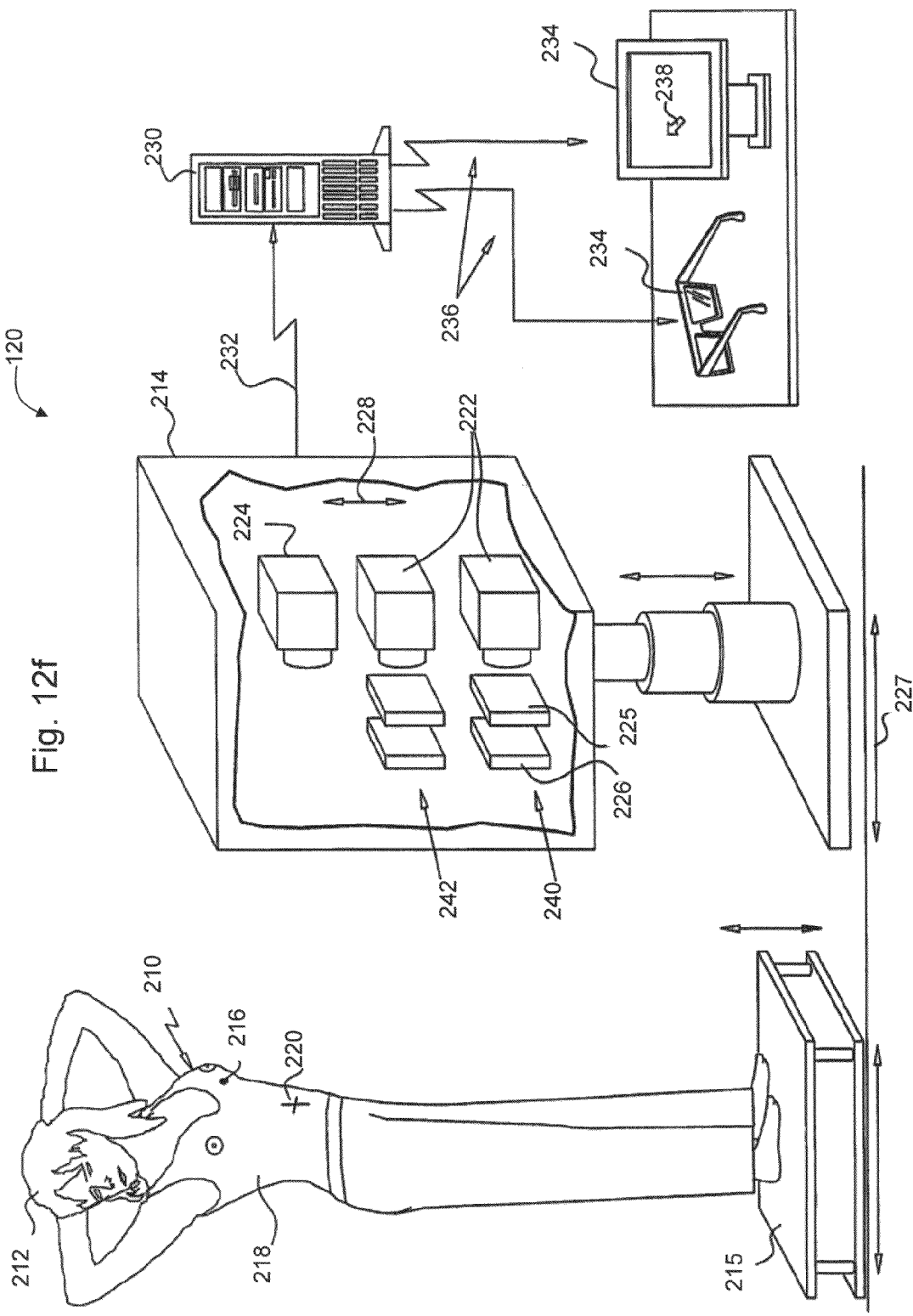

The second relative position 242 may be configured by repositioning person 212 using positioning device 215 as seen in FIG. 12b, by repositioning imaging device 214 using positioning device 227 as seen in FIG. 12c or by repositioning imaging device 222 using positioning device 228 as seen in FIG. 12*d*. As a further alternative, second relative position 242 may be configured by using two separate imaging devices 214 as seen in FIG. 12*e* or two separate visible light imaging device 222 as seen in FIG. 12*f*.

Referring to FIGS. 13*a-e*, person 212 comprising body 210 is located on positioning device 215 in front of imaging device 214, in a first position 244 relative to the imaging device. First thermographic image data of body 210 is acquired by thermographic imaging device 224. Optionally and preferably at least second thermographic image data of body 210 is acquired by thermographic imaging device 224, such that body 210 is positioned in at least a second position 242 relative to imaging device 214. Thus, the first, second and optionally more thermographic image data are acquired from at least two different viewpoints of the thermographic imaging device relative to body 210.

Figure 13A:
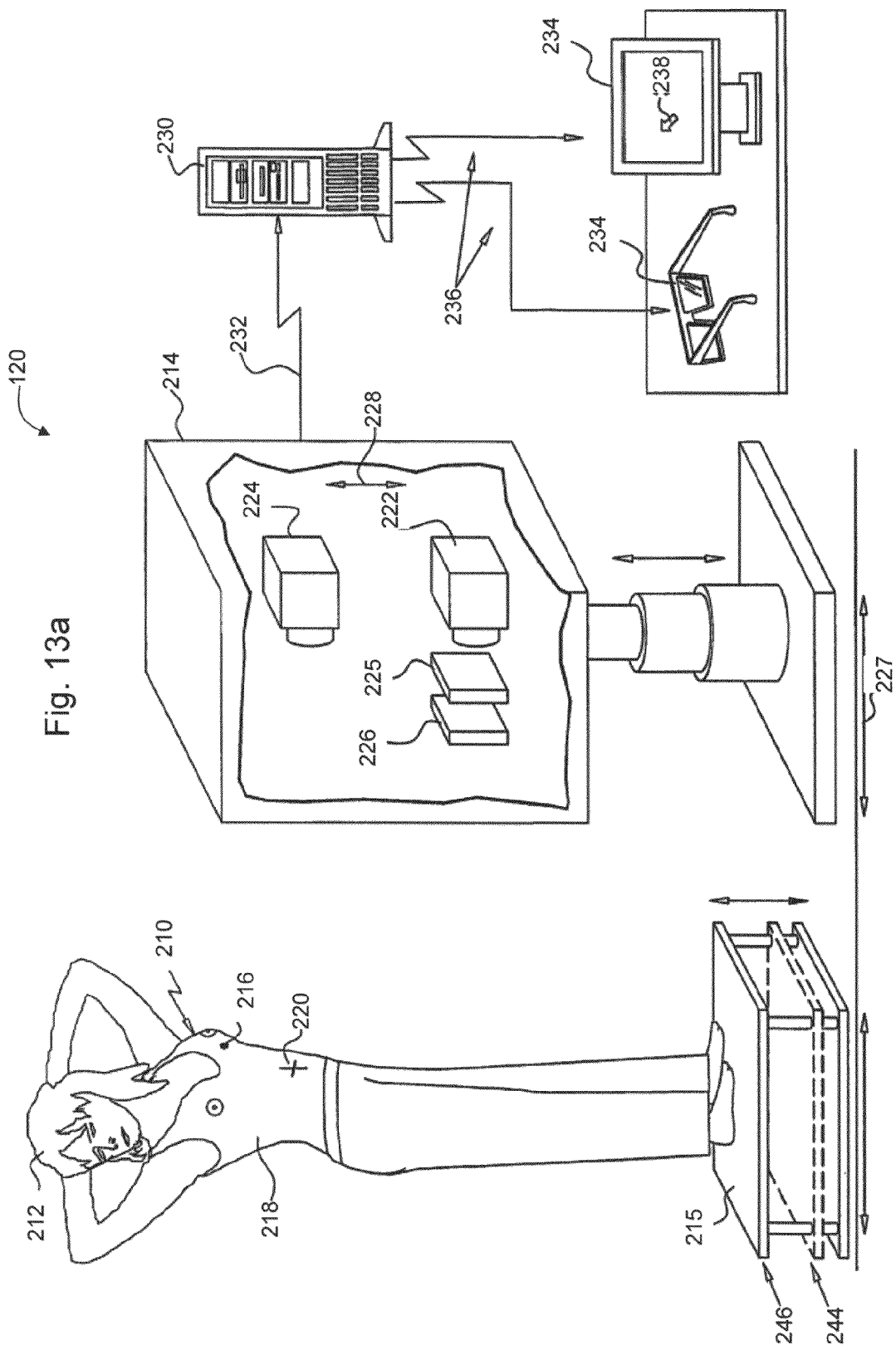
Figure 13B:
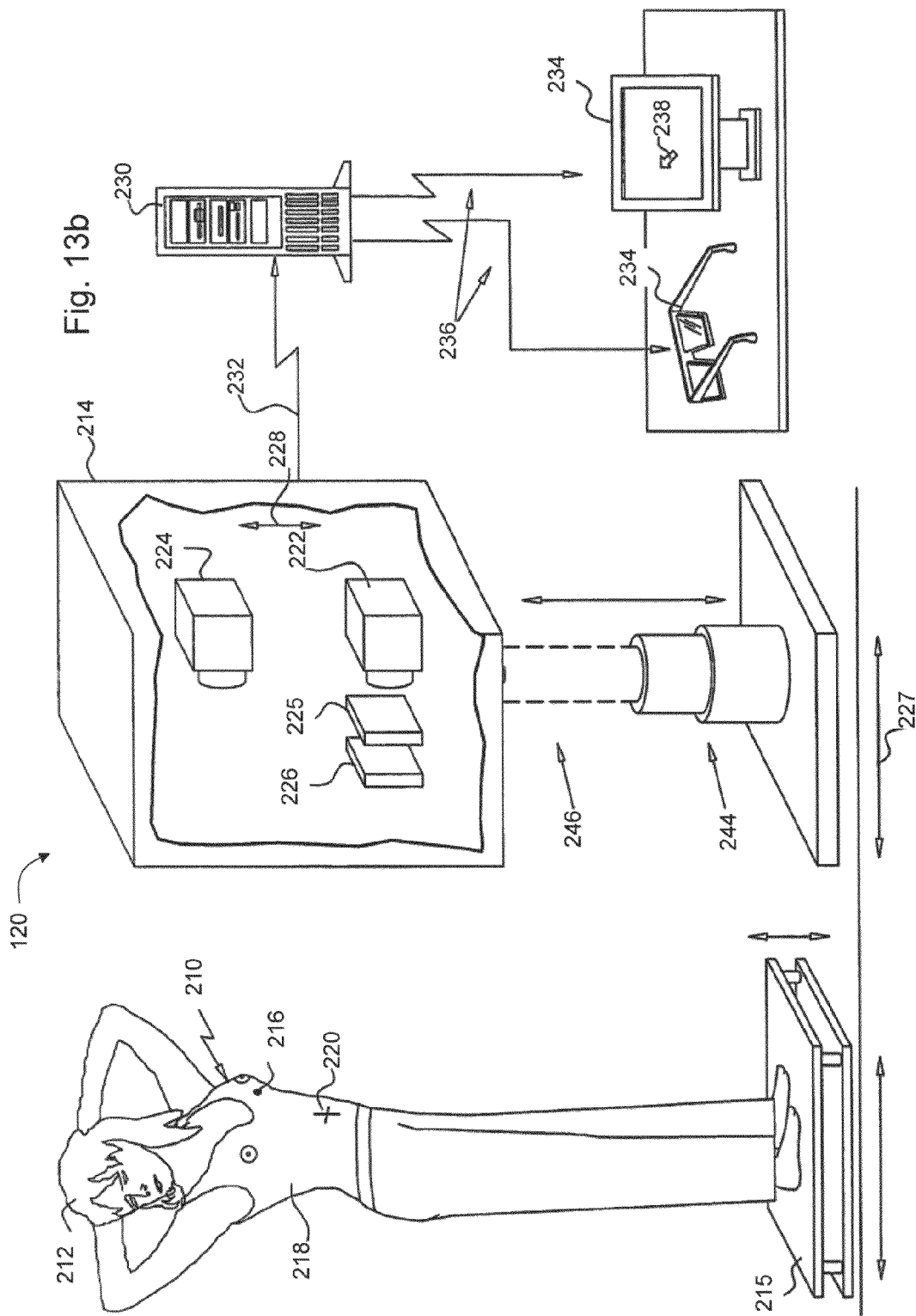
Figure 13C:
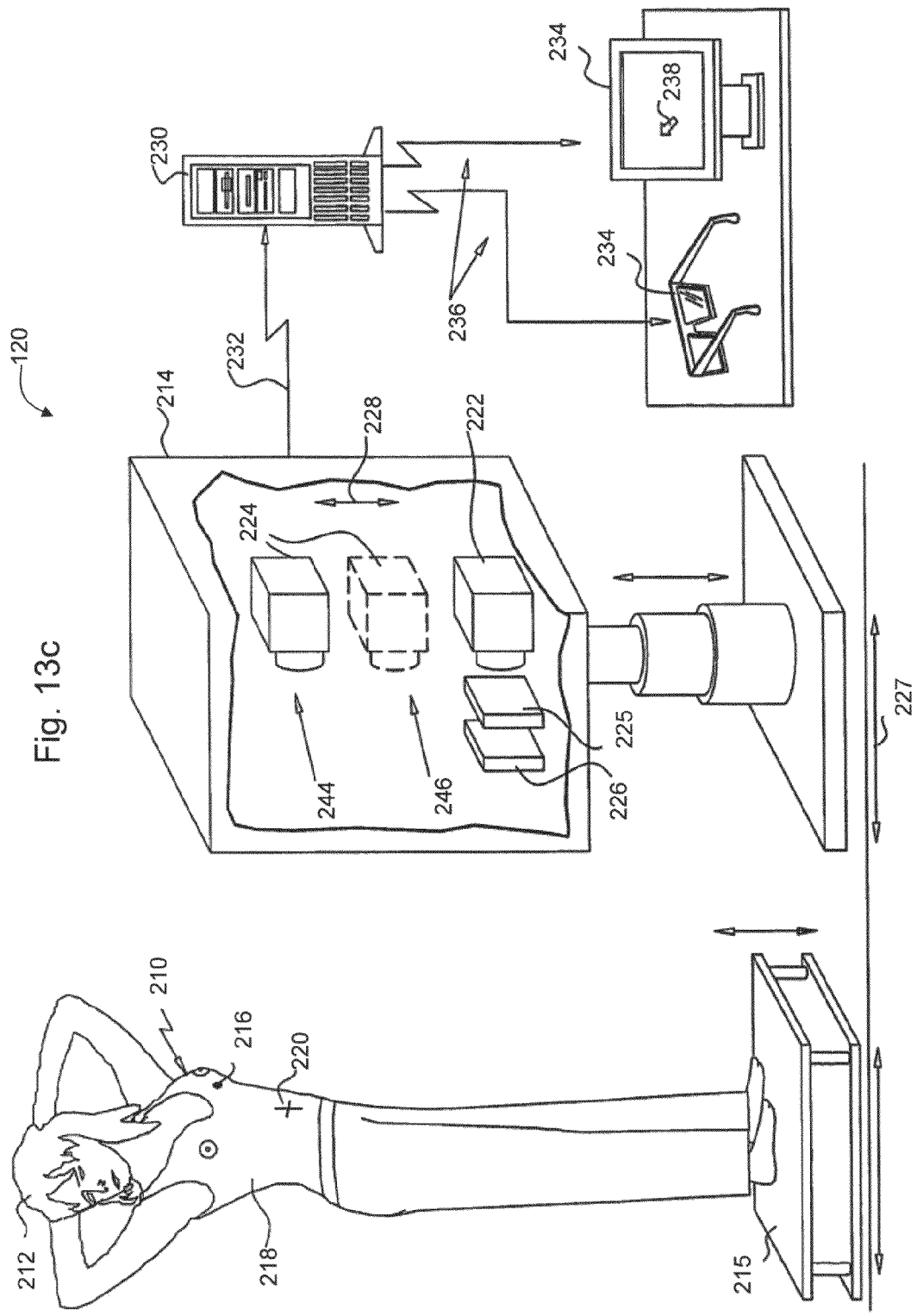
Figure 13E:
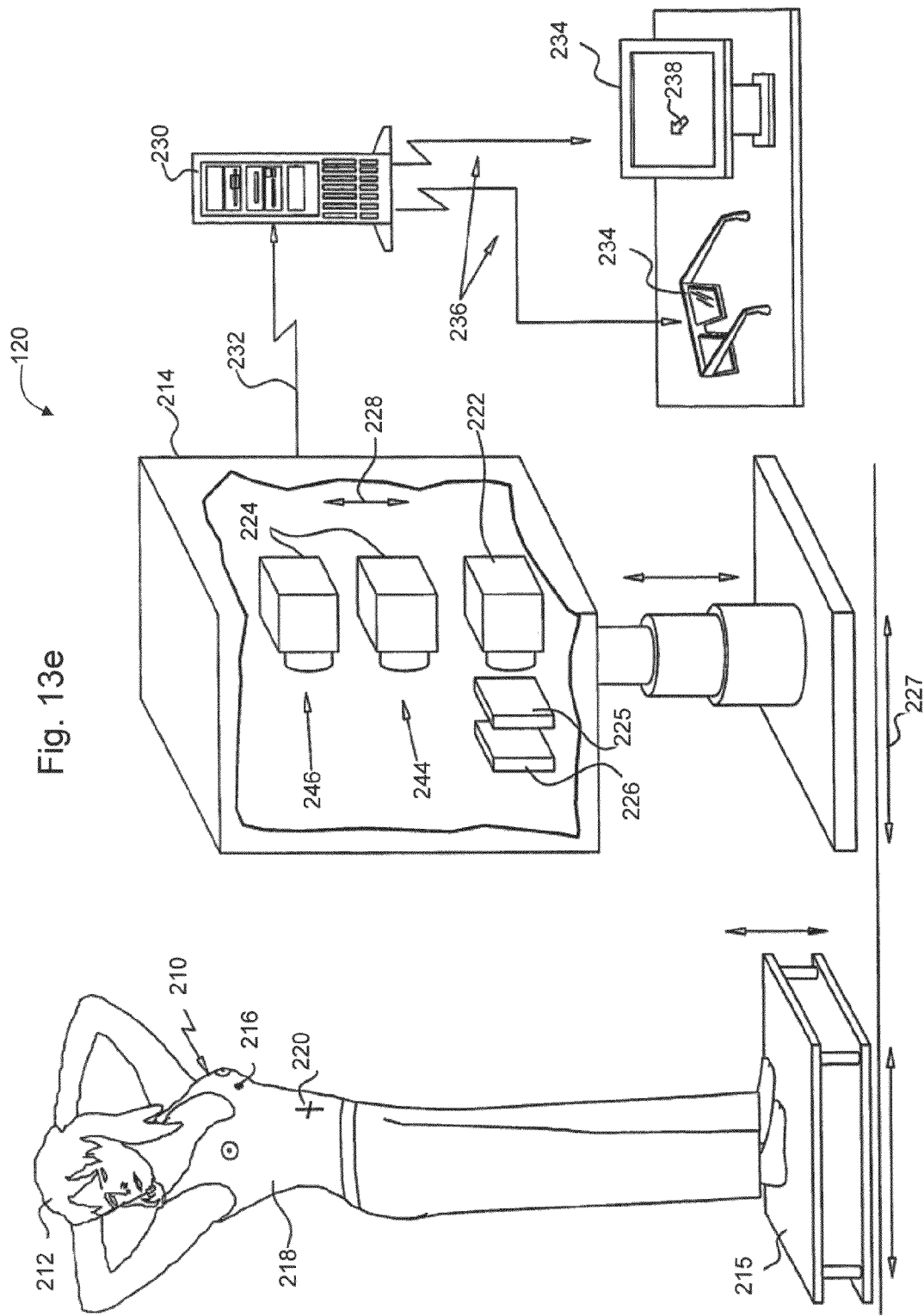

The second relative position 246 may be configured by repositioning person 212 using positioning device 215 as seen in FIG. 13*a*, by repositioning imaging device 214 using positioning device 227 as seen in FIG. 13*b*, or by repositioning thermographic imaging device 224 using positioning device 228 as seen in FIG. 13*c*. As a further alternative, the second relative position 246 may be configured by using two separate imaging devices 214 as seen in FIG. 13*d* or two separate thermographic imaging devices 224 as seen in FIG. 13*e*.

Image data of body 210 may be acquired by thermographic imaging device 224, by separately imaging a plurality of narrow strips of the complete image of body 210. Alternatively, the complete image of body 210 is acquired by the thermographic imaging device, and the image is sampled in a plurality of narrow strips or otherwise shaped portions for processing. As a further alternative, the imaging of body 210 may be performed using different exposure times.

The thermographic and visible light image data obtained from imaging device 214 is preferably analyzed and processed by data processor 230 as follows. Image data acquired from imaging device 222 is processed by data processor 230 to build a three-dimensional spatial representation of body 210, using algorithms and methods that are well known in the art, such as the method described in U.S. Pat. No. 6,442,419 which is hereby incorporated by reference as if fully set forth herein. The 3D spatial representation preferably comprises the location of reference marker 220 (cf. FIG. 1*a*). Optionally and preferably, the 3D spatial representation comprises information relating to the color, hue and tissue texture of body 210. Thermographic image data acquired from imaging device 224 is processed by data processor 230 to build a thermographic three-dimensional model of body 210, using algorithms and methods that are well known in the art, such as the method described in U.S. Pat. No. 6,442,419. The thermographic 3D model preferably comprises reference marker 220 (cf. FIG. 1*b*). The thermographic 3D model is then mapped by processor 230 onto the 3D spatial representation, e.g., by aligning reference marker 220, to form the thermo-spatial image.

The combination of two or more visible light images to construct the 3D spatial representation of body 210, and the combination of two or more thermographic images to construct the thermographic 3D model, may require regionwise comparison between image data (either in visible light or thermographic) acquired from different viewpoints. Such comparison is typically a twofold process: firstly, selected groups of picture-elements are identified in each individual image, and secondly the identified groups of picture-elements of one image are matched among the various images. The present embodiments successfully provide a method suitable for improving the identification and matching processes.

According to a preferred embodiment of the present invention the body is illuminated with a series of spots, where at least one spot of the series is distinguishable from all other spots. A representative example of such series is illustrated in FIG. 14 showing a series 142 of spots, in which one spot 144 (the third from left, in the present example) is distinguished from all other spots. In the representative example of FIG. 14, series 142 is a row of spots, but it is to be understood that the series can have any geometrical property, either one-dimensional (e.g., a row, a column, an arc, a curvilinear line, etc.), or two-dimensional (e.g., a matrix). Spot 144 can be distinguished by any distinguishing feature, include, without limitation, shape, size, wavelength, intensity and orientation.

Once the body is illuminated with the series, one or more imaging devices are preferably used for acquiring two or more images of the body and the series from at least two different viewpoints. The images can be visible light images acquired using one or more visible light imaging devices, or thermographic images acquired using one or more thermographic imaging devices. The wavelength or range of wavelengths of series 142 is compatible with the range of wavelengths to which the imaging device is sensitive. Thus, for visible light image, series 142 is generally illuminated at the visible range of wavelengths, and for thermographic image, series 142 is generally illuminated at the infrared range of wavelengths.

Once the images are acquired, the distinguishable spot 144 is preferably identified and used for identifying all other spots in series. With reference to the exemplified series of FIG. 14, knowing the number of spots in the series and the relative position of spot 144 in the series (third from the left in the present example) all other spots can be identified by their relative position with respect to spot 144. Thus, the method can scan across all picture-elements along a line of the image and counts the spots beginning with the already identified spot.

Thus, the present embodiments use spot 144 as a pointer for indexing all the spots in series 142. Such indexing greatly enhances the efficiency of the matching step, because it allows the matching at series level as opposed to spotwise matching. Since the series can in principle be of any length, a single series matching can encompass large portion of the images.

The matching enables the calculations of range data for at least some spots, more preferably for each spot in the series, typically by triangulation. The 3D spatial representation or the 3D thermographic model can then be built using the range data.

According to another embodiment of the present invention, the identification and matching of points is performed for a small number of illuminated spots, e.g., 5 spots, more preferably 4 spots, more preferably 3 spots, more preferably 2 spots, more preferably a single spot. In this embodiment, a plurality of images is acquired from each view point, where each such acquisition is preceded with an illumination of a different region or location on the body's surface with spots. The identification and matching of the spots is performed separately for each such region or location.

In any of the above embodiments, identification of the spots can be realized by subtraction. More specifically, each image is acquired twice: one time without illuminating the body with spots and another time with the spots. The image acquired without spots is then subtracted from the image acquired with the spots, and the remaining data include mostly information regarding the spots with minimal or no background noise.

It is appreciated that range imaging systems and thermospatial imaging systems, such as system 120 above or other systems as further described below, may require a calibration step before the acquisition.

The present embodiments successfully provide a calibration procedure which employs a database of figures having a plurality of entries, each having a figure entry and an angle entry corresponding to a viewpoint of the figure entry. The database is typically prepared in advance by projecting figures, which can be, e.g., geometrical figures, on a surface from a plurality of different view points and determining the distortion caused to each figure for each viewpoint. Each distorted figure is recorded as a figure-entry and each viewpoint is recorded as an angle entry of the database. The calibration is preferably performed as follows. The body is illuminated with a figure and at least two images of the body and the figure are acquired from at least two different viewpoints. For each image, the acquired figure is identified. The database is accessed and searching over database for a figure entry which is generally similar to the identified figure of the respective image. Once the figure entries are found for all images, the respective angle entries are used for calculating range data by triangulation. The advantage of the calibration procedure of the present embodiments is that the search over the database can, in principle, be faster than a complete calculation of the angles.

Calibration of a thermospatial imaging system according to various exemplary embodiments of the present invention can also be done by illuminating the body with a pattern in a plurality of wavelengths, where at least one wavelength is detectable by the thermographic imaging device of the system and at least one wavelength is detectable by the visible light imaging device of the system. Illuminating devices capable of providing such illumination are known in the art. For example, an infrared lamp such as one of the IR-50 series, which is commercially available from Scitec Instruments Ltd, UK, can be employed. Using the thermographic and visible light imaging devices a thermographic image and a visible light image of the body are acquired. The calibration is performed by aligning the pattern as acquired by the visible light imaging device with the pattern as acquired by the thermographic imaging device. According to a preferred embodiment of the present invention the thermographic and visible light images are acquired substantially simultaneously, such that the body is essentially static during the calibration.

The identification of the pattern can optionally and preferably by employing the indexing technique as further detailed hereinabove with reference to FIG. 14.

Reference is now made to FIG. 15 which is a flowchart diagram of a method 150 suitable for constructing a 3D spatial representation of a body, according to various exemplary embodiments of the present invention. In various exemplary embodiments of the invention method 150 constructs the 3D spatial representation based on thermographic images and preferably without using visible light images.

Method 150 begins at step 152 and continues to step 154 in which the body is illuminated with a pattern, e.g., a coded pattern in the infrared range. The pattern can be in any shape which allows the identification thereof. For example, in one embodiment the pattern comprises one or more bar codes, in another embodiment, the pattern comprises a series of spots such as series 144 described above, in a further embodiment, the pattern comprises a combination of bar cods and a series of spots.

Typically the pattern is illuminated using a laser light with wavelength of 3-14 micrometer. According to a preferred embodiment of the present invention a $CO_2$ laser with wavelength of 10.6 micrometer is employed. Alternatively, an infrared lamp such as one of the IR-50 series, which is commercially available from Scitec Instruments Ltd, UK, can be employed. The pattern is selected in accordance with the desired technique which is used to construct the three-dimensional spatial representation. Thus, the pattern can be selected to allow temporal coding and/or spatial coding.

Preferably, the pattern projected on the body varies with time. For example, a series of patterns can be projected, one pattern at a time, in a rapid and periodic manner. This can be done in any of a number of ways. For example, a plate having a periodically varying transmission coefficient can be moved in front of an illuminating device. Alternatively, a disk having a circumferentially varying transmission coefficient can be rotated in front of the illuminating device. Still alternatively, strobing technique can be employed to rapidly project a series of stationary patterns, phase shifted with respect to each other. Also contemplated is the use of optical diffractive elements for forming the pattern. The pattern can also be in the form of a series of spots, as further detailed hereinabove (cf. FIG. 14 and the accompanying description). A preferred illuminating device for providing a pattern is described hereinunder.

In various exemplary embodiments of the invention the illumination is characterized by sufficiently short pulse length. Preferably pulses shorter than 20 milliseconds, e.g., 15 milliseconds or less, more preferably 10 milliseconds or less, are employed.

Method 150 continues to step 156 in which one or more thermographic imaging device is used for acquiring one or more thermographic images of the body and the pattern. The thermographic imaging device is preferably equipped with a suitable optics for acquiring data in the infrared range from the body and the pattern. Such optics is commercially available from, e.g., Holo-Or Ltd, Israel. In various exemplary embodiments of the invention the method acquires two or more thermographic images of the body and the pattern from two or more different viewpoints. The thermographic imaging is performed in accordance with the type of pattern which is selected. For example, when temporal coding is employed, the thermographic imaging device is synchronized with the pulses of the illumination.

According to a preferred embodiment of the present invention the exposure times of the thermographic imaging device are of less than 20 milliseconds. Preferably, the exposure time and the readout time of the thermographic imaging device complement to 20 milliseconds for each cycle. For example, in one embodiment the exposure time is 19 milliseconds and the readout is during 1 millisecond. This embodiment is illustrated in FIG. 16a.

In an alternative embodiment, several readouts are executed simultaneously with one exposure. In this embodiment, the exposure time can be of 20 milliseconds or less. This embodiment is illustrated in FIG. 16b. According to a preferred embodiment of to the present invention the readouts are executed accumulatively. This can be done, for example, by accumulating the acquired signal to previously stored signal in the imaging device's pixel without erasing or overwritten the previous signal. After several readouts, say every 20 milliseconds, the data stored in the imaging device's pixel can be erased. Alternatively, the accumulation can be performed digitally.

In an alternative embodiment, both the exposure time and readout time are shorter than 20 milliseconds. This embodiment is illustrated in FIG. 16c.

According to a preferred embodiment of the present invention the method proceeds to step 158 in which image data originating from heat generated by the body is filtered out from the acquired thermographic image. This can be done by processing the thermographic image(s), e.g., using digital intensity filters. Alternatively, one or more thermographic images of the body are acquired without the pattern, and the filtration is achieved by subtracting the thermographic images acquired without the pattern from thermographic images acquired with the pattern.

The method continues to step 160 in which range data corresponding to pattern are calculated. The range data can be calculated by time-of-flight technique, triangulation or any technique known in the art, to this end see, e.g., S. Inokuchi, K. Sato, and F. Matsuda, "Range imaging system for 3D object recognition", in Proceedings of the International Conference on Pattern Recognition, pages 806-808, 1984; and U.S. Pat. Nos. 4,488,172, 4,979,815, 5,110,203, 5,703,677, 5,838,428, 6,349,174, 6,421,132, 6,456,793, 6,507,706, 6,584,283, 6,823,076, 6,856,382, 6,925,195 and 7,194,112.

The method continues to step 162 in which the thermographic image and the range data are used for constructing the 3D spatial representation of the body.

Once constructed, the 3D spatial representation can be displayed in a visible form, e.g., using a display device or a printer, or it can be digitally recorded on a computer readable medium. The 3D spatial representation can also be outputted, e.g., digitally, to another system or apparatus which is configured to receive the 3D spatial representation and analyze and/or process it. For example, the 3D spatial representation can be outputted to a system or apparatus which generates a thermospatial image. The method ends at step 164.

FIG. 17 is a schematic illustration of a system 170 for constructing a three-dimensional spatial representation of a body. System 170 can be used for executing method 150 or selected steps thereof. System 170 comprises an illuminating device 172, which is designed and constructed to illuminate the body 210 with a pattern 174 in the infrared range. Pattern 174 is illustrated as a bar code, this need not necessarily be the case, since, for some applications, it may not be necessary for the pattern to be in the form of a bar code. Thus, pattern 174 can be of any shape and texture. Further, although the a single pattern is shown in FIG. 17, this need not necessarily be the case since device 172 can be configured to illuminate body 210 by more than one pattern. Thus, the present embodiments also contemplate a series of patterns. In preferred embodiment of the invention pattern 174 comprises at least in part series 142 so as to allow indexing as further detailed hereinabove.

Device 172 can comprise a laser device, an infrared lamp, or any other illuminating device capable of providing light in the infrared range and optionally also in the visible range as described above. System 170 further comprises one or more thermographic imaging devices 224 which acquire one or more thermographic images of body 210 and pattern 174. Preferably, thermographic imaging devices 224 acquire at least two images from at least two different viewpoints. System 170 further comprises a data processor 230 which calculates range data corresponding to pattern, and constructs the 3D spatial representation of body 210 as further detailed hereinabove. In various exemplary embodiments of the invention processor 230 filters out image data originating from heat generated by the body, e.g., by subtracting thermographic images acquired without pattern 174 from thermographic images acquired with pattern 174 as further detailed hereinabove.

The techniques of the present embodiments can be utilized for obtaining and/or analyzing thermospatial images of portions of external as well as internal organs of the body. The techniques of the present embodiments can also be employed during open surgery in which case the organ to be thermospatially imaged can be accessed using the thermospatial system. Thermospatial systems most suitable for open surgery applications according to preferred embodiments of the present invention are similar to the system described above, but preferably with miniaturized imaging devices to allow easy access to the internal organs. This embodiment is particularly useful for imaging internal organs which are both accessible and movable by the surgeon during open surgery.

In cases of tumors in the liver (adenomas, hepatoma, etc.), for example, during open surgery, the surgeon positions the imaging devices near the liver and acquires the thermospatial image of the liver to determine locations of pathologies such as tumors therein. Once the location(s) are determined, the surgeon can destroy the tumor, e.g., by ablation or cavitation. It is recognized that as the liver is an extremely bloody organ, the ability of destroying tumors in the liver without invading the liver's tissue is of utmost importance. Furthermore, in extreme cases, a portion of the liver containing an untreatable amount of tumors can be removed, while the remaining portion which contains fewer tumors (e.g., metastases) can be thermospatially imaged and the tumors therein can be destroyed by ablation or cavitation. The above procedure can be performed also for other organs such as a kidney, colon, stomach or pancreas.

Another organ which can be imaged in various exemplary embodiments of the invention is the brain. The brain can contain many types of tumors which can be located and optionally diagnosed, according to the teaching of the present embodiments. Representative examples of such tumors include, without limitation, primary benign tumors such as meningioma, primary malignant tumors such as glyoblastoma or astrocytoma, and any malignant metastasis to the brain from any organ such as colon, breast, testis and the like.

This can be achieved, for example, during open brain surgery. In this embodiment, a portion of the cranium is removed and the imaging devices of the thermospatial are inserted in a predetermined arrangement, between the brain and the remaining portion of the cranium. A thermospatial image of the brain can then be generated as further detailed hereinabove. If the brain contains pathologies such as tumors, the pathologies can be destroyed or at least partially damaged, for example, by ablation or cavitation.

The technique of the present embodiments can also be employed in minimally invasive procedures. To this end the present Inventor contemplates a thermospatial imaging system generally referred to herein as system 180 and schematically illustrated in FIGS. 18a-c.

Referring to FIGS. 18a-c, system 180 comprises, in its simplest configuration, an intracorporeal probe system 182 having therein one or more thermographic imaging devices 184 for acquiring at least one thermographic image of the anterior of the living body.

Intracorporeal probe system 182 is preferably inserted endoscopically by mounting the device on a suitable transport mechanism, such as, but not limited to, an endoscopic probe or a catheter. Intracorporeal probe system 182 is preferably flexible so as to facilitate its endoscopic insertion. Additionally and preferably intracorporeal probe system 182 is sizewise and geometrically compatible with the internal cavities of the subject so as to minimize discomfort of the subject during the non-invasive in vivo examination. Thus, intracorporeal probe system 182 is preferably adapted for transrectal, transurethral, transvaginal or transesophageal examination Imaging device 184 is preferably a miniature imaging device to allow mounting it on probe system 182. System 180 further comprises data processor 230 which communicates with probe system 182, for example, via wireless communication system having a first transmitter/receiver 186 on probe system 182 and a second transmitter/receiver 188 on processor 230. Alternatively, communication can be established via a communication line 190. Image data acquired by imaging device 184 is transmitted via probe system 182 to processor 230 which receives the image data and analyzes it to provide and display a synthesized thermospatial image of the anterior of the living body. The generation of thermospatial image is, as stated by mapping one or more thermographic images onto surface 205 of 3D spatial representation 206.

In various exemplary embodiments of the invention probe system 182 further comprises one or more visible light imaging devices 192 which acquire at least one visible light image of the anterior of the living body and transmits image data pertaining to the visible light image via probe system 182 to processor 230. In this embodiment, processor 230 uses the visible light image data for constructing the 3D spatial representation.

Alternatively, as illustrated in FIG. 18b, system 180 comprises two intracorporeal probe systems, designated 182 and 182', where thermographic imaging device(s) 184 is mounted on probe system 182 and visible light imaging device(s) 192 is mounted on probe system 182'. In this embodiment, probe systems 182 and 182' preferably communicate thereamongst, via transmitter/receiver 186 or communication line 190, for example, to allow synchronization.

In yet another alternative, as illustrated in FIG. 18c, system 180 comprises two intracorporeal probe systems, 182 and 182' each having both thermographic 184 and visible light 192 imaging device(s). Similarly to the embodiment in FIG. 18b, probe systems 182 and 182' preferably communicate thereamongst.

In various exemplary embodiments of the invention system 180 further comprises an, illuminating device 194 for illuminating the anterior of the body with a pattern. The pattern serves for the calculation of range data as further detailed herein above. Illuminating device 194 is preferably mounted on probe system 182

Generally, system 180 can be employed in many minimally invasive procedures, including, without limitation, Arthroscopy, Bronchoscopy, Colonoscopy, Colposcopy, Cystoscopy, Endoscopic Biopsy, Gastroscopy, Laparscopy, Laryngoscopy, Proctoscopy, Thoracocopy, Esophogeal-gastroduodensoscopy, and endoscopic retrograde cholangio-pancreatography.

Reference is now made to FIG. 19a, which is a schematic illustration of an embodiment in which the intracorporeal probe system is used for thermospatially imaging the stomach. Shown in FIG. 19a is the esophagus 360 and the stomach 361 (image source: National Library of Medicine (NLM) web site). Also shown is the intracorporeal probe system 182, inserted through esophagus 360 by a catheter 363 and positioned in stomach 361. This embodiment can be used for imaging benign tumors such as Leomyoma, or malignant tumors such as carcinoma or lymphoma.

The ability to insert the intracorporeal probe system 182 through the esophagus allows the operator to obtain thermospatial images of the esophagus itself, thereby to locate pathologies, such as the carcinoma of the esophagus, thereon.

Reference is now made to FIG. 19b, which is a schematic illustration of an embodiment in which intracorporeal probe system 182 is used for thermospatially imaging the prostate or bladder. Shown in FIG. 19b are the rectum 367, the bladder 366, the prostate 370 and the urethra 369. In the present embodiments, intracorporeal probe system 182 can be inserted into through the anus 368 into the rectum 367, or through the urethra 369. When device probe system 182 is inserted through the urethra it can be used for imaging the prostate, in which case probe system 182 is positioned near the prostate, or the bladder, in which case probe system 182 is inserted into the bladder as shown in FIG. 19b.

Reference is now made to FIG. 19c, which is a schematic illustration of an embodiment in which probe system 182 is used for thermospatially imaging the uterus, bladder or ovary. Shown in FIG. 19c are the rectum 367, the bladder 366, the uterus 372 and the ovary 373. In the present embodiments, probe system 182 can be inserted through the vagina 374. Probe system 182 can alternatively be mounted on a catheter and inserted into the uterus. The thermospatial imaging of this embodiment can be used for locating or diagnosing polyps in the uterus or bladder. Additionally this embodiment can be used for locating and optionally diagnosing benign tumors in the uterus (e.g., myomas) or any malignant tumors therein. For the ovary, this embodiment can be used for thermospatially imaging any primary or secondary malignant tumors therein.

In various exemplary embodiments of the invention two or more 3D spatial representations are constructed, such that different spatial representations correspond to different postures of the subject. These embodiments are applicable for any type of thermospatial imaging described above.

At least a few of these 3D spatial representations are optionally and preferably may accompanied by the acquisition of one or more thermographic image for the respective posture, and the mapping of the respective thermographic image on the respective 3D spatial representations, such as to provide a plurality of thermospatial images.

One advantageous of several 3D spatial representations is that it can be used by the method of the present embodiments as a consistency test. This is illustrated in FIG. 20 which is a flowchart diagram of a method 400 suitable for assessing the accuracy of the determination of the internal thermally distinguished regions in the body.

Method 400 begins at step 402 and continues to step 404 in which a synthesized thermospatial image is obtained. The thermospatial image can be generated by method 400 or it can be generated by another method or system from which the image can be read by method 400. The method continues to step 406 in which the position and optionally the size of one or more internal three-dimensional thermally distinguishable regions in the living body are determined. This can be done using method 10, method 50 or any other method, including combination between different methods (e.g., methods 10 and 50). Optionally and preferably, the method also determines one or more source regions as described hereinabove.

Method 400 continues to step 408 in which one or more additional 3D spatial representations of the living body are obtained, where each 3D spatial representation corresponds to a different viewpoint with respect to the living body and/or a different posture of the living body. Method 400 can construct the additional 3D spatial representations or they can be constructed by another method or system from which they can be read by method 400.

Method 400 continues to step 410 in which, based on the internal three-dimensional thermally distinguishable region, the expected topology of isothermal contours on the surface the additional 3D spatial representation is constructed for at least a few of the 3D spatial representations. The expected topology preferably includes information regarding the general shape of the contours (closed, open), but it can also include more information, e.g., temperature data on the surface, and the like. The expected topology can be calculated numerically using the position of the internal region in the body, the shape of the 3D spatial representation, and by modeling the thermal conductivity of the body which can be, either isotropic or non-isotropic. For example, the method can construct the expected topology by considering the thermal distance function D as further detailed hereinabove, see FIGS. 10a-e and the accompanying description.

Method 400 continues to step 412 in which one or more additional thermospatial image are obtained, where each thermospatial image corresponds to a different viewpoint with respect to the living body and/or a different posture of the living body. The thermospatial images can be generated by method 400 or they can be generated by another method or system from which the image can be read by method 400. The method continues to step 414 in which the additional thermospatial image(s) are compared to the expected topologies. If the topology of the isothermal contours in an additional thermospatial image is similar to the expected topology, the method can determine that the position and optionally size of the internal region is accurate. Otherwise, the method identifies an error determines that an error has been can Thus, method 400 serves as a consistency check, and determine whether or not there is a consistency with respect to the location of the thermally distinguished object within the body.

Method 400 continues to step 418 in which a report relating to the comparison is issued, and ends at step 419.

An additional advantageous of several 3D spatial representations is that they can serve in preliminary tests to select the proper viewpoint for the imaging and/or the posture of the body. Specifically, for at least a few 3D spatial representations, the expected topology of the isothermal contours on the surface is preferably constructed. Once two or more such expected topologies are known, the operator or physician can select the viewpoint for the imaging and/or the posture of the body which is most suitable for the examination.

For example, suppose that the living body is the breast of a woman, and that a 3D spatial representation is obtained when the woman is standing and a second 3D spatial representation is obtained when the woman bends forwards. Suppose further that for the first 3D spatial representation the expected topology is of open isothermal contours, and that for the second 3D spatial representation the expected topology is of closed isothermal contours. In this case, the operator or physician may decide to select the second posture (bending forward) because the determination of the position of a thermally distinguishable object is more accurate when the thermal data is characterized by closed isothermal contours.

It is preferred that the thermospatial imaging will be performed when there are minimal thermal changes in the body of the subject during the acquisition of thermographic images.

Reference is now made to FIG. 21 which is a flowchart diagram of a method 420 suitable for ensuring that a living body is at a generally stable thermal condition, according to various exemplary embodiments of the present invention. The method begins at step 422 and continues to step 424 in which a series of thermographic images of the living body are acquired from a predetermined viewpoint. Method 420 continues to step 426 in which the thermographic images are compared so as to extract thermal changes in the images. In various exemplary embodiments of the invention steps 424 and step 426 are performed substantially contemporaneously.

The comparison can be done in more than one way. In one embodiment, each thermographic image is compared to a single previously acquired thermographic image. Alternatively, at least a few thermographic images are compared to a plurality of, e.g., all the previously acquired thermographic images. Optionally and preferably the method continues to step 427 in which the thermal changes are displayed on a display device.

The method continues to decision step 428 in which the method determines whether the thermal changes are below a predetermined threshold. If the changes are not below the threshold, the method loops back to step 424. If the changes are not below the threshold the method continues to step 430 in which a report indicating that the living body is at a generally stable thermal condition is issued. The value of the threshold depends on the thermal imaging device and is typically set to the thermal resolution thereof. Known in the art are thermal imaging devices with a resolution of 0.1° C. and below. For example, the Photon OEM Camera core is commercially available from FLIR and provides thermal resolution of less than 0.085 degrees centigrade, TH9100PMV is commercially available from NEC and provides thermal resolution of less than 0.06 degrees centigrade, and IVN 3200-HS is commercially available from IMPAC and provides resolution of less than 0.08 degrees centigrade. Thus, according to a preferred embodiment of the present invention the value of the threshold is about 0.1 degrees centigrade.

The present embodiments can also be used for monitoring the position of a medical device, such as a biopsy needle or a catheter in the living body. For example, when a biopsy needle is to be introduced into a tumor, thermospatial imaging can be used to ensure that the path of the needle is appropriate for performing the biopsy. Furthermore, since thermospatial imaging can be used, as stated, for determining the position and optionally size of a tumor, a combined procedure can be employed whereby the same thermospatial imaging system is used for determining the presence, position and optionally size of the tamer and for monitoring the path of the biopsy needle once introduced into the body.

In various exemplary embodiments of the invention the temperature of the medical device (needle, catheter, etc.) is set to a temperature which is sufficiently different from the average temperature of the body. This ensures that the medical device is detectable by the thermospatial imaging system. Once the temperature of the medical device is set, the medical device is introduced into the body. One or more synthesized thermospatial images of the body and the medical device can then be generated and used for monitoring the position or path of the device.

Reference is now made to FIG. 22 which is a schematic illustration of medical device 440 insertable into a living body. Device 440 can be used, for example, as a biopsy device, e.g., for performing standard breast biopsy procedures. A particular advantage of device 440 is that it allows to sense or measure temperature while being inserted into the body. Device 440 is preferably relatively small in size and does not produce a level of thermal conductivity that would affect the sensing made thereby.

Preferably, device 440 is capable of detecting and providing a profile of temperatures of the tumor and surrounding tissue with high accuracy, so as to enable the diagnosis of cancer at an early stage when the tumor is small in size.

Device 440 preferably comprises a hollow structure 442 having a proximal end 444, a distal end 446 and an optical fiber 448 extending from end 444 to end 446. Distal end 446 can be shaped as a tip so as to allow device 440 to be easily inserted into the body. Fiber 448 is designed and constructed to transmit thermal radiation from distal end 446 to proximal end 444. The thermal radiation can be measured or recorded by a suitable device, such as, but not limited to, a thermal imaging device 450 which optically communicates with fiber 448. Fiber 448 is made of a material suitable for guiding electromagnetic radiation in the infrared range. Fiber 448 can be made of a material which is different from the material of structure 442. In this embodiment, fiber 448 is introduced into a passageway 452 in structure 442. Alternatively, structure 442 can be made material suitable for guiding electromagnetic radiation in the infrared range in which case the passageway itself can serve as an optical fiber.

It is appreciated that in the embodiment illustrated in FIG. 22, no measurement or sensing of temperature is performed in structure 442. Rather, the thermal energy is guided by means of radiation through the optical fiber. This is substantially different from known temperature measuring probes, e.g., the probe disclosed in U.S. Pat. No. 6,419,635, in which the probe performs the measurement and transits the data to external location. Device 440 is therefore advantageous both from the standpoint of manufacturing process and from the standpoints of cost and availability.

Reference is now made to FIGS. 23*a-b* which are schematic illustrations of an illuminating device 460, according to various exemplary embodiments of the present invention. Device 460 can be used in a range imaging system, e.g., for illuminating the surface to be imaged with a pattern.

Device 460 comprises a light source 462 which generates a light beam 464, a dynamic beam deflector 466 and an image forming element 468. Light source 462 preferably comprises a laser device which emits laser beam. The light beam 464 can be either in the visible range or the infrared range, depending on the application form which device 460 is used. Also contemplated, is a light source which generate a light beam both in the visible range and in the infrared range, such as one of the IR-50 series, which is commercially available from Scitec Instruments Ltd, UK.

Beam deflector 466 serves for dynamically deflecting light beam 464 so as to scan the surface of image forming element 468, to define, e.g., a raster pattern thereacross. Beam deflector 466 can comprise a movable mirror or an array of movable mirrors, such as, but not limited to, a Digital Micromirror Device™, commercially available from Texas Instruments Inc., USA. Beam deflector 466 can also comprise an electrooptical element, preferably an electrooptical crystal which deflects the light beam in response to electrical bias applied thereto.

Image forming element 468 is better seen in FIG. 23*b* which shows element 468 from viewpoint A. As shown, element 468 comprises a plurality of distinguished regions, designated by reference signs 470-1, 470-2, . . . 470-M, . . . 470-N. At least a few of the distinguished regions re preferably designed for forming a different image. Regions 470 can be, for example, holographic elements, diffraction gratings and the like. In any event regions 470 allow selective transmission of light such that light passing through regions 470 constitutes an image.

In operation, when beam 464 scans the surface of element 468, different images are formed at different times. Thus, device 460 is capable of illuminating a surface with a series of patterns in a periodic manner. The scan rate of beam 464 on element 468 is preferably selected to allow rapid change of the formed images. This is advantageous because it facilitate fast range imaging. For example, the surface can be illuminated by a series of 10 or more patterns within the duration of a single frame (e.g., 20 milliseconds) hence to increase the rate of range imaging by an order of magnitude.

The present embodiments successfully provide a technique for constructing a three-dimensional spatial representation of a body. The technique is an improvement of a technique commonly known as "structured light technique" or "coded light technique". The technique is based on the observation that a stripe projected on a non-planar surface intersects the surface at a curve which can reflect the characteristic of surface. An image of the curve can be acquired by an imaging device imaged to form a plurality of measured points on the plane of imaging device, referred to as the imaging plane. The curve and the light source producing the stripe define another plane referred to as the light plane. There is a projected correspondence between points on the light plane and points on the imaging plane. Based on the projected correspondence the 3D coordinates of the points on the non-planar surface can be determined. In order to acquire image of the entire surface, coded patterns are projected instead of a single stripe, hence the terms "structured light" or "coded light."

A major problem with known structured light techniques is that the lateral resolution of the obtained image cannot be enhanced beyond the intrinsic resolution of the projector which used to produce the coded pattern. While many types of imaging devices are capable of acquiring images at rather small pixel size (of order of tens of microns), high resolution projectors are hardly attainable. For example, a SVGA projector generates 800 strips. For a projected area of about 40 cm, the width of a single stripe (or the gap between adjacent stripes) is about half a millimeter. The use of more sophisticated and expensive projector only marginally improve the resolution. An XGA projector, for example, generates 1024 strips, hence can only reduce the resolution by a factor of less than 30%. In both cases, however, it is recognized that the width of a single projected element extends over several pixels of the imaging device, and the achievable resolution is dictated by the resolution of the projector.

The present embodiments successfully overcome the aforementioned resolution limitation by providing a method 500 and system 600 for constructing a three-dimensional spatial representation of a body.

A flowchart diagram describing the method steps of method 500 in accordance with preferred embodiments of the present invention is provided in FIG. 24 and a schematic illustration of system 600 in accordance with preferred embodiments of the present invention is provided in FIG. 25.

Referring conjointly to FIGS. 24 and 25, method 500 begins at step 502 and continues to step 504 in which a body 610 is illuminated using a pattern projector 602. In various exemplary embodiments of the invention projector 602 projects coded patterns 604 on body 610 in two or more different colors in a manner such that coded patterns of different colors are mutually shifted. Shown in FIG. 25 are three mutually shifted coded patterns, 604*a*, 604*b* and 604*c*, which may correspond, for example, to coded patterns of red light, green light and blue light.

Projector 602 can be based on any technology known in the art, such as, but not limited to, LCD, DLP or a combination thereof. Projector 602 can provide many types pf patterns. For example, a pattern can include several stripes. The stripes can be uniform or they can have a linear slope of light intensity profile. Such pattern allows identifying several points on the stripes. Other types and shapes of patterns are not excluded from the scope of the present invention.

Broadly speaking, projector 602 comprises a light source 606 and optics 608. Light source 606 typically includes a matrix of polychromatic illumination units or cells, each capable of optical output of several primary colors (e.g., red, green and blue). Each illumination unit can also be subdivided to two or more monochromatic sub-units. Thus, for example, a polychromatic illumination unit can include a red sub-unit, a green sub-unit and a blue sub-unit as known in the art. Alternatively, the polychromatic illumination unit can operate without such subdivision, as in the case of, for example, DLP projectors. The matrix can be a passive matrix or an active matrix.

When light source 606 comprises a passive matrix, no light is generated within the unit and the unit is only able to block transmission of light generated by a backlight assembly of the light source, or enable reflection of light generated by a front illumination assembly of the light source. In this embodiment, each illumination unit comprises color filters such as a color wheel or an arrangement of red, green and blue (RGB) filters to provide optical output of different colors. When light source 606 comprises an active matrix, each illumination unit radiates light independently. In this embodiment, each unit can produce white light which is then filtered at the sub-unit level by color filters. Alternatively, each sub-unit can comprise a monochromatic light emitting element such as a light emitting diode or an organic light emitting diode.

The number of polychromatic illumination units of light source 606 is referred to as the resolution of projector 602. As will be appreciated by one ordinarily skilled in the art, the higher the number of pixels, the better the resolution. Known projectors are with resolution of 640×480 units (also known as VGA projector), 800×600 units (also known as SVGA projector), 1024×768 units (also known as XGA projector), 1366×768 units (also known as wide XGA or WXGA projector), 1280×1024 units (also known as SXGA projector), 1400×1050 units (also known as SXGA+ or SXGAplus projector), and 1600×1200 (also known as UXGA projector).

Each polychromatic illumination unit is responsible for illuminating a unit area on the illuminated surface, which unit area is also known in the literature as a "dot" or a "projected pixel". Since the projected pixel corresponds to an area on the surface (rather than the physical area of the corresponding illuminating unit) its size depends on the distance between the projector and the illuminated surface, and on the divergence of the light beam emitted from the illuminating units. Nonetheless, for a given projector and a given projection distance, the projected pixel can be characterized by a size, such as a diameter or an area. The resolution of projector 602 dictates the maximal number of projected pixels on the illuminated surface. Similarly, for a given coverage area of projector 602, the resolution dictates the lateral distance between the centers of adjacent projected pixels of projector 602.

Optics 608 optically manipulates the light beam generated by light source 606 to provide the coded pattern. Optics 608 can include, for example, a focusing or collimating element, a dicroic optic system, a diffraction grating, a holographic element, digital micromirror device chip and the like. Various combinations of such and similar optical elements are also contemplated. The mutually shift between coded patterns of different color is preferably achieved by optics 608. In various exemplary embodiments of the invention optics 608 redirects different wavelengths at different redirection angles. This can be achieved, for example, by designing optics 608 to optically manipulate light having a predetermined wavelength in the visible range (say, wavelength corresponding to a green or greenish light). Since optics 608 is designed for a particular wavelength, different optical manipulations are obtained for different wavelengths.

Projector 602 preferably, but not obligatorily, operates in sequential mode. In this preferred embodiment, the surface is illuminated such that two adjacent patterns of different colors are projected at different times. A pattern of a given color is preferably generated by activating a collection of illumination units in a manner that in each unit in the collection emits light as the same wavelength. An adjacent pattern can be generated by activating the same collection of illumination units to emit light as a different wavelength. Thus, according to a preferred embodiment of the present invention at least two adjacent patterns are generated using the same collection of illumination units.

The wavelengths of the patterns can correspond to primary colors of the units, or alternatively to predetermined blends of primary colors. When a pattern of a primary color, say a red pattern, is generated, each unit in the collection emits red light. An adjacent pattern can be generated by activating the same collection, e.g., to emit a green light, another adjacent pattern can be generated by activating the same collection to emit a blue light. Preferably, the sequential operation of projector 602 is such that a collection of units is activated to emit a pattern of a first color, then the same collection is activated to emit a pattern of a second color etc. Subsequently another collection of units is activated to emit a series of single color patterns and so on.

According to a preferred embodiment of the present invention projector 602 is designed and constructed such that coded patterns of different colors are mutually shifted by an amount which is lower than the characteristic distance between the centers of adjacent projected pixels. Preferably, coded patterns of different colors are mutually shifted by an amount which half, more preferably third the characteristic distance between the centers of adjacent projected pixels.

The present embodiments exploit different response of optics 608 to different wavelengths and generates adjacent patterns shifted by less than the size of a projected pixel. In various exemplary embodiments of the invention projector 602 operates in sequential mode of projector 602, so as to avoid mixing between adjacent patterns even though the distance between the patterns is smaller than the size of a single projected pixel. Yet, projector 602 can also operate is a simultaneous mode. In this embodiment, the acquisition (see step 506 and device 612, hereinafter) preferably employs an arrangement of color filters so as to allow identification of adjacent strips. In any event, the effective resolution of projector 602 is significantly increased. Preferably, the effective resolution of projector 602 is three times larger than the number of its illumination units.

More preferably, the effective resolution of projector 602 is nine times the number of its illumination units. This can be achieved by increasing the resolution three times in each lateral dimension.

Consider, for example, an RGB projector which produces strips on a surface. There is a certain amount of different locations on the surface which can be illuminated by a stripe. This number generally equals the width or length of the surface in units of projected pixels. When the projector operates in sequential mode, the number of different locations can be increased by a factor of three. This is because a particular linear collection of illumination units can project a red stripe on a first lateral location on the surface, a green stripe on a second lateral location on the surface, and a blue stripe on a third lateral location on the surface, where the first, second and third lateral locations are slightly shifted with respect to each other. Yet, the lateral extent of all three locations approximately equals to the diameter of a single projected pixel. Thus, had the collection illumination units projected a white stripe (formed be a blend of all RGB colors) on the surface, its width would have been about three times wider than the width of each primary color stripe.

The situation is illustrated in FIGS. 26a-d, showing the a first stripe 702 at lateral location 712 (FIG. 26a), a second stripe 704 at lateral location 714 (FIG. 26b), a third stripe 706 at lateral location 716 (FIG. 26c), and all three stripes extending over lateral location 712-716.

Similar consideration can be made for vertical as well as horizontal strips, in which case the resolution is increased by a factor of 3×3=9.

In various exemplary embodiments of the invention the shift between two adjacent stripes of different colors is less than the width of a single stripe. Formally, when the width of a stripe is w, the mutual shift between two adjacent stripes of different colors is X w, where 0<X<1, more preferably 0<X≤0.5, even more preferably 0.3≤X≤0.5, say about ⅓. For example, when the width of a stripe is 0.4 mm and projector 602 produces three different primary colors, the mutual shift is about 0.15 mm.

Method 500 continues to step 506 in which one or more images the coded patterns are acquired to provide image data. The acquisition can be done using an imaging device 612, such as a CCD or the like. The design and basic functions of imaging device 612 are well known in the art and are not described in any detail here. In addition to performing basic functions of image acquisition (such as, but not limited to, reading out and synchronizing the CCD chip, background subtraction, auto-exposure, auto-focus etc.), the electronic circuitry of device 612 preferably contains a memory medium for storing calibration data.

According to a preferred embodiment of the present invention the acquisition is done so as to distinguish between coded patterns of different colors. Thus, the resolution of imaging device 612 is at least as high as the effective resolution of projector 602. Additionally, since the coded patterns are generated in sequential manner, the acquisition of image comprises multiple readouts during a single exposure time. For example, when there are three primary colors, the acquisition of image comprises three readouts during a single exposure time, e.g., one readout for each generated pattern. Also contemplated are short exposure times as further detailed herein above (see FIGS. 16a-c and accompanying description).

Method 500 proceeds to step 508 in which the 3D positions of the coded patterns are calculated based on the image data. The calculation is performed using an image data processor 614 which is supplemented by an appropriate 3D position calculation algorithm as known in the art.

Broadly speaking, the algorithm preferably locates with the position of the coded patterns on the image. Optionally, the intensities of the obtained patterns are compared between each other. Once the patterns are identified, their 3D coordinates can be determined as known in the art, e.g., by triangulation. The geometric parameters of the system such as the distance between the light source and the imaging device, at angles under which the patterns are emitted, are generally known from the design of the system or determined in a suitable calibration process as known in the art. representative examples of calibration data, include, without limitation, triangulation distance, focal lengths, pixel sizes, angular positions, intensity profile of the coded patterns, and the like. The calculation of 3D coordinates is typically, but not exclusively, employed in a two stages: a low resolution stage in which 3D coordinates of only a portion of the patterns are determined, and a high resolution stage in which the 3D coordinates are computed for all patterns. The calculation of 3D coordinate is preferably executed in such accuracy so as to allow determination of adjacent patterns of different colors. In other words, the accuracy of the calculation is preferably such that allows distinguishing between objects laterally shifted by an amount which is lower than the distance between adjacent projected pixels. For example, when the patterns comprise stripes, the accuracy of calculation is compatible with the distance between two adjacent stripes.

Typically, about 10-20 patterns each consisting of about 10-50 stripes are sufficient to approximate the geometry of the surface. The three-dimensional representation of the surface can be approximated using a meshing algorithm as known in the art to provide a triangulated mesh.

The method ends at step 510.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of determining a number of thermally distinguishable objects in the living body, the method comprising:
   using a computer for obtaining a synthesized thermospatial image defined over a three-dimensional spatial representation of the living body and having thermal data associated with a surface of said three-dimensional spatial representation, said thermal data being characterized by closed isothermal contours surrounding at least one thermally distinguished areas on said surface;
   using a computer for determining an internal three-dimensional thermally distinguishable region in the living body based on said synthesized thermospatial image;
   analyzing said three-dimensional spatial representation so as to define a non-planar boundary within said three-dimensional spatial representation, wherein points residing on one side of said boundary correspond to a single thermally distinguished area on said surface while points residing on another side of said boundary correspond to a plurality of thermally distinguished areas on said surface; and
   comparing said internal three-dimensional thermally distinguishable region with said boundary so as to determine the number of thermally distinguishable objects in the living body.

2. The method of claim 1, wherein said determining said internal three- dimensional thermally distinguishable region comprises:
   identifying at least one thermally distinguishable area in said thermospatial image; calculating a spatial gradient of said surface at said area, thereby calculating a thermal path in the living body; and
   using at least two thermal trajectories so as to determine said internal three- dimensional thermally distinguishable region.

3. The method of claim 1, wherein said thermal data is arranged over said surface in a plurality of picture-elements each represented by an intensity value or grey-level and said determining said internal three- dimensional thermally distinguishable region comprises:

searching for at least one set of picture-elements represented by generally similar intensity values or grey-levels; and for at least one of said at least one set of picture-elements, defining a plurality of loci, each locus being associated with at least a pair of picture-elements of said set and defined such that each point of said locus is at equal thermal distances from individual picture-elements of said pair, and using said plurality of loci for determining said internal three-dimensional thermally distinguishable region.

4. Apparatus for determining a number of thermally distinguishable objects in the living body, the apparatus comprising:

an input unit for receiving a synthesized thermospatial image defined over a three-dimensional spatial representation of the living body and having thermal data associated with a surface of said three-dimensional spatial representation, said thermal data being characterized by closed isothermal contours surrounding at least one thermally distinguished areas on said surface;

a region determination unit for determining an internal three-dimensional thermally distinguishable region in the living body based on said synthesized thermospatial image;

an analyzer for analyzing said three-dimensional spatial representation so as to define a non-planar boundary within said three-dimensional spatial representation, wherein points residing on one side of said boundary correspond to a single thermally distinguished area on said surface while points residing on another side of said boundary correspond to a plurality of thermally distinguished areas on said surface; and a comparison unit for comparing said internal three-dimensional thermally distinguishable region with said boundary so as to determine the number of thermally distinguishable objects in the living body.

* * * * *